United States Patent [19]

Morimoto et al.

[11] Patent Number: 4,891,427

[45] Date of Patent: Jan. 2, 1990

[54] TRICYCLIC CEPHAM COMPOUNDS

[75] Inventors: Akira Morimoto; Noriyoshi Noguchi; Nobuo Choh, all of Osaka, Japan

[73] Assignee: Takeda Chemical Industries, Ltd., Osaka, Japan

[21] Appl. No.: 351,040

[22] Filed: May 12, 1989

Related U.S. Application Data

[62] Division of Ser. No. 72,144, Jul. 10, 1987.

[30] Foreign Application Priority Data

Jul. 15, 1986 [JP]   Japan .................................. 61-167283

[51] Int. Cl.$^4$ .................... C07D 513/14; A61K 31/54
[52] U.S. Cl. ...................................... 540/216; 540/215
[58] Field of Search ....................... 540/214, 215, 216; 514/210

[56] References Cited

FOREIGN PATENT DOCUMENTS 0253337  1/1988  European Pat. Off. .
2552089  3/1985  France .
1541832  3/1979  United Kingdom .

OTHER PUBLICATIONS

M. Hatanaka et al., "Synthesis of Tricyclic Cephalosporins", Chemical Abstracts, vol. 103, No. 1, Jul. 8, 1985, p. 548, Abstact No. 6090w.

B. D. Boles et al., "Nuclear Analogs of Beta-Lactam Antibiotics. 2, The Total Synthesis off 8-oxo-4-thia-1-azabicyclico [4.2.0]oct-2-ene-2-carboxylic acids", Chemical Abstracts, vol. 86, No. 25, Jun. 20, 1977, p. 602, Abstract No. 189823k.

Primary Examiner—Nicholas S. Rizzo
Attorney, Agent, or Firm—Wegner & Bretschneider

[57] ABSTRACT

The compounds having a 4,11-dioxo-3-oxa-8(or 7)-thia-1-azatricyclo[7,2,0,0$^{2,6}$]undecane-2-carboxylic acid skeleton as the base structure, their esters and their salts are useful antibacterial agents.

5 Claims, No Drawings

TRICYCLIC CEPHAM COMPOUNDS

This application is a divisional of U.S. Ser. No. 072,144 filed July 10, 1987, still pending.

This invention relates to a novel and antimicrobially active compound having 4,11-dioxo-3-oxa-8(or 7)-thia-1-azatricyclo[7,2,0,0$^{2,6}$]undecane-2-carboxylic acid skeleton, an ester thereof and a salt thereof, to a method of production thereof, to intermediates thereof and to use thereof.

Recently, a novel antibiotic TAN-588 (hereinafter referred to in some instances briefly as "TAN-588") exhibiting antimicrobial activities against gram-positive and gramnegative bacteria has been obtained from new species of microorganisms belonging to the genera Empedobacter and Lysobacter isolated from soil. Furthermore, its derivatives have been synthesized as disclosed in, for example, European patent application laid-open No. 191989.

The antibiotic TAN-588 has an entirely new skeleton consisting of a 3-oxoisoxazolidine ring having 5-oxo-2-tetrahydrofurancarboxylic acid bonded at its nitrogen atom.

On the other hand, cephalosporin has still occupied an important position as an antibiotic, and chemical modification thereof especially at the 1-, 2-, 3-, 4- and 7-positions of its cephem skeleton has been extensively developed.

The present invention is to provide an antimicrobially active compound having an entirely new skeleton having 5-oxotetrahydrofuran ring, which corresponds to a partial structure of TAN-588, introduced at the double bond of its cephem (or isocephem) skeleton, resulting in a totally novel and unique base skeleton which is remote from not only the TAN-588 structure and the cephem (or isocephem) skeleton but also any of the other known tricyclic compounds.

The present inventors have diligently studied a variety of compounds having the skeleton of TAN-588 or a partial skeleton thereof, succeeded in the synthesis of a tricyclic cepham (or isocepham) compound having the 5-oxotetrahydrofuran ring of TAN-588 introduced at the double bond of its cephem (or isocephem) skeleton. The chemically produced compound thus has an excellent antimicrobial activity.

More specifically, the present invention is concerned with:

(1) a compound having 4,11-dioxo-3oxa-8(or 7)-thia-1-azatricyclo[7,2,0,0$^{2,6}$]undecane-2-carboxylic acid skeleton or an ester thereof or a salt thereof, (2) a compound having the skeleton described in (1), especially having as a substituent at its 10-position an amino group or an organic residue bonded through nitrogen, (3) a compound represented by the formula

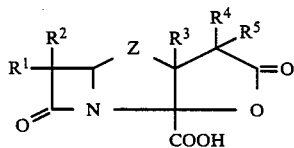

wherein R$^1$ stands for an amino group or an organic residue bonded through nitrogen, R$^2$ stands for hydrogen, methoxy or formylamino group, R$^3$, R$^4$, and R$^5$ independently stand for hydrogen or an organic residue, and Z stands for a group representable by the formula;

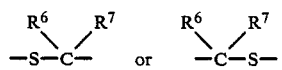

wherein R$^6$ and R$^7$ independently stand for hydrogen or an organic residue, respectively, or an ester thereof or a salt thereof, (4) A method of producing a compound having 4,11-dioxo-3-oxa-8(or 7)-thia-1-azatricyclo[7,2,0,0$^{2,6}$]undecane-2-carboxylic acid skeleton or an ester thereof or a salt thereof, which is characterized by subjecting to a ring closure reaction a compound having 2-oxo-3-(2-azetidinon-4-yl)thiomethyl(or methylthio)glutaric acid skeleton or an ester thereof or a compound having 3-(2-azetidinon-4-yl)thiomethyl(or methylthio)-5-oxotetrahydrofuran-2-carboxylic acid skeleton having a leaving group at its 2-position, or an ester thereof, (5) A compound having 2-oxo-3-(2-azetidinon-4-yl)thiomethyl(or methylthio)glutaric acid skeleton or an ester thereof or a salt thereof, (6) a compound having 3-(2-azetidinon-4-yl)thiomethyl(or methylthio)-5-oxo-tetrahydrofuran-2-carboxylic acid skeleton having a leaving group at the 2-position, or an ester thereof or a salt thereof, and (7) an antimicrobial agent containing a compound having 4,11-dioxo-3-oxa-8(or 7)-thia-1-azatricyclo[7,2,0,0$^{2,6}$]undecane-2-carboxylic acid skeleton or an ester thereof or a salt thereof.

Among the preferred compounds of this invention characterized by having a novel 4,11-dioxo-3-oxa-8(or 7)-thia-1-azatricyclo[7,2,0,0$^{2,6}$]undecane-2-carboxylic acid skeleton having 5-oxotetrahydrofuran ring introduced into a cepham (or isocepham) skeleton are those represented by the formula;

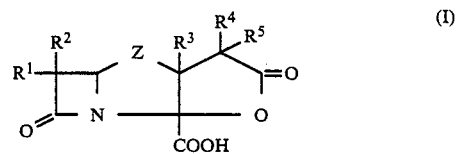

wherein R$^1$ stands for an amino group or an organic residue bonded through nitrogen, R$^2$ stands for hydrogen, methoxy or formylamino group, R$^3$, R$^4$ and R$^5$ independently stand for hydrogen or an organic residue, and Z stands for a group representable by the formula;

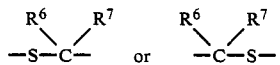

wherein R$^6$ and R$^7$ independently stand for hydrogen or an organic residue, respectively, or an ester thereof or a salt thereof.

As examples of the organic residue bonded through nitrogen represented by R$^1$ in the above formula, there are mentioned amino substituted through carbon such as acylamino, alkenylamino, ureido and thioureido and a group containing the group of the formula —CO—CO—NH—, thioamino, silylamino and phosphonoamino.

The acyl in the above-mentioned acylamino is exemplified by acyl groups which are used as substituents of the amino group at the 6-position of known penicillin derivatives, or acyl groups at the 7-position of cephalosporin derivatives and the like.

The said acylamino group is exemplified by, among others, groups represented by the formula

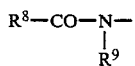

wherein $R^8$ stands for hydrogen, alkyl* (in the description of each group in the present specification, groups bearing asterisk * are those which may optionally have substituents), alkenyl*, cycloalkyl*, aryl*, heterocyclic ring*, alkoxy* or aryloxy*, $R^9$ stands for hydrogen or alkyl*, and $R^8$ and $R^9$ together form a ring*; groups represented by the formula

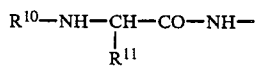

wherein $R^{10}$ stands for hydrogen, amino* acid residue*, amino-protecting group or a group represented by the formula $R^{12}$—$(CH_2)_n$—$C(=A)$— {wherein $R^{12}$ stands for heterocyclic ring*, alkoxy* or amino*, n denotes 0, 1 or 2, and A stands for O or S}, and $R^{11}$ stands for alkyl*, aryl*, cycloalkenyl* or heterocyclic ring*, respectively; groups represented by the formula $R^{13}$—$R^{14}$—CO—NH— wherein $R^{13}$ stands for a group represented by the formula

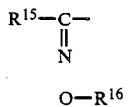

{wherein $R^{15}$ stands for alkyl*, heterocyclic ring*, or aryl*, $R^{16}$ stands for hydrogen, alkyl*, alkenyl*, cycloalkyl*, heterocyclic ring* or a group represented by the formula —$R^{17}$—$R^{18}$ (wherein $R^{17}$ stands for alkylene*, cycloalkylene* or alkenylene and $R^{18}$ stands for aryl*, carboxy* or its ester or mono- or di-alkylamide)}, and $R^{14}$ stands for a chemical bond or a group represented by the formula

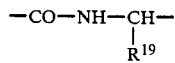

(wherein $R^{19}$ stands for alkyl*, aryl* or heterocyclic ring*), respectively; groups represented by the formula

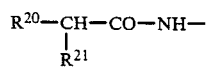

wherein $R^{20}$ stands for aryl*, heterocyclic ring* or cycloalkenyl*, and $R^{21}$ stands for hydroxy, sylfamoyl, sulfo, sulfoxy or acyloxy*, respectively, and groups represented by the formula $R^{22}$—$R^{23}$ $CH_2$—CO—NH— wherein $R^{22}$ stands for alkyl*, cyano, aryl*, aryloxy*, alkenyl, heterocyclic ring*, amino* or a group representable by the formula $R^{22'}$—$C(=S)$— wherein $R^{22'}$ stands for alkoxy, and $R^{23}$ stands for a chemical bond or —S—, respectively]. As the above-mentioned ureido or thioureido, use is made of groups represented by the formula

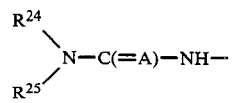

wherein $R^{24}$ and $R^{25}$ independently stand for hydrogen, alkyl*, aryl*, heterocyclic ring* or cycloalkyl, and A stands for O or S, respectively.

The formula

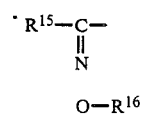

in $R^{13}$ represents syn-isomers of the formula

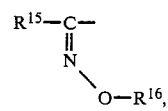

anti-isomers of the formula

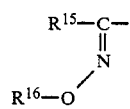

or a mixture thereof. Examples of the amino substituted through carbon as another example of the organic residue bonded through nitrogen represented by $R^1$ are groups represented by the formula $R^{26}$—NH— wherein $R^{26}$ stands for alkyl*, aryl*, alkenyl* or heterocyclic ring*, groups represented by the formula

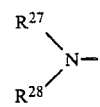

wherein $R^{27}$ and $R^{28}$ independently stand for alkyl*, aryl* or alkenyl*, and $R^{27}$ and $R^{28}$ may form a heterocyclic ring together with the adjacent nitrogen atom, and groups represented by the formula

wherein $R^{29}$, $R^{30}$ and $R^{31}$ independently stand for alkyl*, aryl* or alkenyl*, and $R^{29}$ and $R^{30}$ or $R^{31}$ may form a heterocyclic ring* together with the adjacent nitorgen atom, respectively. The third group is usually accompanied by a counter ion, i.e. an anion such as chloride, bromide hydroxy, etc.

Examples of the alkenylamino which exemplifies the organic residue bonded through nitrogen as shown by $R^1$ include groups representable by the formula

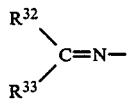

wherein R³² and R³³ independently stand for hydrogen, alkyl*, aryl*, cycloalkyl, amino* or heterocyclic ring*, and R³² and R³³ may form cycloalkyl* or a heterocyclic ring* together with the adjacent carbon atom.

Examples of the thioamino which exemplifies the organic residue bonded through nitrogen as shown by R¹ include groups representable by the formula R³⁴—SOₙ—NH— wherein R³⁴ stands for alkyl* or aryl* and n denotes 0, 1 or 2, respectively.

Examples of the silylamino which exemplifies the organic residue bonded through nitrogen as shown by R¹ include groups represented by the formula

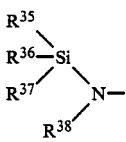

wherein R³⁵, R³⁶ and R³⁷ independently stand for alkyl* or aryl*, and they may form a cyclic group, and R³⁸ stands for hydrogen or silyl*.

Examples of the phosphoamino which exemplifies the organic residue as shown by R¹ include groups represnted by the formula

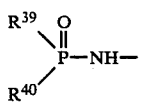

wherein R³⁹ and R⁴⁰ independently stand for alkyl*, aryl*, alkoxy* or aryloxy*, and R³⁹ and R⁴⁰ may form a heterocyclic group*.

Examples of the group containing the group of the formula —CO—CO—NH— which exemplifies the organic residue bonded through nitrogen as shown by R¹ include groups represented by the formula R⁴¹—CO—CO—NH— wherein R⁴¹ stands for hydrogen, alkyl*, alkoxy*, aryl*, aryloxy*, heterocyclic group* or amino*.

In the above formulae, the organic residue bonded through nitrogen as shown by R¹ is preferably those having a molecular weight up to 500.

The alkyl in R¹ is preferably straight-chain or branched alkyls having 1 to 6 carbon atoms, as exemplified by methyl, ethyl, n-propyl, isopropyl, n-butyl, isobutyl, sec-butyl, t-butyl, 1,1-dimethylpropyl, n-pentyl, isopentyl, n-hexyl, isohexyl, etc.

Substituents which the said alkyl may have include, for example, halogen, oxo, thioxo, nitro, amino (which may have as a substituent alkyl, alkenyl, cycloalkyl, aryl, acyl, carbamoyl or N-sulfocarbamoyl), sulfo, cyano, hydroxy, carboxy (which may be esterified with alkyl), cycloalkyl, cycloalkenyl, alkoxy(which may have as a substituent amino, hydroxy, carboxy, halogen, aryl, cycloalkyl or alkoxy), aryl (which may have as a substituent halogen, alkyl, alkoxy, alkylamino, amino, carbamoyl, sulfo, alkylsulfonyl, cyano, hydroxy, carboxy, nitro, acyloxy, aralkyloxy or sulfoxy), arylcarbonyl which may have substituents such as those mentioned above for aryl, aryloxy which may have substituents such as those mentioned above for aryl, heterocyclic ring (which may have as a substituent nitro, oxo, aryl, alkenylene, halogenoalkyl, alkylsulfonyl, alkyl, alkoxy, alkylamino, amino, halogen, carbamoyl, hydroxy, cyano, carboxy or sulfo), acyl (which may have as a substituent arylcarbonylhydrazino which may have as a substituent hydroxy, halogen, amino or nitro), acyloxy, alkoxycarbonyl, alkoxycarbonyloxy (which may have as a substituent halogen), acyloxyethoxy, aralkyl (which may have as a substituent alkyl, alkoxy, halogen, amino, hydroxy, nitro, cyano, carbamoyl or sulfamoyl), aralkyloxy (which may have as a substituent acyloxy, alkyl, alkoxy, halogen, amino, hydroxy, nitro, cyano, carbamoyl or sulfamoyl), hydroxysulfonyloxy, alkylsulfonyloxy, arylsulfonyloxy, alkylsulfonyl, aminosulfonyl, alkylsulfinyl, arylsulfonyl, alkylsulfinyl, alkylthio (which may have as a substituent cyano, halogen, carboxy, alkylamino, imino, carbamoyl or acylamino), arylthio, heterocyclic ring-thio (which may have as a substitutent cyano, hydroxy, amino, alkyl, halogen or oxo), heterocyclic ring (which may have as a substitutent cyano, hydroxy, amino, alkylamino, alkyl, halogen or oxo) alkylthio, iminomethylamino, iminoethylamino, silyl (which may have alkyl or aryl as a substituent), silyloxy which may have substituents such as those mentioned tioned above for silyl, phthalimido, succinimido, dialkylamino, dialkylaminocarbonyl, arylcarbonylamino, carbamoyl, carbamoyloxy, N-sulfocarbamoyloxy, alkylcarbonylcarbamoyloxy (which may have as a substituent halogen), alkoxyimino, and groups representable by the formula

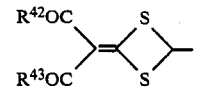

(wherein R⁴² and R⁴³ independently stand for a hydroxyl or amino group).

In the above formulae, the alkylene as represented by R¹⁷ is preferably those of 1 to 6 carbon atoms as exemplified by methylene, ethylene, trimethylene, tetramethylene, pentamethylene, hexamethylene, etc.

Substituents which the said alkylene group may optionally have include, for example, halogen, amino, hydroxy, alkoxy, carboxy, carbamoyl, cyano, nitro, etc.

In the above formulae, the cycloalkyl and that in the cycloalkyloxy or that forming the ring in the group represented by R¹ are preferably those of 3 to 8 carbon atoms as exemplified by cyclopropyl, cyclobutyl, cyclopentyl, cyclohexyl, cycloheptyl, cyclooctyl, etc.

Substituents which the said cycloalkyl group may optionally have include, for example, halogen, nitro, amino, hydroxy, sulfo, cyano, carboxy, oxo, thioxo, etc.

As the cycloalkylene in the groups in the above formulae, there are groups formed by cycloalkyls mentioned above having an additional chemical bonding hand.

In the above formulae, the aryl in the aryl, arylcarbonyl, aryloxycarbonyl, aryloxy and arylthio as represented by R¹ is exemplified by phenyl, naphthyl, biphenyl, anthryl, indenyl, etc.

Substituents which the said aryl group may have are exemplified by halogen, nitro, cyano, amino (optionally substituted with alkyl, alkenyl, cycloalkyl or aryl), sulfo, mercapto. hydroxy, carboxy, acyl, sulfoxy, sulfamoyl, carbamoyl, alkyl (optionally substituted with amino, halogen, hydroxy, cyano or carboxy), alkoxy aralkyloxy, alkylsulfonamido, methylenedioxy, alkylsulfonyl, alkylsulfonylamino, etc., and these groups may, together with cycloalkyl, form a fused ring (e.g. tetrahydronaphthyl, indanyl, acenaphthyl, etc.).

In the above formulae, the alkoxy as shown by $R^1$ is preferably those of 1 to 6 carbon atoms, as exemplified by methoxy, ethoxy, n-propoxy, i-propoxy, n-butoxy, i-butoxy, t-butoxy, n-pentyloxy, n-hexyloxy, etc.

Substituents which the said alkoxy group may optionally have are exemplified by halogen, nitro, amino, hydroxy, sulfo, cyano, carboxy, aryl (optionally substituted with nitro, amino, hydroxy, alkyl or alkoxy), silyl (optionally substituted with alkyl, aryl or aralkyl), etc.

In the above formulae, the alkylthio in the group as shown by $R^1$ is preferably those of 1 to 6 carbon atoms as exemplified by methylthio, ethylthio, n-propylthio, i-propylthio, n-butylthio, i-butylthio, n-pentylthio, n-hexylthio, etc. Substituents which the said alkylthio group may optionally have are exemplified by those such as those for the above-mentioned alkoxy.

The alkenyl in the group as shown by $R^1$ in the above formula is preferably, among others, those having 1 to 6 carbon atoms as exemplified by methylene, vinyl, allyl, isopropenyl, 1-propenyl, 2-butenyl, 3-methyl-3-butenyl, 1,3-butadienyl, 1,3-pentadienyl, 4-pentenyl, 1,3-hexadienyl, ethylidene, propylidene, isopropylidene, butylidene, etc.

Substituentss which the said alkenyl group may optionally have are exemplified by halogen, nitro, amino (optionally substituted with acyl), sulfo, cyano, hydroxy, carboxy, carbamoyl, sulfamoyl, aryl, acyl, etc.

The alkenylene in the group as shown by $R^1$ in the above formulae is preferably, among others, those having 2 to 6 carbon atoms as exemplified by vinylene, 1-propenylene, 2-butenylene, 2-pentenylene, 1,3-hexadienylene, etc.

In the above formulae, the cycloalkenyl as shown by $R^{11}$ and $R^{20}$ is preferably, among others, those having 3 to 8 carbon atoms as exemplified by 1-cyclopropenyl, 1-cyclobutenyl, 1-cyclopentenyl, 2-cyclopentenyl, 3-cyclopentenyl, 1-cyclohexenyl, 2-cyclohexenyl, 3-cyclohexenyl, 1-cycloheptenyl, 1,4-cyclohexadienyl, etc.

Substituents which the said cycloalkenyl group may optionally have are exemplified by halogen, nitro, amino, sulfo, cyano, hydroxy, carboxy, carbamoyl, sulfamoyl, etc.

In the above formulae, the heterocyclic ring in the groups as shown by $R^1$ or the heterocyclic ring formed thereby is exemplified by 5- to 7-membered heterocyclic groups containing one sulfur, nitrogen or oxygen atom, 5- to 6-membered heterocyclic groups containing 2 to 4 nitrogen atoms and 5- to 6-membered heterocyclic group containing 1 to 2 nitrogen atoms and one sulfur or oxygen atom, and these heterocyclic groups may be fused with a 6-membered cyclic group containing not more than two nitrogen atoms, benzene ring or a 5-membered cyclic group containing one sulfur atom.

Specific examples of the above heterocyclic groups include pyridine-(2-,3- or 4-yl), pyrimidine-(2-,4- or 5-yl), pyrazin-2-yl, pyridazin-(3- or 4-yl), piperazin-1-yl, piperidin-1-yl, pyrazol-(1-,3- or 4-yl), 4H-pyran-3-yl, 4H-thiopyran-3-yl, thiazol-(2-,4- or 5-yl), isothiazol-(3-,4- or 5-yl), oxazol-(2-,4- or 5-yl), isoxazol(3-,4- or 5-yl), pyrido[2,3-d]pyrimidin-(2-,3-,4-,5-, or 7-yl), benzo[1,2-b]-4H-pyran-3-yl, 1,8-naphthylidin(2-,3-,4-,5-, or 7-yl), 1,7-naphthylidin-(2-,3-,4-,5-,6- or 7-yl), 1,6-naphthylidin-(2-,3-,4-,5-,7- or 8-yl), 1,5-naphthylidin-(2-,3-,4-,6-,7- or 8-yl), 2,7-naphthylidin-(1-,3-,4-,5-,6- or 8-yl), 2,6-naphthylidin-(1-,3-,4-,5-,7- or 8-yl), quinolin-(2-,3-,4-,5-,6-,7- or 8-yl), thieno[2,3-b]pyridin-(2- or 3-yl), tetrazol-(1- or 5-yl), 1,3,5-thiadiazol-(2- or 4-yl), 1,3,5-oxadiazol-(2- or 4-yl), triazin-2-yl, 1,2,3-triazol-(4-or 5-yl), 1,3,5-triazol-(2- or 5-yl), thiophen-(2- or ;b 3-yl), pyrrol-(1-,2- or 3-yl), furan-(2- or 3-yl), pyrrolidin-1-yl, imidazolidin-(1-,2- or 4-yl), diethiethan-2-yl, benzo[1,2-b]thiophen-(2- or 3-yl), indol-(1-,2- or 3-yl), isoindolizin-(1-,2- or 3-yl), etc.

Substituents which the said heterocyclic groups may optionally have are exemplified by amino (optionally substituted with acyl, halogen-substituted alkylacyl, phenyl or alkyl), halogen, nitro, sulfo, cyano, hydroxy, carboxy, oxo, thioxo, $C_{1-10}$-alkyl[optionally substituted with aryl, halogen, amino, hydroxy, carboxy, alkoxy, alkylsulfonyl, dialkylamino or phosphono (optionally substituted with alkyl)], cycloalkyl, alkoxy(optionally substituted with halogen or hydroxy), acyl of 1 to 4 carbon atoms, aryl (optionally substituted with halogen, nitro, alkyl, alkoxy, amino, sulfo, hydroxy or cyano), oxo, thioxo, amino acid residue-thio(examples of the amino acid residue include amino acid residues similar to those to be mentioned below), $C_{1-10}$-alkylthio[optionally substituted with aryl, halogen, amino, hydroxy, carboxy, alkoxy, alkylsulfonyl, dialkylamino or phosphoric acid(optionally substituted with alkyl)], heterocyclic ring (optionally substituted with alkyl, alkoxy, halogen, nitro, cyano, carboxy, formyl or alkylsulfonyl), groups representable by the formula $R^{44}$—CH=N— [wherein $R^{44}$ stands for heterocyclic ring(optionally substituted with alkyl, alkoxy, halogen, nitro, cyano, hydroxy, carboxy, formyl or alkylsulfonyl)], etc.

In the above formulae, the cyclic group formed by $R^8$ together with $R^9$ is exemplified by those formed together with phthaloyl, succinyl, maleoyl, citraconoyl, glutaryl or adipoyl, and, as the ring thus formed, 2,2-dimethyl-5-oxo-4-phenyl-imidazolidine, etc. are also mentioned. Substituents which the said cyclic groups may optionally have are exemplified by halogen, nitro, amino, hydroxy, sulfo, cyano, carboxy, etc.

In the above formulae, the acyl in the acyloxy as shown by $R^1$ are preferably those of 1 to 4 carbon atoms, which are exemplified by formyl, acetyl, propionyl, butyryl, etc., and substituent groups for them are exemplified by alkyl(optionally substituted with amino, halogen, cyano, alkoxy, carboxy or hydroxy), etc.

In the above formulae, the amino acid residue as shown by $R^{10}$ is exemplified by glycyl, alanyl, valyl, leucyl, isoleucyl, seryl, threonyl, cysteinyl, cystyl, methionyl, α- or β-aspartyl, α- or γ-glutamyl, lysyl, arginyl, phenylalanyl, phenylglycyl, tyrosyl, histidyl, trytophanyl, prolyl, etc.

Substituents which the said amino acid residue may optionally have are exemplified by halogen, hydroxy, sulfo, carboxy, cyano, alkylamino, aralkyloxycarbonyl, aralkyloxy, guanidino, etc.

In the above formulae, as protective groups for the amino group as represented by $R^{10}$, use is conveniently made of those used for this purpose in the fields of, for example, β-lactam and peptide synthesis. Specific examples of them include aromatic acyl groups such as phthaloyl, 4-nitrobenzoyl, 4-tert-butylbenzoyl, 4-tert-butylbenzenesulfonyl, benzenesulfonyl, toluenesulfonyl, etc.; aliphatic acyl groups such as formyl, acetyl, propionyl, monochloroacetyl, dichloroacetyl, trichloroacetyl, methanesulfonyl, ethansfulonyl, trifluoroacetyl, malonyl, succinyl, etc.; esterified carboxyl groups such as methoxycarbonyl, ethoxycarbonyl, t-butoxycarbonyl, isopropoxycarbonyl, 2-cyanoethoxycarbonyl, 2,2,2-trichloroethoxycarbonyl, benzyloxycarbonyl, 4-nitrobenzyloxycarbonyl, 4-methoxybenzyloxycarbonyl, diphenylmethyloxycarbonyl, methoxymethyloxycarbonyl, acetylmethyloxycarbonyl, isobornyloxycarbonyl, phenyloxycarbonyl, etc.; methylene groups such as (hexahydro-1H-azepin-1-yl)methylene; sulfonyl groups such as 2-amino-2-carboxyethylsulfonyl, etc.; and, further, amino-protecting groups other than acyl groups, such as trityl, 2-nitrophenylthio, benzylidene, 4-nitrobenzylidene, di- or tri-alkylsilyl, benzyl, 4-nitrobenzyl, etc. Selection of the said protective groups is not specifically limited in this invention, but, among others, monochloroacetyl, benzyloxycarbonyl, 4-methoxybenzyloxycarbonyl and 4-nitrobenzyloxycarbonyl are especially preferable.

In the above formulae, substituent groups in the optionally substituted carboxy group in the groups as represented by $R^1$ include, for example, such groups as conventionally used as carboxy-protecting groups, and they are exemplified by alkyl(optionally substituted with halogen, cyano or hydroxy), aryl(optionally substituted with alkyl, alkoxy, halogen, hydroxy, acyloxy, sulfo, cyano, nitro or sulfamoyl), aralkyl (optionally substituted with substituents as mentioned above for aryl), silyl(optionally substituted with alkyl, aryl or aralkyl), heterocyclic ring (optionally substituted with amino, alkylamino, sulfamoyl, carbamoyl, halogen, cyano or nitro), amino(optionally substituted with alkyl, aryl, cyclo-alkyl, sulfo or aralkyl; and optionally forming 5- or 6-membered heterocyclic ring together with nitrogen in the said amino group), etc.

In the above formulae, the ester group in the ester of the carboxy as represented by $R^{18}$ is exemplified by alkyl-ester having 1 to 6 carbon atoms or benzyl ester which may be substituted with nitro, alkyl, alkoxy, hydroxy, cyano and its specific examples include methyl ester, ethyl ester, propyl ester, propyl ester, n-butyl ester, isobutyl ester, tert-butyl ester, 4-nitrobenzyl ester.

Substituent groups in the optionally substituted amino in the group as represented by $R^1$ in the above formulae are exemplified by amidine, iminomethyl, imino(aryl-substituted) methyl, guanidylcarbonyl, heterocyclic ring*(optionally substituted with substituents similar to those mentioned above for heterocyclic rings), imino(optionally substituted with heterocyclic ring)methyl, alkylcarbonyl, arylcarbonyl, hyroxyalkyl, alkyl, etc.

Sustituent groups in the optionally substituted silyl in the group as represented by $R^1$ in the above formulae are exemplified by alkyl, aryl, aralkyl, etc.

The above $R^{35}$, $R^{36}$, and $R^{37}$, together with $R^{38}$, may form a cyclic group, as exemplified by 2,5-disilylazacyclopentyl, etc., which may have a substituent group such as alkyl, aryl, etc.

The halogen in the description of the above substituent groups is exemplified by chlorine, bromine, fluorine and iodine.

The alkyl in the description of the above substituent groups is, unless otherwise specified, preferably those of 1 to 10, more preferably 1 to 6, still more preferably 1 to 4 carbon atoms, which are exemplified by methyl, ethyl, n-propyl, i-propyl, n-butyl, i-butyl, t-butyl, sec-butyl, n-pentyl, isopentyl, n-hexyl, isohexyl, heptyl, octyl, nonyl, decyl, etc.

The cycloalkyl as the above substituent group is, unless otherwise specified, preferably those of 3 to 6 carbon atoms, as exemplified by cyclopropyl, cyclobutyl, cyclopentyl, cyclohexyl, etc.

The alkoxy as the above substituent group is, unless otherwise specified, those of 1 to 4 carbon atoms, as exemplified by methoxy, ethoxy, n-propoxy, i-propoxy, n-butoxy, i-butoxy, t-butoxy, etc.

The aryl as the above substituent group is exemplified by phenyl, naphthyl, etc.

The heterocyclic ring as the above substituent group is exemplified by those similar to heterocyclic rings mentioned above.

The acyl as the above substituent group is, unless otherwise specified, preferably those of 1 to 6, more preferably 1 to 4 carbon atoms, as exemplified by formyl, acetyl, propionyl, butyryl, isobutyryl, valeryl, isovaleryl, pivaloyl, hexanoyl, etc.

The aralkyl as the above substituent group is exemplified by benzyl, phenethyl, phenyl-propyl, etc.

The alkenyl as the above substituent group includes those similar to the alkenyl mentioned above.

The amino acid residue as the above substituent group includes those such as the amino acid residue as shown by $R^{12}$.

The R5- to 6-membered heterocyclic ring formed together with the nitrogen in the amino group, as the above substituent group, is exemplified by piperidine, pyrrolidine, imidazolidine, morpholine, piperazine, etc.

The subsituent groups in not only each of the foregoing groups but also each below-mentioned group which may be substituted with asterisk* marked are preferably in number of 1 to 3. Among substituents which groups such as alkyl*, alkenyl*, cycloalkyl*, alkoxy*, aryloxy*, cycloalkenyl*, alkylene*, cycloalkylene, aryl*, aryloxy* and heterocyclic ring*, and carboxy* group may have, preferred are halogen, amino, hydroxy, carboxy, cyano and nitro. As the substituents of aryl*, aryloxy*, heterocyclic ring* groups and carboxy* group, also preferred are alkyl, alkoxy, halogen-substituted alkylacylamino, alkylamino. Among substituents of an amino acid residue*, preferred are halogen, alkylamino, hydroxy, carboxy. As the substituents of an amino group, alkylcarbonyl, arylcarbonyl and alkyl are preferred, and as those of acyloxy, preferred is alkyl which may be substituted by the above-mentioned preferred substituents.

In the above-mentioned acyl group, acylamino groups represented by the formula;

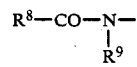

are specifically exemplified by 3-(2,6-dichlorophenyl)-5-methylisoxazol-4-yl-carbonylamino, 4-ethyl-2,3-dioxo-1-piperazinocarbonyl, 3-phenyl-5-methylisoxazol-4-yl-carbonylamino, 3-(2-chlorophenyl)-5-methylisoxazol-4-yl-carbonylamino, 3-(2-chloro-6-fluorophenyl)-5-methylisoxazol-4-yl-carbonylamino, nicotinylamino, benzoylamino, 4-bromobenzoylamino, 2,6-dimethoxybenzoylamino, formylamino, acetylamino, propionylamino, butyrylamino, isobutyrylamino, pivaloylamino, methoxycarbonylamino, benzyloxycarbonylamino, 1-amino-cyclohexylcarbonylamino, 2-aminocyclohexylcarbonylamino, 3-ethoxynaphthoylamino, 2-(2-amino-4-thiazoyl)-2-ethylideneacetylamino, 2-(2-amino-4-thiazolyl)-2-chloromethylene-acetylamino, phthalimido, succinimido, 1,2-cyclohexanedicarboxyimido, 2-(trimethylsilyl)ethoxycarbonylamino, 2,2-dimethyl-5-oxo-4-phenylimidazolidine, 4-(carbamoylcarboxymethylene)-1,3-dithiethan-2-yl-carbonylamino, etc.

Specific examples of the acylamino group represented by the formula

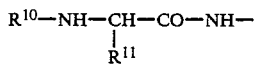

include, among others, D-alanylamino, N-carbobenzoxy-γ-D-glutamyl-D-alanylamino, D-phenylglycyl-D-alanylamino, N-carbobenzoxy-D-alanylamino, N-carbobenzoxy-D-phenylglycylamino, D-alanyl-D-phenylglycylamino, γ-D-glutamyl-D-alanylamino, 2-(4-ethyl-2,3-dioxo-1-piperazinocarboxamido)-2-phenylacetylamino, 2-(4-cyclohexyl-2,3-dioxo-1-piperazinocarboxamido)-2-phenylacetylamino, 2-(4-ethyl-2,3-dioxo-1-piperazinocarboxamido)-2-(4-sulfoxyphenyl)acetylamino, N-(4-ethyl-2,3-dioxo-1-piperazinocarbonyl)-D-alanylamino, N-(4-ethyl-2,3-dioxo-1-piperazinocarbonyl)-D-phenylglycylamino, 2-(2-amino-4-thiazolyl)-2-(4-ethyl-2,3-dioxo-1-piperazinocarboxamido)acetylamino, 2-(4-hydroxy-6-methylnicotinamido)-2-phenylacetylamino, 2-(4-hydroxy-6-methylnicotinamido)-2-(4-hydroxyphenyl)acetylamino, 2-{5,8-dihydro-2-(4-formyl-1-piperazinyl)-5-oxopyrido[2,3-d]pyrimidine-6-carboxamido}-2-phenylacetylamino, 2-(3,5-dioxo-1,2,4-triazine-6-carboxamido)-2-(4-hydroxyphenyl)acetylamino, 2-(3-furfurylideneamino-2-oxoimidazolidine-1-carboxamido)-2-phenylacetylamino, 2-(coumarin-3-carboxamido)-2-phenylacetylamino, 2-(4-hydroxy-7-methyl-1,8-naphthylidene-3-carboxamido)-2-phenylacetylamino, 2-(4-hydroxy-7-trifluoromethyl-quinoline-3-carboxamido)-2-phenylacetylamino, N-[2-(2-amino-4-thiazolyl)acetyl]-D-phenylglycylamino, 2-(6-bromo-1-ethyl-1,4-dihydro-4-oxothieno[2,3-b]pyridine-3-carboxamido)-2-phenylacetylamino, 2-(4-ethyl-2,3-dioxo-1-piperazinocarboxamido)-2-thienylacetylamino, 2-(4-n-pentyl-2,3-dioxo-1-piperazinocarboxamido)-2-thienylacetylamino, 2-(4-n-octyl-2,3-dioxo-1-piperazinocarboxamido)-2-thienylacetylamino, 2-(4-cyclohexyl-2,3-dioxo-1-piperazinocarboxamido)-2-thienylacetylamino, 2-[4-(2-phenylethyl)-2,3-dioxo-1-piperazinocarboxamido]-2-thienylacetylamino, 2-(3-methylsulfonyl-2-oxoimidazolidine-1-carboxamido)-2-phenylacetylamino, 2-(3-furfurylideneamino-2-oxoimidazolidine-1-carboxamido)-2-(4-hydroxyphenyl)acetylamino, 2-(4-ethyl-2,3-dioxo-1-piperazinocarboxamido)-2-(4-benzyloxyphenyl)acetylamino, 2-(4-ethyl-2,3-dioxo-1-piperazinocarboxamido)-2-(4-methoxyphenyl)acetylamino, 2-(8-hydroxy-1,5-naphthylidine-7-carboxamido)-2-phenylacetylamino, 2-(2-amino-4-thiazolyl)-2-formamidoacetylamino, 2-(2-amino-4-thiazolyl)-2-acetamidoacetylamino, 2-phenyl-2-ureidoacetylamino, 2-phenyl-2-sulfoureidoamino, 2-thienyl-2-ureidoacetylamino, 2-amino-3-sulfamoylpropionylamino, 2-amino-2-(1H-indol-3-yl)acetylamino, 2-amino-2-(3-nenzo[b]thienyl)acetylamino, 2-amino-2-(2-naphthyl)acetylamino, D-phenylglycyl, D-2-amino-(4-hydroxyphenyl)acetylamino, D-2-amino-2-(1,4-cyclohexadienyl)acetylamino, D-2-amino-2-(1-cyclohexenyl)acetylamino, D-2-amino-2-(3-chloro-4-hydroxyphenyl)acetylamino, 2-hydroxymethylamino, 2-(1-cyclohexenyl)-2-(4-ethyl-2,3-dioxo-1-piperazinocarboxamido)acetylamino, N-[2-(4-ethyl-2,3-dioxo-1-piperazinocarbonyl)]-D-threonylamino, 2-guanylcarboxamido-2-phenylacetylamino, 2-(4-ethyl-2,3-dioxo-1-piperazinocarboxamido-2-(3,4-dihydroxyphenyl)acetylamino, 2-(4-carboxy-5-imidazolylcarboxamido)-2-phenylacetylamino, 2-amino-2-(3-methylsulfonamidophenyl)acetylamino, etc.

Specific examples of the acylamino group represented by the formula $R^{13}-R^{14}-CO-NH-$ include, among others, N-[2-(2-amino-4-thiazolyl)-2-methoxyiminoacetyl]-D-alanylamino, N-[2-(2-amino-4-thiazolyl)-2-methoxyiminoacetyl]-D-phenylglycylamino, 2-(2-amino-4-thiazolyl)-2-[2-(2-amino-4-thiazolyl)-2-methoxyiminoacetammido]acetylamino, 2-(2-chloroacetamido-4-thiazolyl)-2-methoxyiminoacetylamino, 2-(2-amino-4-thiazolyl)-2-methoxyiminoacetylamino, 2-(2-amino-4-thiazolyl)-2-ethoxyiminoacetylamino, 2-(2-amino-4-thiazolyl)-2-isopropoxyiminoacetylamino, 2-(2-amino-4-thiazolyl)-2-butoxyiminoacetylamino, 2-(2-amino-4-thiazolyl)-2-cyclopropylmethyloxyiminoacetylamino, 2-(2-amino-4-thiazolyl)-2-benzyloxyiminoacetylamino, 2-(2-amino-4-thiazolyl)-2-allyloxyiminoacetylamino, 2-(2-amino-4-thiazolyl)-2-[(1-methyl-1-carboxyethyl)oxyimino]acetylamino, 2-(2-amino-4-thiazolyl)-2-[(1-methyl-1-methoxycarbonylethyl)oxyimino]acetylamino, 2-(2-amino-4-thiazolyl)-2-carboxymethyloxyiminoacetylamino, 2-(2-amino-4-thiazolyl)-2-carboxyvinyloxyiminoacetylamino, 2-(2-amino-4-thiazolyl)-2-carboxyethyliminoacetylamino, 2-(2-amino-4-thiazolyl)-2-methoxycarbonylethyloxyiminoacetylamino, 2-(2-amino-5-chloro-4-thiazolyl)-2-methoxyiminoacetylamino, 2-(2-amino-5-bromo-4-thiazolyl)-2-methoxyiminoacetylamino, 2-(2-amino-4-thiazolyl-2-hydroxyiminoacetylamino, 2-thienyl-2-methoxyiminoacetylamino, 2-furyl-2-methoxyiminoacetylamino, 2-(1,2,4-thiadiazol-3-yl)-2-methoxyiminoacetylamino, 2-(1,2,4-thiadiazol-5-yl)-2-methoxyiminoacetylamino, 2-(1,3,4-thiadiazolyl-2-methoxyiminoacetylamino, 2-(4-hydroxyphenyl)-2-methoxyiminoacetylamino, 2-phenyl-2-methoxyiminoacetylamino, 2-phenyl-2-hydroxyiminoacetylamino, 2-[4-(γ-D-glutamyloxy)phenyl]-2-oxyiminoacetylamino, 2-[4-(3-amino-3-carboxypropoxy)phenyl]-2-hydroxyiminoacetylamino, 2-thienyl-2-hydroxyiminoacetylamino, 2-(5-amino-1,2,4-thiadiazol-3-yl)-2-methoxyiminoacetylamino, 2-(5-amino-1,2,4-thiadiazol-3-yl)-2-ethoxyiminoacetylamino, 2-(5-amino-1,2,4-thiadiazol-3-yl)-2-carboxymethyloxyiminoacetylamino, 2-(5-amino-1,2,4-thiadiazol-3-yl)-2-[(1-methyl-1-carboxyethyl)oxyimino]acetylamino, 2-(2-amino-4-thiazolyl)-2-(2-amino-2-carboxy)ethyloxyiminoacetylamino, 2-(2-amino-4-thiazolyl)-2-(dimethylamidomethyloxyimino, 2-(2-amino-4-thiazolyl)-2-(3,4-diacetoxy-benzoyloxyimino)acetylamino, 2-(2-amino-4-thiazolyl)-2-(1-carboxy-cyclopropyloxyimino)acetylamino, 2-(2-amino-4-thiazolyl)-2-(1-carboxy-cyclobutyloxyimino)acetylamino, 2-(2-amino-4-thiazolyl)-2-(2-imidazolylmethyloxyimino)acetylamino, 2-(2-amino-4-thiazolyl)-2-(2-methyl-4-nitro-1-imidazolylethyloxyimino)acetylamino, 2-(2-amino-4-thiazolyl)-2-(3-pyrazolylmethyloxyimino)acetylamino, 2-(2-amino-4-thiazolyl)-2-(1H-tetrazol-5-yl-methyloxyimino) acetylamino, 2-(2-amino-4-thiazolyl)-2-(2-oxo-3-pyrrolidinyloxyimino)acetylamino, 2-[2-(2-amino-2- carboxyethylthio)]-4-thiazolyl-2-methox-yiminoacetylamino and 2-(2-thioxo-4-thiazolidinyl)-2-methoxyiminoacetylamino.

Specific example of the acylamino represented by the formula

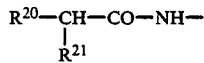

include, among others, 2-phenyl-2-sulfoacetylamino, 2-hydroxy-2-phenylacetylamino, 2-phenyl-2-sulfamoylacetylamino, 2-carboxy-2-phenylacetylamino, 2-(4-hydroxyphenyl)-2-carboxyacetylamino, 2-phenoxycarbonyl-2-phenylacetylamino, 2-phenyl-2-tolyloxycarbonylacetylamino, 2-(5-indanyloxycarbonyl)-2-phenylacetylamino, 2-formyloxy-2-phenylacetylamino, 2-alanyloxy-2-phenylacetylamino, 2-carboxy-2-thienylacetylamino, 2-(2-methylphenoxycarbonyl)-2-thienylacetylamino, 2-(2-amino-4-thiazolyl)-2-hydroxyacetylamino and 2-[4-(2-amino-2-carboxyethoxycarboxamido) phenyl]-2-hydroxyacetylamino.

Specific examples of the acylamino group represented by the formula $R^{22}-R^{23}-CH_2-CO-NH-$ include, among others, cyanoacetylamino, phenylacetylamino, phenoxyacetylamino, trifluoromethylthioacetylamino, cyanomethylthioacetylamino, difluoromethylthioacetylamino, 1H-tetrazolyl-1-acetylamino, thienylacetylamino, 2-(2-amino-4-thiazolyl)acetylamino, 4-pyridylthioacetylamino, 2-thienylthioacetylamino, 3,5-dichloro-1,4-dihydro-4-oxopyridine-1-acetylamino, β-carboxyvinylthioacetylamino, 2-(2-aminomethylphenyl)acetylamino, 2-chloroacetylamino, 3-aminopropionylamino, (2-amino-2-carboxy)ethylthioacetylamino, 4-amino-3-hydroxybutyrylamino, 2-carboxyethylthioacetylamino, 2-benzyloxycarbonylamino-acetylamino, β-carbamoyl-β-flurovinylthioacetylamino, 2-(1-isopropylamino-1-isopropyliminomethylthio)acetylamino, 2-[1-(2-dimethylaminoethyl)-1H-tetrazol-5-yl-thio]acetylamino, 2-(1-methyl-1,3,5-triazol-2-yl)acetylamino, and 2-(4-cyano-3-hydroxy-5-isothiazolylthio)acetylamino.

Specific examples of the group represented by the formula

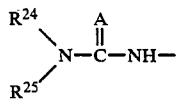

include, among others, carbamoylamino, methylaminocarbonylamino, ethylaminocarbonylamino, t-butylaminocarbonylamino, isobutylaminocarbonylamino, dimethylaminocarbonylamino, 2-methylphenylaminocarbonylamino, phenylaminocarbonylamino, 3-chlorophenylaminocarbonylamino, 4-nitrophenylaminocarbonylamino, 4-bromophenylaminocarbonylamino, thiocarbamoylamino, methylaminothiocarbonylamino, ethylaminothiocarbonylamino, phenylaminothiocarbonylamino, dimethylaminocarbonylamino and 3-fluorophenylaminocarbonylamino.

Specific examples of the group represented by the formula $R^{26}-NH-$ include, among others, methylamino, ethylamino, allylamino, cyclohexylamino, cyclohexylmethylamino, benzylamino, 4-chlorobenzylamino, phenylamino, 2-imidazolylamino, 1-methyl-2-imidazolylamino, 2-(2-amino-4-thiazolyl)-2-methoxyiminothioacetylamino, 1-benzyl-4-pyridiniumamino and 2-acetyl-1-methylvinylamino.

Specific examples of the alkylamino group represented by

include, among others, dimethylamino, diethylamino, dipropylamino, dibenzylamino, dicyclohexylamino, N-benzyl-N-methylamino, diallylamino, N-phenyl-N-methylamino, pyrrolidinyl, piperazinyl and morpholinyl.

Specific examples of the alkylammonium group represented by the formula

include, among others, trimethylammonium, triethylammonium, tribenzylammonium, methylpyrrolidinium and methylpiperidinium.

Specific examples of the alkenylamino group represented by the formula

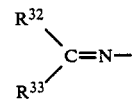

include, among others, dimethylaminoethyleneamino, 1-dimethylaminoethylideneamino, hexahydro-1H-azepine-1-yl-methyleneamino, 1-(N-benzyl-N-methylamino)ethylideneamino, 4-dimethylaminobenzylideneamino, (p-nitro)benzylideneamino and benzylideneamino.

Specific examples of the thioamino group represented by the formula $R^{34}-S(O)n-NH-$ include, among others, benzenesulfonylamino, 4-methoxybenzenesulfonylamino, 2,4,6-trimethylbenzenesulfonylamino, benzylsulfonylamino, 4-methylbenzylsulfonylamino, trifluoromethylsulfonylamino, phenacylsulfonylamino, methylsulfonylamino, ethylsulfonylamino, 4-fluorobenzenesulfonylamino, benzenesulfinylamino, 2-nitrobenzenesulfinylamino, 2,4-dimethylbenzene sulfinylamino, 4-chlorobenzenesulfinylamino, 4-methoxybenzenesulfinylamino, phenylthioamino, 2,4-dinitrophenylthioamino, triphenylthioamino and 2-nitro-4-methoxyphenylthioamino.

Specific examples of the silylamino group represented by the formula

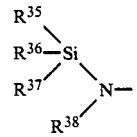

include, among others, trimethylsilylamino, triethylsilylamino, t-butyldimethylsilylamino, t-butyldiphenylsilylamino, isopropyldimethylsilylamino, triphenylsilylamino, triisopropylsilylamino, tribenzylsilylamino, and (triphenylmethyl)dimethylsilylamino.

Specific examples of the group represented by the formula

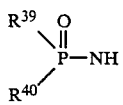

include, among others, dimethylphosphoamino, diethylphosphoamino, diphenylphosphoamino, dibenzylphosphoamino and di-4-chlorophenylphosphoamino.

Specific examples of the group represented by the formula $R^{41}$—CO—CO—NH— includes, among others, methoxalylamino, ethoxalylamino, phenoxalylamino, benzyloxalylamino, pyruvoylamino, ethyloxalylamino, oxamoylamino, benzylaminooxalylamino, thienyloxalylamino, 2-amino-4-thiazolyloxalylamino and ethylaminooxalylamino.

Examples of the organic residues represented by $R^3$, $R^4$, $R^5$, $R^6$ and $R^7$ include those bonded through carbon atom; those bonded through oxygen atom, nitrogen atom or sulfur atom.

Preferable examples of the organic residues bonded through carbon atom include alkyl*, cycloalkyl, alkenyl*, aryl*, acyl, cyano, carbamoyl, heterocyclic ring* or optionally esterified or amidated carboxyl.

Preferable examples of the organic residues bonded through oxygen atom include those represented by the formula; —O—$R^{45}$ [wherein $R^{45}$ stands for hydrogen, alkyl, aryl, acyl, carbamoyl] or oxo group.

Preferable examples of the organic residues bonded through nitrogen include those represented by the formula;

[wherein $R^{46}$ and $R^{47}$ independently stand for hydrogen, alkyl, aryl or acyl].

Preferable examples of the organic residues bonded through sulfur atom include those represented by the formula —S(O)n—$R^{48}$ [wherein $R^{48}$ stands for hydrogen, alkyl*, aryl*, heterocyclic ring* or amino* and n denotes 0, 1 or 2].

Examples of the substituent of the optionally substituted alkyl groups represented by $R^3$, $R^4$, $R^5$, $R^6$ and $R^7$ include hydroxy, acyloxy, carbamoyloxy, amino, dialkylamino, acylamino, alkylthio, heterocyclic thio, carboxy, alkoxy carbonyl, carbamoyl, cyano, azido, aryl and halogen.

Examples of the substituent of the optionally substituted aryl groups represented by $R^3$, $R^4$, $R^5$, $R^6$ and $R^7$ include halogen, alkoxy and alkyl.

Examples of the substituent of the optionally substituted alkenyls represented by $R^3$, $R^4$, $R^5$, $R^6$ and $R^7$ include aryl.

Examples of the groups optionally substituted on the heterocyclic rings represented by $R^3$, $R^4$, $R^5$, $R^6$ and $R^7$ include alkyl.

Examples of the groups optionally substituted on the amino group represented by $R^{48}$ include monoalkyl, dialkyl and monoaryl.

Examples of the optionally esterified carboxyl at $R^3$, $R^4$, $R^5$, $R^6$ and $R^7$ include carboxy and alkyloxycarbonyl.

Examples of the optionally amidated carboxyl represented by $R^3$, $R^4$, $R^5$, $R^6$ and $R^7$ include groups represented by the formula;

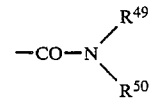

[wherein $R^{49}$ and $R^{50}$ independently stand for hydrogen or alkyl, and they may form a heterocyclic ring together with the adjacent nitrogen atom].

Examples of the above-mentioned alkyl (including alkyls, as substituents, in groups) are preferably those of 1 to 6 carbon atoms.

Preferable examples of the above cycloalkyl are those of 3 to 6 carbon atoms.

Preferable examples of the alkenyl are those of 1 to 4 carbon atoms.

Preferable examples of the acyl (including acyl, as substituents, in groups) are alkyl carbonyl groups of 1 to 6 carbon atoms and aryl carbonyl.

Preferable examples of the alkoxy (including alkoxy in groups) are those of 1 to 6 carbon atoms.

Specific examples of the alkyls of 1 to 6 carbon atoms, the cycloalkyls of 3 to 6 carbon atoms, the alkenyls of 1 to 4 carbon atoms, the alkoxyls of 1 to 6 carbon atoms, aryl, heterocyclic ring (excepting the case when formed together with the adjacent nitrogen atom) and halogen are those as mentioned above regarding the groups represented by $R^1$.

Preferable examples of the heterocyclic rings formed together with the adjacent nitrogen atom are those of 5- to 6-membered ring, which are specifically exemplified by pyrrolyl, pyrrolidinyl, piperidinyl and piperazinyl.

Preferable examples of the groups represented by $R^3$ include methyl, ethyl, isopropyl, vinyl, allyl, cyclopropyl, cyclopentyl, cyclohexyl, phenyl, parachlorophenyl, paramethoxyphenyl, acetyl, propionyl, benzoyl, methoxycarbonyl, ethoxycarbonyl, carbamoyl, dimethylaminocarbonyl, cyano, carboxyl, hydroxymethyl, acetoxymethyl, carbamoyloxymethyl, chloromethyl, methylthiomethyl, 1-methyl-1H-5-tetrazolylthiomethyl, azidomethyl, acetoamidomethyl, cyanomethyl, methoxycarbonylmethyl, hdyroxyethyl, acetoxyhydroxyethyl, carbamoyloxyethyl, chloroethyl, methylthioethyl, 1-methyl-5-tetrazolylthioethyl, cyanoethyl, acetamidoethyl, styryl and phenethyl.

Preferable examples of the groups represented by $R^4$, $R^5$, $R^6$ and $R^7$ include methyl, ethyl, cyclopropyl, cyclopentyl, cyclohexyl, vinyl, allyl, phenyl, parachlorophenyl, paramethoxyphenyl, acetyl, propionyl, benzoyl, cyano, carbamoyl, methoxycarbonyl, dimethylaminocarbonyl, acetoxymethyl, methylthiomethyl, acetamidomethyl, hydroxy, methoxy, ethoxy, acetoxy, phenyloxy, benzoyloxy, carbamoyloxy, methylamino, dimethylamino, phenylamino, acetylamino, methylthio, ethylthio, 2-acetamidoethylthio, 2-N,N-dimethylaminoethylthio, 2-aminoethylthio, 2-hydroxyethylthio, carboxymethylthio, methoxycarbonylmethoxythio, carbamoylmethylthio, phenylthio, 3-pyridazinylthio, 2-pyrimidinylthio, 4-pyridylthio, 1-methyl-1H-5-tetrazolylthio, benzylthio, 4-pyridylmethylthio, sulfamoyl and phenylaminosulfonyl.

Examples of the esters of the end products of this invention are compounds representable by the formula (I) having, at the side chain at the 2- or 10-position, a group represented by the formula; —COOR$^{51}$ [wherein R$^{51}$ stands for alkyl*, alkenyl*, aryl*, cycloalkyl*, hetero cyclic ring* or silyl*].

The groups represented by the above —COOR$^{15}$ are preferably those whose molecular weight is up to 500.

The same meaning and examples of the respective groups of alkyl*, alkenyl*, aryl*, cycloalkyl*, heterocyclic ring* or silyl* represented by R$^{51}$ in the above formula are applied as those given to each corresponding group in respect of R$^1$.

Specific examples of the groups represented by the formula —COOR$^{51}$ include methyl ester, ethyl ester, n-propyl ester, isopropyl ester, t-butyl ester, t-amyl ester, benzyl ester, 4-bromobenzyl ester, 4-nitrobenzyl ester, 2-nitrobenzyl ester, 3,5-dinitrobenzyl ester, 4-methoxybenzyl ester, benzhydryl ester, phenacyl ester, 4-bromophenacyl ester, phenyl ester, 4-nitrophenyl ester, methoxymethyl ester, methoxyethoxymethyl ester, ethoxymethyl ester, benzyloxymethyl ester, acetoxymethyl ester, pivaloyloxymethyl ester, 2-methylsulfonylethyl ester, 2-trimethylsilyethyl ester, methylthiomethyl ester, trityl ester, 2,2,2-trichloroethyl ester, 2-iodoethyl ester, cyclohexyl ester, cyclopentyl ester, allyl ester, cinnamyl ester, 4-picolinyl ester, 2-tetrahydropyranyl ester, 2-tetrahydrofuranyl ester, trimethylsilyl ester, t-butyldimethylsilyl ester, t-butyldiphenylsilyl ester, acetylmethyl ester, 4-nitrobenzoylmethyl ester, 4-mesylbenzoylmethyl ester, phthalimidomethyl ester, propionyloxymethyl ester, 1,1-dimethylpropyl ester, 3-methyl-3-butenyl ester, succinimidomethyl ester, 3,5-di-t-butyl-4-hydroxybenzyl ester, mesylmethyl ester, benzenesulfonylmethyl ester, phenylthiomethyl ester, iminomethylaminoethyl ester, 1-iminoethylaminoethyl ester, dimethylaminoethyl ester, pyridine-1-oxido-2-methyl ester, methyl-sulfinylmethyl ester, bis-(4-methoxyphenyl)methyl ester, 2-cyano-1,1-dimethyl ethyl ester, t-butyloxycarbonylmethyl ester, benzoylaminomethyl ester, 1-acetoxyethyl ester, 1-isobutyryloxyethyl ester, 1-ethoxycarbonyloxyethyl ester, phthalide ester, 4-t-butylbenzyl ester, 5-indanyl ester, 5-methyl-2-oxo-1,3-dioxolen-4-yl-methyl ester and 5-t-butyl-2-oxo-1,3-dioxolen-4-yl-methyl ester.

This invention includes not only the esters described above, but also pharmaceutically acceptable esters which are able to be converted into the Compound (I) in the organism. As the esters applicable as metabolically unstable, nontoxic esters which can be converted into the Compound (I) in the organism, there may be mentioned, for example, the esters mentioned above with reference to —COOR$^{44}$.

The compounds of this invention may be used in the free state in respect of the carboxyl group in the 2- or 10-position, while they can also be used in the form of a pharmacologically acceptable salt prepared by conventional means. Examples of such salts includes those with a non-toxic cation such as sodium, potassium, etc., those with a basic amino acid such as arginine, ornithine, histidine, etc.; and those with polyhydroxyalkylamine such as N-methyl glucamine, diethanolamine, triethanolamine, tris-hydroxymethylaminomethane, etc. When R$^1$ and/or R$^{3-7}$ contains a basic group (e.g. amino group), salts with an organic acid such as acetic acid, tartaric acid or methanesulfonic acid; salts with an inorganic acid such as hydrochloric acid, hydrobromic acid, sulfuric acid or phosphoric acid; salts with an acidic amino acid such as arginine, aspartic acid or glutamic acid; etc. may be used, among others.

The compounds of the present invention can react with a base to form a salt. As examples of so formed salts, mention may be made of salts formed with an inorganic base such as sodium, potassium, lithium, calcium, magnesium or ammonium salt; and salts formed with an organic base such as pyridine, collidine, triethylamine or triethanolamine.

Among the Compounds(I), particularly preferred are the compounds represented by the formula:

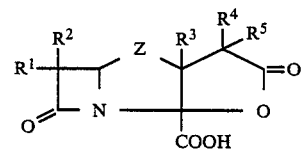

wherein R$^1$ represents an amino group or an acylamino group wherein the acyl moiety is derived from a carboxylic acid; R$^2$ represents hydrogen, a methoxy group or a formylamino group; R$^3$, R$^4$ and R$^5$ independently represent hydrogen atom or an alkyl group and Z represents a group represented by the formula —S—CH$_2$— or —CH$_2$—S—, their esters or their salts.

Furthermore, among said compounds, the compounds wherein R$^1$ is an acylamino group of the formula:

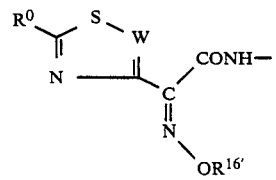

wherein R$^0$ is an amino group which may be protected, R$^{16'}$ is a hydrogen atom or an alkyl group which may have one to three substituents each selected from the class consisting of halogen, amino group, hydroxy group and carboxy group which may be protected, and W is —N= or —CH=.

Description of the method of producing the object compounds of this invention is as follows:

The object compound of this invention, the compound having 4,11-dioxo-3-oxa-8(or 7)-thia-1-azatricyclo[7,2,0,0$^{2,6}$]undecane-2-carboxylic acid skeleton, or an ester thereof or a salt thereof can be obtained by subjecting to a ring closure reaction a compound having 2-oxo-3-(2-azetidinon-4-yl)thiomethyl(or methylthio)-glutaric acid skeleton or an ester thereof or a compound having 3-(2-azetidinon-4-yl)thiomethyl(or methylthio)-5-oxo-tetrahydrofuran-2-carboxylic acid skeleton having a leaving group at the 2-position, or an ester thereof.

More specifically, among the object compounds of this invention, a compound representable by the general formula;

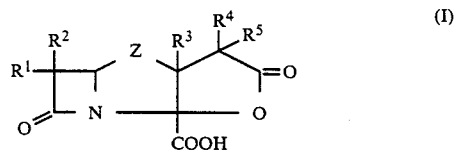 (I)

[wherein $R^1$, $R^2$, $R^3$, $R^4$, $R^5$ and Z are of the same meaning as specified above], or an ester thereof or a salt thereof can be produced by subjecting a compound representable by the formula;

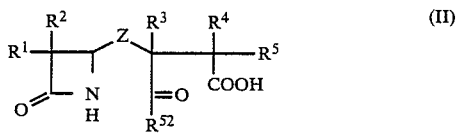

[wherein $R^{1'}$ stands for an organic residue bonded through nitrogen, $R^{52}$ stands for a group derivable from carboxyl group, and $R^2$, $R^3$, $R^4$, $R^5$ and Z are of the same meaning as defined above] or a compound representable by the formula

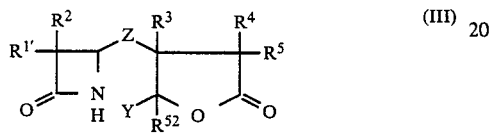

[wherein Y stands for a leaving group, and $R^{1'}$, $R^2$, $R^3$, $R^4$, $R^5$, $R^{52}$ and Z are of the same meaning as defined above] to a ring closure reaction to give a compound (I') representable by the formula

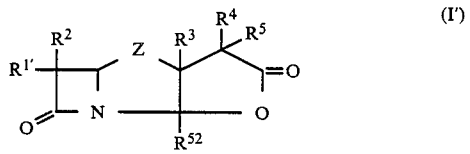

[wherein $R^{1'}$, $R^2$, $R^3$, $R^4$, $R^5$, $R^{52}$ and Z are of the same meaning as defined above], followed by, when desired, subjecting the R' and/or $R^{52}$ of the compound (I') to modification.

The explanation and examples of $R^{1'}$ in the above formula are those applied for the above-mentioned $R^1$ when it stands for an organic residue bonded through N.

Needless to say, the Compounds (I'), which fall within the scope of the Compounds (I), constitute the desired compounds of the present invention.

Examples of the groups derivable from the carboxyl group represented by R include those representable by the formula; —COOR$^{51'}$ [wherein R$^{51'}$ stands for alkyl*, alkenyl*, aryl*, cycloalkyl*, heterocyclic ring* or silyl*] and those representable by the formula;

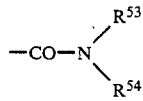

[wherein $R^{53}$ and $R^{54}$ independently stand for hydrogen, alkyl*, aryl*, cycloalkyl*, alkenyl* or heterocyclic ring*, including the case when $R^{53}$ and $R^{54}$ form heterocyclic ring* together with the adjacent nitrogen atom].

The groups derivable from carboxyl group, shown by $R^{52}$ in the above formula are preferably those having a molecular weight of not more than 500.

To further details of the groups represented by —COOR$^{51'}$, the explanation and examples given above as to —COOR$^{51}$ can be applied as they are.

Specific examples of the groups represented by the formula

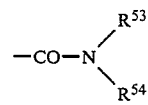

include dimethylamido, diethylamido, dipropylamido, dibenzylamido, dicyclohexylamido, N-benzyl-N-methylamido, N-phenyl-N-methylamido, pyrrolidinamido, piperidinamido, piperazinamido, morpholinamido, carboxymethylamido, 1-carboxyethylamido, etc.

In the above formula, the leaving group represented by Y includes any one so long as it can be substituted with the nitrogen at the NH group of β-lactam ring of the Compound (III) and form a C—N bond which is exemplified by halogen (such as bromine, chlorine), sulfonyloxy (specifically exemplified by p-toluenesulfonyloxy, p-nitrophenylsulfonyloxy, p-nitrophenylsulfonyloxy, methanesulfonyloxy) having a substituent [e.g. alkyl aryl (exemplified by such ones as those mentioned above in respect of $R^1$ as alkyl, aryl)], disubstituted phosphoryloxy (e.g. diphenylphosphoryloxy, diethylphosphoryloxy), etc.

The reaction from the Compound (II) to the Compound (I') is preferably carried out in the presence of a condensing agent, a C-terminal activating agent, an acid or a Lewis acid.

The above reaction is carried out desirably in a solvent. The said C-terminal activating agent means a reagent capable of converting carboxylic acid into a reactive derivative in the peptide linkage formation in the field of peptides or in the acylation of amino groups of β-lactams.

Specific examples of the condensing agent to be used herein include N,N'-dicyclohexylcarbodiimide (hereinafter-sometimes abbreviated as DCC), combination of DCC with N-hydroxysuccinimide or 1-hydroxybenzotriazole; 1-ethyl-3-[3-(dimethylamino)propyl]carbodiimido (hereinafter sometimes abbreviated as WSC); carbonyldiimidazole; N-ethyl-5-isoxazolium-3'-sulfonate; 2-ethyl-7-hydroxybenzisoxazolium trifluoroborate; 1-ethoxycarbonyl-2-ethoxy-1,2-dihydroquinoline; comination of 2,2'-dipyridyldisulfide with triphenylphosphine; combination of carbon tetrachloride with triphenylphosphine; 2-halogen pyridinium salt such as 2-chloro-1-methyl-pyridinium iodide or 2-fluoro-1-methylpyridinium tosylate, etc., pyrimidinium salt such as 2-chloro-1-methyl pyrimidinium fluorosulfate, etc. onium salts of azalene such as 2-chloro-3-ethyl-benzoxazolium tetrafluoroborate, 2-fluoro-3-methyl-benzothiazolium fluorosulfate, etc. [cf.: Angewandte Chemie, International Edition, 18, 707 (1979)].

The above-mentioned reactive derivatives of carboxylic acid are exemplified by acid halides such as acid chloride, acid bromide, etc.; acid azide; mixed acid anhydrides with carbonic acid monoalkyl ester, mixed acid anhydrides with aliphatic carboxylic acid such as acetic acid, pivalic acid, valeric acid, isovaleric acid, trichloroacetic acid, etc., mixed acid anhydrides with acids such as phosphoric acid (e.g. diphenyl phosphoric acid, diethyl phosphoric acid, etc.) and sulfuric acid, etc., mixed anhydrides with, for example benzoic acid, etc., symmetric acid anhydrides amido compounds having acyl group bonded through nitrogen in the ring such as pyrazole, imidazole, 4-substituted imidazole, dimethylpyrazole, benzotriazole, thiazolidine-2-thione, etc.; active esters with, for example, 4-nitrophenyl, 2,4-dinitrophenyl, pentachlorophenyl, pentafluorophenyl, cyanomethyl, N-hydroxysuccinimide, N-hydroxyphthalimide, etc.; active thioesters with heterocyclic thiol such as 2-pyridyl thiol, 2-benzthiazolyl thiol, etc.

As the C-terminal activating agent to convert carboxylic acid into these reactive derivatives, there are employed, for example, the reagents disclosed in "Peptide Synthesis" authored by Nobuo IZUMIYA, Motonori OHNO and Haruhiko AOYAGI, pp. 117 to 153, published in 1975, by MARUZEN Co., Ltd. (Japan). More specific examples of these activating agents include thionyl chloride, thionyl bromide, sulfuryl chloride, phosphorus oxychloride, oxalylchloride, halogenating agents such as chlorine, bromine and combination of carbon tetrachloride and triphenylphosphine, etc. sulfonylating agents such as anhydrous p-toluenesulfonic acid, anhydrous p-nitrobenzene sulfonic acid, anhydrous 2,4,6-triisopropylphenylsulfonic acid, anhydrous methane sulfonic acid, p-toluene sulfonylchloride, etc., phosphorylating agents such as diphenyl phosphoric acid chloride, dimethyl phosphoric acid chloride, diethyl phosphoric acid chloride, etc.

The acid employable for this reaction is exemplified by hydrochloric acid, sulfuric acid, trifluoroacetic acid, methanesulfonic acid, camphor sulfonic acid, etc.

The Lewis acid employed for this reaction is exemplified by boron trifluoride etherate, zinc chloride, tin tetrachloride, aluminium chloride, titanium tetrachloride, boron trichloride, etc.

Any solvent which does not exert influences upon the reaction can be employed, which is exemplified by conventional solvents such as dichloromethane, chloroform, tetrahydrofuran, dioxane, diethylether, ethyl acetate, benzene, toluene, n-hexane, acetonitrile, dimethylformamide, etc.

This reaction may be conducted in the presence of a base. Thus, for example, where there is employed as the condensing agent 2-chloro-1-methyl pyridinium iodide, 2,2'-dipyridyldisulfide-triphenylphosphine, carbon tetrachloride—triphenylphosphine, etc., the base is exemplified by an organic base of triethylamine, diisopropylethylamine, N-methyl morpholine, 3,4-dihydro-2H-pyrido[1,2-a]pyrimidin-2-one, and an inorganic base such as sodium hydrogencarbonate. Among them, 3,4-dihydro-2H-pyrido[1,2-a]pyrimidin-2-one is preferable. Besides, the reaction may be conducted in the presence of for example silver chloride, silver tetrafluoroborate, silver perchlorate, etc. (for example, in the case of using as the condensing agent, for example, 2,2'-dipyridyldisulfidetriphenylphosphine).

The reaction temperature is not limitative so long as the reaction proceeds, but, the reaction is conducted usually in the range of from about $-50°$ C. to 150° C., preferably from about $-10°$ C. to 100° C. The reaction time varies with the kinds of starting materials, reagent and solvents and reaction temperature, but it usually ranges from about 5 minutes to 30 hours.

Incidentally, in case of conducting the condensation by employing a Lewis acid as the catalyst, a dehydrating agent such as molecular sieves may optionally be allowed to exist in the reaction system.

Alternatively, the Compound (I) can be produced by subjecting the Compound (III) to a ring closure reaction to give the Compound (I'), followed by, when desired, subjecting the $R^{1'}$ and/or $R^{52}$ thereof to modification.

The reaction of converting the Compound (III) to the Compound (I') is usually conducted by treating the former with a base, preferably in a solvent. As the base, use is made of, for example, organic amines such as triethylamine, tripropylamine, tri-n-butylamine, diisopropylethylamine, triethylenediamine, 1,4-diazabicyclo[2,2,2]octane (hereinafter sometimes abbreviated as DABCO), 1,8-diazabicyclo[5,4,0]-7-undecene (hereinafter sometimes abbreviated as DBU), N-methylmorpholine, N-methylpiperidine, N-methylpyrrolidine, 3,4-dihydro-2H-pyrido[1,2-a]pyrimdin-2-one, 4-dimethylaminopyridine, pyridine, lutidine, γ-colidine, etc., alkali metals such as lithium, sodium, potassium, cesium, etc., alkaline earth metals such as magnesium, calcium, etc., or hydrides, hydroxides, carbonates or alcoholates thereof. As the solvent, use is made of conventional solvents such as dichloromethane, chloroform, tetrahydrofuran, dioxane, benzene, toluene, acetonitrile, dimethylacetamide, dimethylformamide, etc. Among the abovementioned bases, liquid ones can be used also as the solvent. In this invention, the base is usually employed in an amount of about equivalent relative to the Compound (III), but may be used in an excess amount so long as it does not hamper the reaction. The reaction temperature usually ranges from about $-20°$ C. to 100° C., and the reaction time usually ranges from about 5 minutes to 30 hours.

Thus obtained Compound (I') is, upon necessity, further subjected to modification of $R^{1'}$ and $R^{52}$ to produce the Compound (I) or its ester or salt. The conversion reaction is exemplified by acyl-cleavage reaction by means of iminoether method, deprotection reaction, acylation, ureido formation (thioureido formation) alkylation, alkenylation, thioation, silylation, phosphorylation, esterification, amidation, etc.

The acyl-cleavage reaction by means of iminoether method is performed by at first allowing, for example, phosphorus pentachloride, phosgene, phosphorus trichloride or phosphorus oxychloride to react with a compound (I') wherein $R^{1'}$ stands for

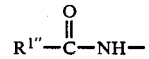

[wherein

stands for the moiety other than —NH— in the organic residue bonded through nitrogen] to produce the corresponding imino chloride. The above chloride reagent is used in an amount of about 1 to 5 equivalents, more preferably about 1.5 to 3 equivalents. The reaction is conducted conveniently in the presence of a solvent such as methylene chloride, dichloroethane, chloroform, carbon tetrachloride, trichloroethane, etc. For accelerating the reaction, it is preferable to use, for example, pyridine, N,N-dimethylaniline, triethylamine, aniline, toluidine, etc. in an excess amount, for example, about 3 to 20 equivalents, more preferably, about 5 to 10 equivalents.

The said reaction is conducted preferably at temperatures ranging from about −30° C. to 0° C., more preferably from −15° C. to −5° C. for about 15 minutes to 8 hours, more preferably about 30 minutes to 2 hours. It is convenient to conduct the reaction under stirring.

For converting the iminochloride produced as an intermediate to iminoether, an excess amount of methanol is added to the reaction solution, then the mixture is stirred at about −30° C. to 0° C., preferably about −15° C. to −5° C. for about 15 minutes to 2 hours, preferably about 30 minutes to 1 hour, followed by, for completing the reaction, stirring at about 10° C. to 40° C., preferably about 20° C. to 30° C. for about 30 minutes to 2 hours. Then, dilute hydrochloric acid is added to the reaction solution to thereby cleave the C—N linkage. The reaction temperature is in the range of from about 10° C. to 40° C., preferably about 20° C. to 30° C., and the reaction time ranges from about 15 minutes to 2 hours, preferably about 30 minutes to 1 hour.

The reaction solution thus obtained is neutralized with for example sodium hydrogencarbonate, and the reaction product is obtained by extraction with a water-immiscible organic solvent such as methylene chloride, diethyl ether, ethyl acetate, etc. That is, these three successive reactions or the acyl-cleavage can be carried out according to the conventional manner.

The deprotection reaction can be also carried out according to the conventional manner and, any one can be suitably selected from conventional means for example, those using an acid, those using a base, those using hydrazine, those by reduction, among others, depending on the kinds of protective groups. In the case of means using an acid, while varying with the kinds of protective groups or any other reaction conditions, use is made of, for example, an inorganic acid such as hydrochloric acid, sulfuric acid, phosphoric acid, etc., an organic acid such as formic acid, acetic acid, trifluoroacetic acid, propionic acid, etc., and, besides, acidic ion-exchange resin, etc. In the case of means using a base, while varying with the kinds of protective groups or any other conditions, use is made of, for example, inorganic bases such as hydroxides, carbonates, etc. of alkali metal such as sodium, potassium, etc. or alkaline earth metal such as calcium, magnesium etc., organic bases such as metal alkoxides, organic amines, quaternary ammonium salts, etc., and, besides, basic ion-exchange resin, etc. In the case of means using the above-mentioned acid or base, when a solvent is used, use is made of, in many cases, a hydrophilic organic solvent, water or a mixture solvent.

In the case of means using reduction, while varying with the kinds of protective groups or any other conditions, use is made of, for example, means using a metal such as tin, zinc, etc. or a metal compound such as chromium dichloride, chromium acetate, etc. in combination with an organic or inorganic acid such as acetic acid, propionic acid, hydrochloric acid, etc., and means of reducing in the presence of a metal catalyst useful for catalytic reduction. As the catalyst, use is made of, for example, a platinum catalyst such as platinum wire, platinum sponge, platinum black, platinum oxide, colloidal platinum, etc., a palladium catalyst such as palladium sponge, palladium black, palladium oxide, palladium barium sulfate, palladium barium carbonate, palladium carbon, palladium silica gel, colloidal palladium, etc., reduced nickel, nickel oxide, Raney nickel, Uru-shibara nickel, etc. In the case of reduction using a metal and an acid, use is made of a metal such as iron, chromium, etc. and an inorganic acid such as hydrochloric acid, etc. or an organic acid such as formic acid, acetic acid, propionic acid, etc. The method using reduction is conducted usually in a solvent. In the case of catalytic reduction, for example, use is often made of alcohols such as methanol, ethanol, propyl alcohol, isopropyl alcohol, etc., ethyl acetate, etc. In the method of using a metal and an acid, water, acetone, etc. are often used, and when the acid is a liquid one, the acid itself can be used as the solvent as well. Reaction temperatures in the method of using an acid, that using a base and that resorting to reduction usually range from those under cooling to those under warming.

For removing the protective group in each group of the compound thus obtained, the same processes as mentioned above can be carried out. In short, the deprotection reaction can be conducted by per se conventional means.

For example, by subjecting the Compound (I') [wherein $R^{1'}$ is a protected amino and $R^{52}$ is a group of the formula —$COOR^{51'}$ ($R^{52}$ and $R^{51'}$ are as defined above)] to deprotection reaction for the amino protective group in the $R^{1'}$ at the 10 position, the ester compound at the 2 position of the Compound (I) wherein $R^1$ is an amino group [which may be hereinafter referred to as Compound (I-1)] can be obtained. For example, by subjecting the Compound (I') [wherein $R^1$ is an organic residue bonded via nitrogen and $R^{52}$ is a group of the formula —$COOR^{51'}$] to deprotection reaction for the group $R^{51'}$, Compound (I) wherein R' is an organic residue bonded via nitrogen [which may be hereinafter referred to as Compound (I-2)] can be obtained. For example, by subjecting Compound (I-1) or Compound (I-2) to further deprotection for the group represented by $R^{51'}$ or for the amino protective group at the 10-position respectively, Compound (I) wherein $R^1$ is an amino group [which may be hereinafter referred to as Compound (I-3)] can be obtained. Alternatively, by subjecting the Compound (I') wherein $R^{1'}$ is a protected amino and $R^{52}$ is a group of the formula —$COOR^{51'}$ to deprotection reaction for both of the amino-protective group at the 10 position and the group represented by $R^{51'}$, Compound (I-3) can be obtained in one step.

The Compound (I-1) can also be converted to the Compound (I-2) by subjecting the former to a reaction, for example, acylation, ureido formation (thioureido formation), alkylation, alkenylation, thionation, silylation or phophorylation for the organic residue bonded via nitrogen at the 10 position. Detailed description of these reactions is as follows.

Acylation of the amino group can be carried out by allowing a starting compound to react with an acylating agent containing the acyl group in the group $R^1$, such as a reactive derivative of carboxylic acid, in a solvent. As the reactive derivative of carboxylic acid, use is made of, for example, acid halides, acid anhydrides, active amide compounds, active esters or active thioesters. Specific examples of these reactive derivatives are set forth as follows.

(1) Acid halides:

Acid halides employable herein are exemplified by acid chlorides and acid bromides.

(2) Acid anhydrides:

Acid anhydrides employable herein are exemplified by monoalkyl carbonic acid mixed anhydrides, mixed acid anhydrides comprising aliphatic carboxylic acids (e.g. acetic acid, pivalic acid, valeric acid, isovaleric acid, trichloroacetic acid, etc.), mixed acid anhydrides comprising aromatic carboxylic acids (e.g. benzoic acid, etc.) or symmetric acid anhydrides.

(3) Amide compounds:

Amide compounds employable herein are exemplified by compounds having an acyl group bonded to the nitrogen in the ring, such as pyrazole, imidazole, 4-substituted imidazole, dimethylpyrazole benzothiazole or benzotiriazole.

(4) Active esters:

Active esters employable herein are exemplified by esters such as methyl esters, ethyl esters, methoxymethyl esters, propargyl esters, 4-nitrophenyl esters, trichlorophenyl esters, pentachlorophenyl esters, mesylphenyl esters, and benzotriazolyl esters, as well as esters formed with 1-hydroxy-1H-2-pyridone, N-hydroxysuccinimide, N-hydroxyphthalimide, etc.

(5) Active thioesters:

Active thioesters employable herein are exemplified, among others, by thioesters formed with heterocyclic thiols such as 2-pyridylthiol, 2-benzthiazolylthiol, etc.

From among various reactive derivatives as described above, suitable ones can be properly selected depending on the type of carboxylic acid.

This reaction is preferably carried out in the presence of a base in case when a reactive derivative used. As the base, use is made of, for example, aliphatic tertiary amines (e.g. trimethylamine, triethylamine, tripropylamine, tri-n-butylamine, etc.), tertiary amines such as N-methylpiperidine, N-methylpyrrolidine, cyclohexyldimethylamine, N-methylmorpholine, etc., dialkylamines such as di-n-butylamine, idobutylamine, dicyclohexylamine, etc., aromatic amines such as pyridine, lutidine, γ-collidine, etc., hydroxides or carbonates of alkali metals such as lithium, sodium, potassium, etc., or of alkaline earth metals such as calcium, magnesium etc.

In this procedure, the reactive derivative of the carboxylic acid is normally used in an equivalent to the Compound (I-1), but it may also be used in excess, so long as it does not interfere with the reaction. When a base is used, the amount of such a base to be used is normally in the range of from about 1 to 30 equivalents, preferably about 1 to 10 equivalents, while varying with the types of the reactive derivatives of carboxylic acid. This reaction is usually conducted in a solvent, as exemplified by conventional organic solvents singly or in combination, for example, ethers such as dioxane, tetrahydrofuran, diethyl ether, diisopropyl ether, propylene oxide, butylene oxide, etc., esters such as ethyl acetate, ethyl formate, etc., halogenated hydrocarbons such as chloroform, dichloromethane, 1,2-dichloroethane, 1,1,1-trichloroethane, etc., hydrocarbons such as benzene, toluene, n-hexane, etc., amides such as N,N-dimethylforamide, N,N-dimethylacetamide, etc., nitriles such as acetonitriles, etc. Of the above-mentioned base, liquid ones can also be used for the dual purposes of base and solvent. Reaction temperatures are not specifically limited, as long as the reaction proceeds, but the reaciton is carried out usually at −50° C. to 150° C., preferably −30° C. to 80° C. The reaction usually completes itself within ten minutes to three days, while varying with the starting material, the base, the reaction temperature and the solvent, though, in some instances, it requires ten days.

The reaction of converting the amino group into the uriedo or thioureido group is carried out by, for example, allowing a substituted isocyanate or substituted isothiocyanate representable by the formula; $R^{24}-N=C=A$ (wherein $R^{24}$ and A are of the same meaning as defined above) to react with a starting compound in the presence of a solvent. The substituted isocyanate includes, for example, methyl isocyanate, ethyl isocyanate, phenyl isocyanate, p-bromomophenyl isocyanate, etc., and the substituted isothiocyanate includes, for example, methyl isothiocyanate, phenyl isothiocyanate, etc. In this reaction, the substituted isocyanate or substituted isothiocyanate is normally used in an about equivalent to the Compound (I-1), but it can also be used in excess, unless it adversely affects the reaction. Examples of the solvent include, among others, tetrahydrofuran, diethyl ether, ethyl acetate, chloroform, dichloromethane or toluene. The reaction temperature ranges from about −20° C. to about 50° C., and the reaction time is usually in the range of from about 10 minutes to about 5 hours.

The reaction for introducing an alkyl group, as a group bonded through carbon to the nitrogen, into the amino group at its 10 position of the Compound (I-1) is described below as alkylation.

Alkylation of the Compound (I-1) can be conducted by allowing an alkylating agent containing a group corresponding to the group bonded to the nitrogen through carbon in the group $R^1$ to act on the Compound (I-1). Examples of the alkylating agent includes, for example, halogenated alkyl compounds such as propyl chloride, butyl chloride, benzyl chloride, butyl bromide, benzyl bromide, allyl bromide, methyl iodide, ethyl iodide, propyl iodide, etc., dialkyl sulfate compounds such as dimethyl sulfate, diethyl sulfate, etc., substituted sulfonate compounds such as methyl mesylate, ethyl mesylate, methyl tosylate, ethyl tosylate, etc., dihalogenated alkyl compounds (e.g. 1,5-dichloropentane, 1,4-dichlorobutane, etc.), etc. This reaction is normally conducted in a solvent, and examples of the solvent include water, methanol, ethanol, benzyl alcohol, benzene, N,N-dimethylformamide, tetrahydrufuran, acetonitrile, etc. The reaction temperature ranges from about 20° C. to 200° C., and the reaction time is in the range of from about 30 minutes to 50 hours. This reaction, by changing the reaction conditions, such as a molar ratio of the Compound (I-1) to the alkylating agent, permits selective production of a secondary amine, tertiary amine or quaternary ammonium compound. It is also possible to introduce different substituent groups into the nitrogen, by conducting the reaction stepwise. The reaction of introducing a group bonded to the nitrogen through carbon other than alkyl groups can be conducted in a manner analogous to the above.

Alternatively, the alkylation can also be conducted by reacting the Compound (I-1) with a carbonyl compound in the presence of a reducing agent. Examples of the reducing agent which is useful in this reaction include lithium aluminium hydride, sodium cyanoborohydride, sodium borohydride, sodium, sodium amalgam, combinations of zinc with acids, among others. Also, the alkylation reaction can be carried out through catalytic reduction using for example palladium, platinum, rhodium or the like as a catalyst.

The reaction of converting the amino group to a group represented by the formula $R^{26}-NH-$ (e.g. imino-substituted alkylamino, alkylimino-substituted alkylamino or substituted guanidino group):

The reaction of converting the amino group to an iminosubstituted alkylamino or alkylamino-substituted alkylamino is carried out by allowing the starting compound to react with, for example, an imide ester in a solvent such as dioxane, tetrahydrofuran, N,N-dimethylformamide, chloroform, acetone, acetonitrile or water. Preferable imide esters are exemplified by methyl formimidate, ethyl formimidate, benzyl formimidate, methyl acetoimidate, ethyl acetoimidate, methylphenyl acetoimidate, ethyl N-methylformimidate, methyl N-isopropylformimidate, etc. The reaction temperature is in the neighborhood of from 0° C. to 25° C., while the reaction time ranges normally from about 1 hour to about 6 hours. The reaction of converting the amino group to guanidino group is conducted by allowing the starting compound to react with, for example, O-alkyl- or O-aryl pseudourea or S-alkyl- or S-aryl pseudothiourea in a solvent such as water, N,N-dimethylformamide or hexamethylene phosphoramide. As the above-mentioned pseudoureas, use is made of O-methylpseudourea, S-methyl pseudourea, O-2,4-dichlorophenyl pseudourea or O-N,N-trimethyl pseudourea, for example, and as the above-mentioned pseudothioureas, use is made of S-p-nitrophenyl pseudothiourea, for example. The reaction temperature is in the neighborhood of from 0° C. to 40° C., while the reaction time ranges normally from about 1 hour to 24 hours.

Alkenylation (imination) of the Compound (I-1) can be carried out by subjecting the Compound (I-1) to dehydrative condensation with a carbonyl compound (e.g. propionaldehyde, diethyl ketone). The reaction can be conducted in a solvent, while it proceeds in the absence of solvent. An acid or a base may be employed as a catalyst. The desired compound can also be produced by heating the Compound (I-1) and a carbonyl compound under reflux in the presence of a dehydrating agent or by using a dehydration apparatus such as a Dean and Stark apparatus. Examples of the solvent usable for this reaction include benzene, toluene, dichloromethane, ethanol, etc. The reaction temperature ranges from about 0° C. to 200° C., while the reaction time is in the range of from about 1 hour to 20 hours. Examples of the acid usable as a catalyst include benzenesulfonic acid, methanesulfonic acid, sulfuric acid, boron trifluoride, zinc chloride, etc., while those of the base include potassium hydroxide, sodium carbonate, etc. The dehydrating agent usable for this reaction is exemplified by molecular sieves, silica gel, anhydrous magnesium sulfate, anhdyrous sodium sulfate, etc.

The thionation of the Compound (I-1) is normally carried out by allowing the Compound (I-1) to react with a halogenated thio compound represented by the formulal $R^{34}$—SOn—X (wherein X stands for a halogen e.g. chlorine, bromine, etc., and $R^{34}$ and n are of the same meaning as defined above) (e.g. halogenated sulfonyl, halogenated sulfinyl, halogenated sulfenyl) in a solvent in the presence of a base. Examples of the solvent usable for this reaction include water, acetone, dioxane, N,N-dimethylformamide, benzene, tetrahydrofuran, dichloromethane and an optional mixture of them. As the base, use is made of, for example an organic base such as pyridine, picoline, triethylamine, N-methylmorpholine, etc. or an inorganic base such as sodium hydroxide, potassium hydroxide, sodium carbonate, sodium hydrogencarbonate, potassium carbonate, etc. This reaction normally requires about 1 equivalent of the halogenated thio compound and about 1 to 10 equivalent of the base to be used against the Compound (I-1). The reaction temperature ranges from about −20° C. to 80° C., and the reaction time is in the range of from 15 minutes to 10 hours.

This reaction is also conducted using a thioacid anhydride e.g. toluenesulfonic anhydride, trifluoromethanesulfonic anhydride, etc.) in place of the halogenated thio compound. Also, this reaction can be carried out by allowing the starting compound to react with a thionating agent such as N-sulfonyl-N-methylpyrrolidinium, N-sulfonylimidazolide or N-sulfonyl-1H-1,2,4-triazolide.

The silylation of the Compound (I-1) can be normally carried out by allowing the Compound (I-1) to react with a halogenated silyl compound (e.g. silyl chloride compounds, silyl bromide compounds) represented by the formula;

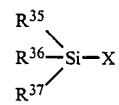

or $R^{38'}$—X (wherein $R^{35-37}$ are of the same meaning as defined above, $R^{38'}$ stands for silyl* which may have substituents such as those mentioned above for silyl* with respect to $R^1$, and X stands for halogen) in the presence of a base. The base is exemplified by an organic base such as pyridine, picoline, triethylamine, diisopropylethylamine, N-methylmorpholine, etc. The reaction is preferably conducted in a solvent which is exemplified by acetone, dioxane, N,N-dimethylformamide, benzene, tetrahydrofuran, dichloromethane, etc. The reaction temperature ranges from about −20° C. to the boiling point of the solvent then used, or from about −20° C. to 80° C., and the reaction time is in the range of from about 15 minutes to 20 hours.

The phosphorylation of the Compound (I-1) is normally carried out by allowing the Compound (I-1) and about an equivalent of a phosphoryl halide e.g. a phosphoryl chloride (e.g. dimethylphosphoryl chloride, diethylphosphoryl chloride, diphenylphosphoryl chloride, dibenzylphosphoryl chloride, etc.) represented by the formula;

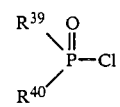

(wherein $R^{39}$ and $R^{40}$ are of the same meaning as defined above) to react with about an equivalent or excess amount of a base in a solvent. As the base, use is made of an organic base such as pyridine, picoline, triethylamine, N-methylmorpholine, etc., or an inorganic base such as sodium hydroxide, potassium hydroxide, sodium hydrogencarbonate, sodium carbonate, etc. As the solvent, use is made of, for example, water, acetone, acetonitrile, dioxane, N,N-dimethylformamide, tetrahydrofuran, dichloromethane or an optional mixture of them. The reaction temperature ranges from about −20° C. to 80° C., and the reaction time is in the range of from 15 minutes to 15 hours.

The Compound (I-3) can be converted to the Compound (I-2) by subjecting the former to acylation, ureido formation (thioureido formation), alkylation, alkenylation, thionation, silylation, phosphorylation, etc. The conversion reaction can be carried out in a manner similar to the above-mentioned conversion reaction of the Compound (I-1) to the Compound (I-2).

Further, the Compound (I-2) can also be converted to the Compound (I') or (I-1) by subjecting to esterification of the carboxylic group at the 2-position of compound (I-2) or amidation of the same carboxylic group. Description of these reactions is as follows.

The esterification is carried out by, for example, the following procedures.

(1) The starting compound is allowed to react with diazoalkane, e.g. diazomethane, phenyldiazomethane, diphenyldiazomethane or the like, in a solvent such as tetrahydrofuran, dioxane, ethyl acetate or acetonitrile at a temperature ranging from about 0° C. to the refluxing temperature for a period ranging from about 2 minutes to 2 hours.

(2) An alkali metal salt of the starting compound is allowed to react with an activated alkyl halide such as methyl iodide, benzyl bromide, p-nitro-benzyl bromide, m-phenoxybenzyl bromide, p-t-butylbenzyl bromide, pivaloyloxymethyl bromide or the like. This reaction is preferably carried out in a solvent such as N,N-dimethylformamide, N,N-dimethylacetamide, hexamethylphosphoramide or the like at temperatures ranging from about 0° C. to 60° C. for a period ranging from about 2 minutes to 4 hours. Coexistence of, for example, triethylamine in this reaction mixture does not affect adversely the reaction.

(3) The starting compound is allowed to react with an alcohol represented by the formula; $R^{51}$—OH or $R^{51'}$—OH [wherein $R^{51}$ and $R^{51'}$ are of the same meaning as defined above], such as methanol, ethanol, benzyl alcohol or the like. This reaction is carried out in the presence of a carbodiimide condensing agent such as DCC or the like at temperatures ranging from about 0° C. to the refluxing temperature for a period ranging from about 15 minutes to 18 hours. As the solvent, use is made of, for example, chloroform, dichloromethane, dichloroethane, etc.

(4) An acid anhydride of the starting compound (I-2), which is obtained by allowing the starting compound to react with, for example, ethyl chlorocarbonate, benzyl chlorocarbonate or the like, is allowed to react with an alcohol, for example those mentioned in (3) under the reaction conditions as described in (3) above, namely, in a solvent such as tetrahydrofuran, dichloromethane or the like at temperatures ranging from 25° C. to the refluxing temperature for a period ranging from about 15 minutes to 10 hours.

(5) The starting compound is allowed to react with a silylating agent such as trimethylsilyl chloride or t-butyl-dimethylsilyl chloride in the coexistence of triethylamine or the like in a solvent e.g. dichloromethane, chloroform, tetrahydrofuran, etc. at temperatures ranging from about 0° C. to the refluxing temperature for a period ranging from about 15 minutes to 16 hours.

The amidation of carboxylic group is carried out by synthesizing an acid anhydride of the starting compound (I-2) from the starting compound (I-2) and an acid chloride such as ethyl chlorocarbonate, benzyl chlorocarbonate or pivalic chloride, or an acid anhydride such as acetic anhydride, trifluoro-acetic anhydride or the like according to the per se known method, the acid anhydride being then allowed to react with ammonia or a selected amine, for example, the above-mentioned alkyl-, dialkyl aralkyl- or heterocyclic amines. Or, the amidation is also conducted by allowing carboxylic acid to react with any of the above-mentioned amines in the presence of a condensing agent such as DCC, N-3-dimethylaminopropyl-N-ethyl carbodiimide or the like.

The above reaction is carried out in a solvent such as dichloromethane, tetrahydrofuran, N,N-dimethylformamide or the like at temperatures ranging from 0° C. to the refluxing temperature for a period ranging from 15 minutes to 16 hours.

The Compound (I), wherein $R^2$ stands for methoxy, can also be prepared by subjecting the Compound (I') wherein $R^2$ stands for hydrogen to methoxylation.

For said methoxylation, the methoxylation methods for the 6- or 7-position conventionally adopted in the fields of penicillin or cephalosporin can be applied. The methoxylation of penicillin or cephalosporin is described in detail, for example, by E. M. Gordon, R. B. Sykes, et al in "Chemistry and Biology of β-Lactam Antibiotics", Vol. 1, p. 199 (1982), published by Academic Press, where the description is given on the methods of methoxylation through (1) a diazo intermediate, (2) acylimine intermediate, (3) keteneimine or related imine intermediate, (4) quinoidimine intermediate, (5) sulfeneimine intermediate, (6) eneimine intermediate, etc. By any of these methods can be produced the object compound, and, as a typical method of the methoxylation, the method through an acylimine intermediate is described in detail as follows.

The methoxylation is performed by allowing an alkali metal salt of methanol and a halogenating agent to act on the starting compound (I') wherein $R^2$ is hydrogen in the presence of methanol. As the alkali metal salt of methanol, use is made of lithium methoxide, sodium methoxide, potassium methoxide or the like. As the halogenating agent, use is made of, for example, t-butyl hypochloride, N-chlorosuccinimide, N-chloroacetamide, N-bromoacetamide, N-chlorobenzenesulfonamide, chlorine, bromine, etc. This reaction is conducted in a solvent, as exemplified by tetrahydrofuran, dioxane, dichloromethane, chloroform, acetonitrile, methanol, N,N-dimethylforamide, etc. This reaction is conducted by dissolving or suspending the starting compound in a solvent as exemplified above, then by adding thereto an alkali metal of methanol, methanol and a halogenating agent to thereby allow the reaction to proceed. In this case, it is preferable to add not less than one equivalent of methanol, about 1 to 3.5 equivalents of an alkali metal salt of methanol and about 1 to 2 equivalents of a halogenating agent relative to the starting compound to thereby allow the reaction to proceed. The reaction proceeds at temperatures ranging from about −80° C. to 30° C., and is suspended by making the reaction system acid. As the acid to be used for suspending the reaction, use is made of, for example, formic acid, acetic acid or trichloroacetic acid, as a preferable one. After completion of the reaction, an excess amount of the halogenating agent is removed by processing with a reducing agent as exemplified by sodium thiosulfate, trialkyl ester of phosphorous acid, etc.

The Compound (I'), wherein $R^2$ stands for formylamino, can be prepared by subjecting the Compound (I') wherein $R^2$ stands for hydrogen to formylamination.

The formylamination is conducted by converting the Compound (I'), wherein $R^2$ stands for hydrogen, to an imine derivative of the formula

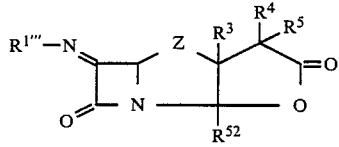
(I')

[wherein $R^{1'''}$ stands for the moiety other than nitrogen in the organic residue bonded through nitrogen; $R^3$, $R^4$, $R^5$, $R^{52}$ and Z are of the same meaning as defined above], then by allowing to act thereon a nucleophilic derivative of formamide represented by the formula

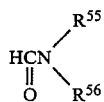

[wherein $R^{55}$ and $R^{56}$ independently stand for hydrogen, silyl* (herein silyl* stands for silyl optionally having substituents such as those mentioned above for silyl* in $R^1$), stannyl or phosphoryl], preferably N,N-bis(-trimethylsilyl)formamide. The said formylamidation reaction is normally carried out in a solvent under inert atmosphere of nitrogen, argon, etc. at temperatures ranging from about −100° C. to −20° C., preferably from about −80° C. to −50° C., and the reaction time ranges from about 10 minutes to 8 hours, preferably from about 15 minutes to 2 hours. The solvent to be used may suitably any non-protonic one, as exemplified by tetrahydrofuran, N,N-dimethylformamide, hexamethylphosphoramide or dioxane. Hydrolysis with an acid or a base subsequent to the reaction gives formation of the formylamide group. The starting compound, an imine derivative, can be produced in accordance with the method as described in the literature by E. M. Gordon, et al. as mentioned above for the methoxylation. The object compounds thus obtained can be isolated and purified by per se known means such as concentration, pH adjustment, phase transfer, solvent extraction, lyophilization, crystallization, recrystallization, fractional distillation, chromatography or the like.

The presence of two or more asymmetric carbons in the basic skeleton of the object compound (I) of the present invention gives theoretically existence of four or more kinds of stereoisomers, and those individual streoisomers and any mixture thereof fall into the scope of this invention. Similarly, in the case where the group represented by $R^1$ has asymmetric carbon and in the case of ester, and also in the case where the group represented by —COOR$^{51}$ [wherein $R^{51}$ is of the same meaning as defined above] at the 2-position of the basic skeleton has asymmetric carbon, stereoisomers occur, and each of these stereoisomers and any mixture of them fall in the scope of this invention. In cases where the above-described reaction produces these stereoisomers as a mixture, individual stereoisomers can be isolated by conventional means such as various chromatographic procedures, recrystallization or the like on necessity.

The compounds of this invention, when produced in the free form, may be allowed to form salts by conventional means, while those obtained in the form of salt may be converted to the free form by conventional means.

Also, the object compounds may in some instances form the intramolecular salts, which also fall within the scope of this invention as well.

The stereoisomers of the object compounds, either alone or as a mixture, can be used as pharmaceuticals.

The Compound (II) used as the starting compound in the method of this invention can be prepared by, for example, the following process. In the formulae, $R^{1'}$, $R^2$, $R^3$, $R^4$, $R^5$, $R^6$ and $R^7$ are of the same meaning as defined above.

METHOD OF PRODUCING COMPOUND (II)

This method comprises allowing a compound (IV) represented by the formula

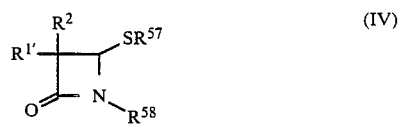
(IV)

[wherein $R^{57}$ stands for hydrogen or a metallic ion of, for example, mercury, silver or thallium; $R^{58}$ stands for hydrogen or a group convertible to hydrogen; $R^{1'}$ and $R^2$ are of the same meaning as defined above] or an ester to react with a compound (V) represented by the formula

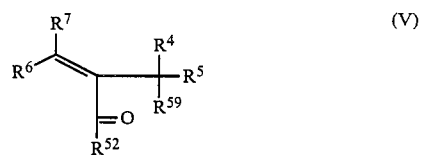
(V)

[wherein $R^{59}$ stands for carboxyl group or a group derivable therefrom; $R^4$, $R^5$, $R^6$, $R^7$ and $R^{52}$ are of the same meaning as defined above] or an ester or a salt thereof, or allowing a compound (VI) representable by the formula

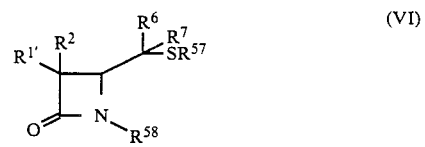
(VI)

[wherein $R^{1'}$, $R^2$, $R^6$, $R^7$, $R^{57}$ and $R^{58}$ are of the same meaning as defined above] or an ester thereof to react with a compound (VII) representable by the formula

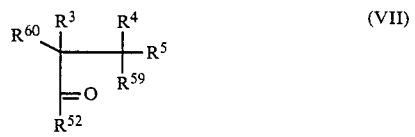
(VII)

[wherein $R^{60}$ stands for a leaving group $R^3$, $R^4$, $R^5$, $R^{52}$, and $R^{59}$ are of the same meaning as defined above] or an ester or a salt thereof to give a compound (VIII) representable by the formula;

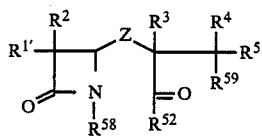

[wherein $R^{1'}$, $R^2$, $R^3$, $R^4$, $R^5$, $R^{52}$, $R^{58}$, $R^{59}$ and Z are of the same meaning as defined above] or an ester or a salt thereof, followed by, when $R^{59}$ of the compound (VIII) is not carboxyl group, converting the $R^{59}$ to carboxyl group, or, when $R^{58}$ is not hydrogen, converting the $R^{58}$ to hydrogen, or, when necessary, subjecting $R^{1'}$ and $R^{52}$ to a conversion reaction such as deprotection or the like, to thereby give the Compound (II). The $R^{57}$ in the above formula (IV) is exemplified by hydrogen or a metallic ion of, for example, mercury, silver or thallium. The $R^{58}$ in the above formulae (IV), (VI) and (VII) is exemplified by hydrogen or a group covertible to hydrogen such as silyl group such as trimethylsilyl, t-butyldimethyl silyl or diphenylmethyl silyl, or, for example, isopropylidene acetic acid ester group

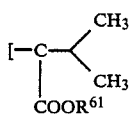

(wherein $R^{61}$ stands for an organic residue bonded through carbon)]. The leaving group represented by $R^{60}$ in the above-mentioned formula (VII) is exemplified by halogen (e.g. bromine, chlorine), sulfonyloxy having substituents (e.g. alkyl, aryl) (alkyl and aryl are exemplified by those substituents mentioned above in reference to $R^1$) (specific examples being p-toluenesulfonyloxy, p-nitrophenylsulfonyloxy, methanesulfonyloxy), disubstituted phosphoryloxy (e.g. diphenylphosphoryloxy, diethylphosphoryloxy), etc.

$R^{59}$ in the above-mentioned formulae (V), (VII) and (VII) is exemplified by carboxyl group or caboxylic acid ester such as t-butyloxycarbonyl, benzyloxycarbonyl, 4-nitrobenzyloxycarbonyl, diphenylmethyloxycarbonyl, aryloxycarbonyl, etc.

The Compounds (IV) and (VI) or their esters and the Compounds (V), (VII), (VIII), (II) or their esters or salts may be referred to briefly as the Compounds (IV), (VI), (V), (VII), (VIII) and (II) respectively hereinafter.

The reaction between the Compound (IV) and the Compound (V) or the Compound (VI) and the Compound (VII) to thereby obtain the Compound (VIII) is conducted in a solvent in the presence of, unless affecting the reaction adversely, a base such as triethylamine, diisopropylamine, pyridine, 4-dimethylaminopyridine. The solvent is exemplified by dichloromethane, chloroform, tetrahydrofuran, dioxane, benzene, toluene, acetonitrile, N,N-dimethylacetamide, N,N-dimethylformamide, hexamethylphosphoramide, etc. The reaction temperature usually ranges from about −20° C. to about 100° C., and the reaction time is in the range of from about 10 minutes to about 50 hours.

The reaction from the Compound (VIII) to the Compound (II) is conducted, when $R^{58}$ of the Compound (VIII) is a silyl group, by allowing the Compound (VIII) to react with an acid (e.g. hydrochloric acid, acetic acid, formic acid, trifluoroacetic acid, etc.) or anion fluoride (e.g. tetra-n-butylammonium. fluoridem potassium fluoride, trityl boron tetrafluoride, etc.) in a solvent. When $R^{58}$ is an isopropylidene acetic ester group, the Compound (VII) is allowed to react with an oxidizing agent (e.g. potassium permanganate, ozone). When $R^{59}$ of the compound ((VIII) is a group derivable from the above-mentioned carboxyl group, and, when the group shown by $R^{1'}$ is protected with a silyl group (including the case where the silyl group is substituted with e.g. alkyl group, etc.), the Compound (VIII) can be converted to the Compound (II) by subjecting the Compound (VIII) to the deprotection reaction methioned above as the conversion of $R^{1'}$ and $R^{52}$ in connection with the method of producing (I) from (I'). For example, when $R^{59}$ is t-butyloxycarbonyl or diphenylmethyloxycarbonyl, the Compound (VIII) is allowed to react with trifluoroacetic acid in the presence of anisole, and in the case of benzyloxycarbonyl or 4-nitrobenzyloxycarbonyl, the conversion is conducted by means of catalytic reduction.

The starting compound, the Compound (IV), can be produced by various known means or those analogous thereto. For example, by referring to the literature references mentioned below, the Compound (IV) can be produced by per se conventional manner or that analogous to the means disclosed therein. (1) Y. Hamashima et al. "Recent Advances in the Chemistry of β-Lactam Antibiotics" No. 28, pp. 243–151 (1977) (2) R. D. G. Cooper, G. A. Koppel, "Chemistry and Biology of β-Lactam Antibiotics" Vol. 1, pp. 1–92, Vol. 2, pp. 315–360 (1982).

The Compound (IV) wherein $R^2$ is hydrogen and $R^{1'}$ is an organic residue bonded through N can be produced in accordance with the following reaction scheme.

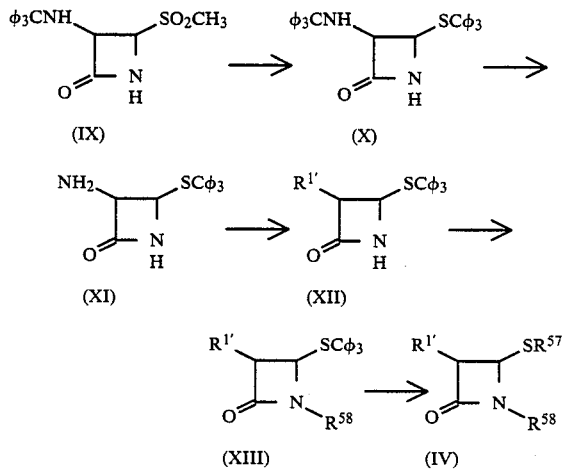

[in the formulae, φ stands for phenyl group, and each of the remaining symbols is of the same meaning as defined above]

The reaction for obtaining the Compound (X) from the Compound (IX) [E. G. Brain et al., J. Chem. Soc. Perkin I, 447(1976)] can be conducted by allowing the Compound (IX) to react with tritylmercaptan in a solvent in the presence of a base. As the base, use is made of, for example, organic amines such as triethylamine, tri-n-butylamine, etc., hydrides, hydroxides, carbonates, etc. of alkali metals such as lithium, sodium potassium, cesium, etc. As the solvent, any one which does not affect the reaction adversely can be employed, as specifically exemplified by water, tetrahydrofuran, dioxane, acetonitrile, N,N-dimethylformamide, N,N-dimethylacetamide, hexamethylphosphoramide or an optional mixture of them. The reaction time ranges from about 5 minutes to about 30 hours, and the reaction temperature normally ranges from about −20° C. to about 100° C.

The reaction from the Compound (X) to the Compound (XI) is conducted by allowing the Compound (X) to react with an acid in a solvent. As the acid, use is made of, for example, p-toluenesulfonic acid, hydrochloric acid, formic acid, etc. As the solvent, any one which does not affect the reaction adversely can be employed, as specifically exemplified by water, tetrahydrofuran, dioxane, acetonitrile, acetone, dichloromethane, ethyl acetate or an optional mixture of them.

The reaction from the Compound (XI) to the Compound (XII) can be carried out in accordance with the reaction for introducing a protective group into the amino group at the 6-position of penicillin or the amino group at the 7-position of cephalosporin or with the acylation thereof. More specifically, the reaction can be carried out in accordance with the method of acylation described above as a convertion reaction for $R^{1'}$ in connection with the production of (I) from (I')

In the above formulae, when $R^{58}$ is a group convertible to hydrogen from among the definition given above, the reaction the Compound (XII) to the Compound (XIII) is carried out by allowing the Compound (XII) to react with a silylating agent such as trimethylsilyl chloride, t-butyldimethylsilyl chloride, t-butyldimethylsilyl trifluoromethane sulfonate (hereinafter "trifluoromethane sulfonate" may be abbrebiated as "triflate") diphenylmethylsilyl chloride, etc. in a solvent in the presence of a base. As the solvent, any one may be employed, so long as it does not affect the reaction adversely, as specifically exemplified by dichloromethane, ethyl acetate, benzene, chloroform, N,N-dimethylformamide, N,N-dimethylacetamide, etc. As the base, use is made of organic amines such as triethylamine, tri-n-butylamine, N,N-dimethylaminopyridine, imidazole or methyl imidazole. The reaction time ranges from about 5 minutes to about 30 hours, and the reaction temperature ranges normally from about −20° C. to about 100° C.

The conversion reaction from the Compound (XIII) to the Compound (IV) wherein $R^{57}$ is a metallic ion among the above-mentioned definition is carried out by adding to the former, for example, mercuric chloride, mercuric nitrate, silver nitrate or thallium nitrate in a solvent in the presence of a metallic ion of mercury, silver or thallium. The Compound (IV), wherein $R^{57}$ is hydrogen, can be obtained by allowing the above-obtained Compound (IV) wherein $R^{57}$ is a metallic ion to further react with hydrogen sulfide. The Compound (IV), wherein $R^{57}$ is hydrogen, can also obtained by allowing the above-obtained Compound (IV) wherein $R^{57}$ is a metallic ion to react with an inorganic acid such as hydrochloric acid, etc. or an organic acid such as acetic acid, formic acid, trifluoroacetic acid, etc. Specific examples of the reaction solvent include methanol, ethanol, tetrahydrofuran, dichloromethane, ethyl acetate, chloroform, N,N-dimethylacetamide, N,N-dimethylformamide, etc. The reaction temperature ranges normally from about −78° C. to about 50° C., but the reaction may be conducted at temperatures outside this range The starting compound, the Compound (V) wherein $R^6$ and $R^7$ are respectively hydrogen and $R^{59}$ is a group derivable from a carboxyl group among the definitions given above can be produced by, for example, the following reaction scheme:

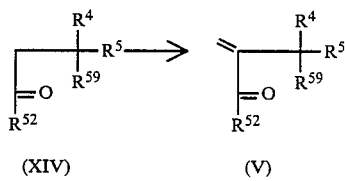

[wherein each symbol is of the same meaning as defined above]. In the reaction shown by the above scheme, the Compound (XIV) can be converted ot the Compound (V) by per se conventional means, for example the method disclosed by Tatusya SHONO, Yoshihiro MATSUMURA, et al. in Journal of Synthetic Organic Chemistry, Japan, 39, 358–373 (1981). For example, the method of producing the Compound (V), wherein $R^4=R^5=R^6=R^7=H$ and $R^{52}=R^{59}=COOCH_2CH_3$, from the Compound (XIV), wherein $R^4=R^5=H$ and $R^{52}=R^{59}=COOCH_2CH_3$, is disclosed in J. Parkt. Chem. 37, 302 (1968). The Compound wherein neither $R^6$ nor $R^7$ is hydrogen or either one of them is not hydrogen, can be produced by, for example, the method shown by the following reaction scheme:

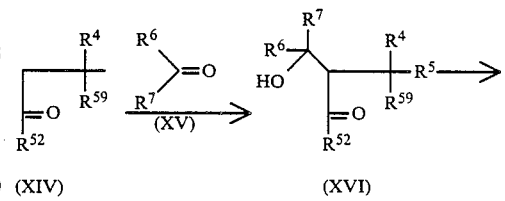

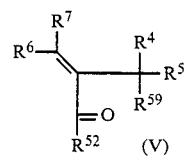

[in the formulae, each symbol is of the same meaning as defined above].

In this process, the Compound (XIV) is subjected to aldol reaction with the Compound (XV) by a per se known means such as those described in, for example:

(1) Shinji IWASAWA et al. Journal of Synthetic Organic Chemistry, Japan 44, 73 (1986)

(2) Mukaiyama et al. Organic Reactions 28 Chapter 3 (1982)

(3) Evans et al. Topics in Sterochemistry 13 Chapter 1 (1982)

(4) Heathcock Asymmetric Synthesis 3 Chapter 2 (1984) to be converted to the Compound (XVI), followed by subjecting the Compound (XVI) to dehydration to give the Compound (V). The starting compound (VI) can be produced in accordance with the following reactions:

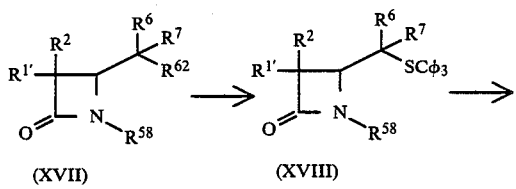

(XVII) (XVIII)

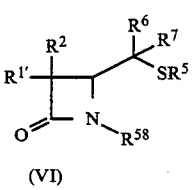

(VI)

[wherein $R^{62}$ stands for a leaving group; $R^{1'}$, $R^2$, $R^6$, $R^7$, $R^{57}$, $\phi$ and $R^{58}$ are of the same meaning as defined above]. The reaction for obtaining the Compound (XVIII) from the Compound (XVII) [synthesizable according to the method described by SENDAI et al. in J. Antibiotics, 38, 346(1985) in carried out by allowing the Compound (XVII) to react with trityl mercaptan in a solvent in the presence of a base. Specific examples of a leaving group shown by $R^{62}$ include bromine, chlorine, iodine, methanesulfonyloxy, trifluoromethanesulfonyloxy.

The reaction for converting the Compound (XVIII) to the Compound (VI) is carried out in a solvent in the presence of a metal ion such as mercury, silver or thallium by adding to the former mercuric chloride, mercuric nitrate, silver nitrate or thallium nitrate. The Compound (VI), wherein $R^{58}$ is hydrogen, can be produced by allowing the Compound obtained thus above wherein $R^{58}$ is not hydrogen to further react with hydrogen sulfide. Also, the Compound (VI), wherein $R^{58}$ is hydrogen, is obtained by allowing an inorgani acid such as hydrochloride acid, etc., or an organic acid such as acetic acid, formic acid, trifluoroacetic acid, etc. to act on the Compound (VI) wherein $R^{58}$ is not hydrogen obtained above. Specific examples of the reaction solvent include methanol, ethanol, tetrahydrofuran, dichloromethane, ethyl acetate, chloroform, N,N-dimethylacetamide, N,N-dimethylformamide, etc. The reaction temperature normally ranges from about $-78°$ C. to about $50°$ C., but the reaction may be conducted outside the said range. As the base, use is made of, for example, organic amines such as pyridine, triethylamine, tri-n-butylamine, etc., hydride, hydroxide, carbonate, etc. of an alkali metal such as lithium, sodium, potassium, cesium, etc. As the solvent, any one can be employed so long as it does not affect the reaction adversely, which is exemplified specifically by water, tetrahydrofuran, dioxane, acetonitrile, N,N-dimethylacetamide, hexamethyl phosphoramide or an optional mixture thereof. The reaction time ranges from about 5 minutes to about 30 hours, and the reaction temperature normally ranges from about $-20°$ C. to about $100°$ C. The starting compound, the Compound (XIV) can be produced by the method shown by the following reaction scheme:

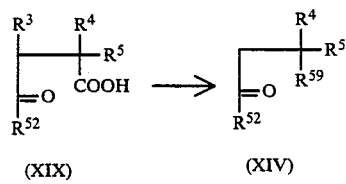

(XIX) (XIV)

[wherein $R^3$ stands for hydrogen, and $R^4$, $R^5$ and $R^{59}$ are of the same meaning as defined above].

In this method, the Compound (XIX) is converted to the Compound (XIV) in accordance with a per se conventional method of esterification of carboxylic acid known in the field of peptides, above all, the esterification mentioned above in respect of the conversion of $R^{1'}$ and/or $R^{52}$ of (I') to lead to (I).

When the starting compound, the Compound (VII), wherein $R^V$ is, among the meanings defined above, a group derivable from carboxyl group, it can be produced by, for example, the following reaction scheme:

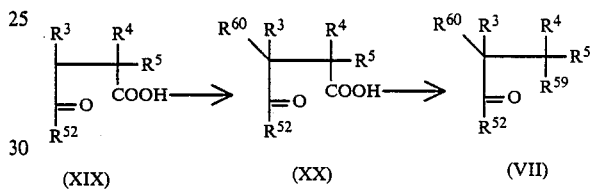

(XIX) (XX) (VII)

[wherein each symbol is of the same meaning as defined above]. In this method, the Compound (XIX) is converted to the Compound (XX) by allowing a halogenating agent such as bromine, chlorine etc. to act thereon in a solvent, followed by converting the Compound (XX) to the Compound (VII) in accordance with a per se conventional method of esterification of carboxylic acid known in the filed of peptide, above all, the esterification mentioned above in respect of the convertion of $R^{1'}$ and/or $R^{52}$ to lead (I') to (I). Examples of the solvent to be used for the reaction to lead the Compound (XIX) to the Compound (XX) include acetic acid, chloroform, dichloromethane, carbon tetrachloride, etc., and the reaction temperature ranges normally from about $-20°$ C. to $100°$ C.

Conversion of the Compound (XX) to (VII) is conducted by, for example, allowing methanol, ethanol or benzyl alcohol to act on the former in the presence of hydrochloric acid or sulfuric acid, allowing diazomethane or diphenyldiazomethane to act thereon or allowing isobutene to act thereon in the presence of sulfuric acid to thereby give an esterified Compound (VII).

The Compound (XIX) to be employed as the starting material can be produced by, for example, the following processes. In the following formulae, $R^3$, $R^4$, $R^5$ and $R^{52}$ are of the same meaning as defined above.

COMPOUND (XXI)→COMPOUND (XIX)

This process is a process of producing the Compound (XIX), i.e. mono ester, by selectively esterifying the carboxyl group at the 1-position alone between the two carboxyl groups of a compound represented by the formula:

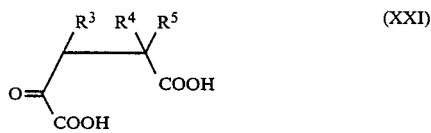

(XXI)

This reaction is carried out by allowing the Compound (XXI) to react with an about equivalent or a little excess amount of an esterifying agent in a solvent in the presence of an equivalent of a base. The esterifying agent is exemplified by halides such as methyl iodide, benzyl bromide, p-nitrobenzyl bromide, m-phenoxybenzyl bromide, p-t-butylbenzyl bromide, diphenylmethyl bromide, pivaloyloxymethyl chloride, etc., dialkyl sulfates such as dimethyl sulfate, diethyl sulfate, etc., etc. As the base, use is made of, for example, organic amines such as diisopropylamine, dicyclohexylamine, cyclohexyl isopropylamine, triethylamine, tripropylamine, tri-n-butylaimne, diisopropylethylamine, DABCO, DBU, N-methyl morpholine, N-methylpiperidine, N-methylpyrrolidine, 3,4-dihydro-2H-pyrido[1,2-a]pyrimidin-2-one, 4-dimethylaminopyridine, pyridine, lutidine, γ-collidine, etc., hydrides, hydroxides, carbonates, etc. of alkali metals such as lithium, sodium, cesium, etc., etc.

As the solvent, use is made of N,N-dimethylformamide, N,N-dimethylacetamide, hexamethylphosphoramide, dimethylsulfoxide, dichloromethane, acetonitrile, tetrahydrofuran, etc. The reaction temperature ranges normally from about −20° C. to about 100° C. The reaction time ranges from about 5 minutes to 30 hours.

COMPOUND (XXI)→COMPOUND (XXII)→COMPOUND (XXIII)→COMPOUND (XIX)

This process is a process of producing the Compound (XIX) by allowing the Compound (XXI) to react with benzyl carbamate to give the Compound (XXII) represented by the formula:

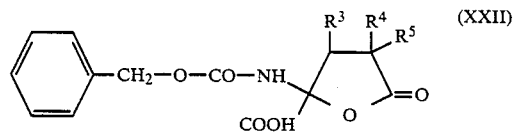

(XXII)

then subjecting the Compound (XXII) to esterification to produce the Compound (XXIII) represented by the formula:

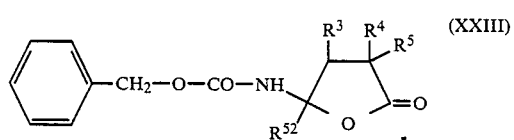

(XXIII)

followed by treating the Compound (XXIII) to treatment with an acid to produce the Compound (XIX).

This process is carried out by using about an equivalent or a little excess amount of benzyl carbamate relative to the Compound (XXI) and subjecting to dehydration condensation by heating under reduced pressure usually in the absence of a solvent. The reduced pressure ranges from about 0.1 mmHg to about 50 mmHg. The reaction temperature ranges normally from about 50° C. to about 120° C., and the reaction time is in the range of from about 30 minutes to about 20 hours. The Compound (XXII) is then subjected to esterification to be converted to the Compound (XXIII). The esterification is carried out by applying the conditions such as in the case of esterification of the above-mentioned Compound (XXI) to the Compound (XIX). In some instances, further esterification is conducted with diazoalkanes such as diazomethane or with, for example, methanol, ethanol, benzyl alcohol, etc. in the presence of a condensing agent, carbodiimide such as DCC, etc. The esterification method is suitably selected depending on the esters desired, and the ester to be employed here is one relatively stable against acids, because an acid is used in the subsequent reaction. The Compound (XXIII) is brought into contact with an acid to be thereby converted to the Compound (XIX). As the acid, use is made of, for example, an excess amount of hydrochloric acid, sulfuric acid, hydrobromic acid, perchloric acid, periodic acid, formic acid, acetic acid, trifluoroacetic acid, p-toluenesulfonic acid, etc. singly or in an optional combination. Among them, a combination of hydrobromic acid with acetic acid is preferably employed. The reaction temperature ranges from about 0° C. to about 50° C., and the reaction time ranges from about 15 minutes to about 5 hours.

COMPOUND (XXI)→COMPOUND (XXIV)→COMPOUND (XIX)

This process is a process of producing the Compound (XIX) by allowing a halogenocarbonate to react with the Compound (XXI) to give the Compound (XXIV) represented by the formula:

(XXIV)

followed by subjecting the Compound (XXIV) to decarboxylation. For example, synthesis of 1-ethyl ester of 2-oxoglutaric acid by allowing 2-oxoglutaric acid [the Compound (XXI) wherein $R^3=R^4=R^5=H$] to react with ethyl chlorocarbonate followed by decarboxylation is described by J. M. Domagala in Tetrahedron Letters 21, p. 4997, 1980. This reaction can be perfected by allowing the Compound (XXI) to react with a halogenocarbonate carbonate in a solvent in the presence of a base, followed by decarboxylation to produce the Compound (XIX). Specific examples of the halogenocarbonate include methyl chlorocarbonate, ethyl chlorocarbonate, benzyl chlorocarbonate, 2,2,2-trichloroethyl chlorocarbonate. As the base to be used here, use is made of, for example, organic amines such as triethylamine, tripropylamine, tri-n-butylamine, diisopropylethylamine, triethylene diamine, DABCO, DBU, N-methylmorpholine, N-methylpiperidine, N-methylpyrrolidine, 3,4-dihydro-2H-pyrido[1,2-a]pyrimidin-2-one, 4-dimethylaminopyridine, pyridine, lutidine, γ-collidine, etc., alkali metals such as lithium, sodium, potassium, cesium, etc., alkaline earth metals such as magnesium, calcium, etc., or hydrides, hydroxides, carbonates or alcoholates of them. As the solvent, use is made of, for example, conventional ones such as dichloromethane, chloroform, tetrahydrofuran dioxane, benzene, toluene, acetonitrile, dimethylacetamide, dimethylformamide, etc. For this reaction, about an equivalent of a base and an equivalent halogenocarboate relative to the Compound (XXI) may be employed. The reaction temperature ranges from about −30° C. to 60° C., and the reaction time ranges from about one minute to two hours. The Compound (XXIV) is not necessarily isolated, and the decarboxylation proceeds subsequently under the afore-mentioned conditions to thereby obtain the Compound (XIX).

COMPOUND (XXI)→COMPOUND (XXV)→COMPOUND (XIX)

This process is a process of producing the Compound (XIX) by allowing a dehydrating agent to act on the Compound (XXI) to give an acid anhydride i.e. the Compound (XXV) represented by the formula:

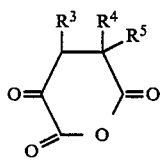
(XXV)

followed by allowing alcohol to react with the Compound (XXV). Examples of the dehydrating agent to be employed in this reaction include compounds such as phosphorus oxychloride, thionyl chloride, chlorosulfonic acid, etc., acid anhdyrides of lower aliphatic acid such as acetic anhdyride, trifluoroacetic anhydride, etc., acid halides such as acetyl chloride, etc., imidazole derivatives such as N,N'-carbonyl diimidazole, etc., DCC, etc. When the above-mentioned acid halide is used, an organic base such as pyridine, triethylamine, etc. is preferably employed jointly. This reaction is carried out by using about an equivalent or an excess amount of dehydrating agent relative to the Compound (XXI) in a solvent, or when the dhydrating agent is in liquid state, the dehydrating agent is used also as the solvent. As the solvent, use is made of, for example, dichloromethane, benzene, toluene, acetonitrile, etc. The reaction temperature normally ranges from about 0° C. to about 100° C., and the reaction time ranges from about 15 minutes to about 30 hours. The Compound (XXV) is subsequently allowed to react with about an equivalent to an excess amount of alcohol to give the Compound (XIX). As the alcohol, use is made of alcohols represented by the above-mentioned $R^{51}OH$ or $R^{51'}OH$ [wherein $R^{51}$ and $R^{51'}$ are of the same meaning as defined above], as exemplified by methyl alcohol, ethyl alcohol, benzyl alcohol, p-nitrobenzyl alcohol, t-butyl alcohol, etc. In this reaction, use is made of, in some instances, a catalyst such as sulfuric acid, p-toluenesulfonic acid, zinc chloride, sodium acetate, pyridine, 4-dimethyl aminopyridine, 4-pyrrolidinopyridine, triethylamine, calcium carbonate, etc. The reaction temperature ranges from about 0° C. to about 100° C., and the reaction time ranges from about 10 minutes to 4 days.

COMPOUND (XXI)→COMPOUND (XXVI)→COMPOUND (XXVII)→COMPOUND (XXVIII)→COMPOUND (XIX)

This process is a process to produce the Compound (XIX) by subjecting the Compound (XXI) to diesterification to give the Compound (XXVI) represented by the formula:

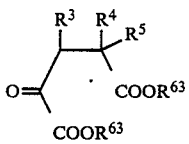
(XXVI)

then by selectively hydrolyzing the ester group of the 1-position alone to convert to the Compound (XXVII) represented by the formula:

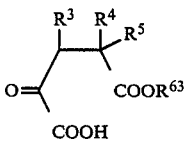
(XXVII)

then by introducing into the carboxyl group at the 1-position an ester group different from that at the 5-position to give the Compound (XXVIII) represented by the formula:

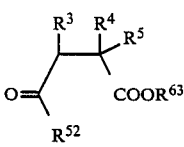
(XXVIII)

followed by converting selectively the ester group at the 5-position alone to carboxyl group to produce the Compound (XIX). As $R^{63}$ in the above formulae (XXVI), (XXVII) and (XXVIII), there are exemplified by alkyls such as methyl, ethyl, etc., aralkyls such as benzyl, p-bromobenzyl, p-nitrobenzyl, etc.

The reaction of converting the Compound (XXI) to the Compound (XXVI) is carried by the method described above in relation to the method of producing the Compound (XIX) from the Compound (XXI) using an esterifying agent and a base, both in about 2 equivalents to an excess amount relative to the Compound (XXI), respectively. The hydrolysis of the Compound (XXVI) to the Compound (XXVII) is normally carried out in a solvent using a base such as a hydroxide, carbonate or alcoholate of an alkali metal such as lithium, sodium, potassium, cesium etc. As the solvent, use is made of, for example, water, methanol, ethanol, tetrahydrofuran, dimethylsufloxide, etc. singly or in an optional mixture thereof. This hydrolysis reaction is carried out using a base usually in an amount of about an equivalent relative to the Compound (XXVI). The reaction temperature ranges normally from about 0° C. to about 80° C., and the reaction time is in a range of from about 10 minutes to about 20 hours. The reaction of esterifying the Compound (XXVII) to the Compound (XXVIII) can be carried out in accordance with the method described above in relation to the method of producing the Compound (XIX) from the Compound (XXI). Further, in some instances, the Compound (XXVII) is allowed to react with isobutene in the presence of an acid catalyst to produce the corresponding t-butyl ester. When the ester group at the 1-position is stable against base while the ester group at the 5-position is not (e.g. in cases where $R^{52}$=t-butyl, $R^{63}$=methyl, etc.), the reaction of converting the Compound (XXVIII) to the Compound (XIX) is performed by applying the above-mentioned method of alkali hydrolysis of the Compound (XXVI) to the Compound (XXVII). When the ester group at the ester group at the 1-position is stable against reduction conditions while the ester group at the 5-position is not (e.g. in cases where $R^{52}$=t-butyl, $R^{63}$=benzyl, etc.), a mono ester compound [the Compound (XIX)] can be selectively obtained by a reducing method. Reducing methods employable here include those of catalytic reduction using a metal catalyst such as palladium carbon, palladium black, palladium barium carbonate, platinum oxide, platinum black, Raney nickel, etc., those of reduction using a metal such as zinc, iron, chromium, etc. together with acid such as hydrochloric acid, formic acid, acetic acid, etc., of the like. These methods by means of reduction are usually conducted in a solvent, as exemplified by water, methanol, ethanol, ethyl acetate, acetone or acids mentioned above. The reaction temperature ranges normally from about 0° C. to about 60° C., and the reaciton time is in the range of from about 10 minutes to 20 hours.

COMPOUND (XXIX)→COMPOUND (XXX)→COMPOUND (XXXI)→COMPOUND (XXXII)→COMPOUND (XXVIII)→COMPOUND (XIX)

This process is a process of producing the Compound (XIX) by esterifying the Compound (XXIX) represented by the formula:

(XXIX)

to give the Compound (XXX) represented by the formula:

(XXX)

then hydrolyzing the Compound (XXX) to give the Compound (XXXI) represented by the formula:

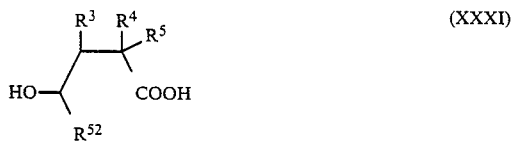

(XXXI)

further esterifying the Compound (XXXI) to convert to the Compound (XXXII) represented by the formula:

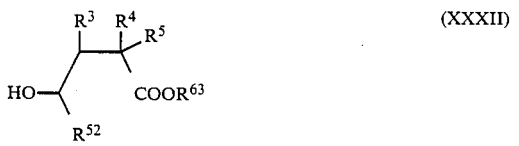

(XXXII)

then oxidizing the hydroxyl group of the Compound (XXXII) thus obtained to give the Compound (XXVIII) (referred to in the foregoing), followed by subjecting the Compound (XXVIII) to the reaction of converting the Compound (XXVIII) to the Compound (XIX) as described above.

The starting Compound (XXIX), wherein $R^3=R^4=R^5=H$, is known the literature, and it can be easily synthesized from glutamic acid [cf. Taniguchi et al., Tetrahedron 30, 3547 (1974)]. Compounds wherein $R^3$ to $R^5$ are each a substituent as defined above can be synthesized in accordance with this method. The esterification of the Compound (XXIX) to the Compound (XXX) can be achieved according to the method of producing the Compound (XIX) from the Compound (XXI). Further, in some instances, the Compound (XXIX) may be allowed to form an adduct of alkene such as isobutene in the presence of a catalyst such as an acid e.g. sulfuric acid, hydrochloric acid, etc. or boron trifluoride, etc. to give a t-alkyl ester. This reaction is usually carried out in a solvent, as exemplified by dichloromethane, chloroform, dioxane, diethyl ether, tetrahydrofuran, benzene, etc. The reaction is carried out by, after introducing an excess amount of isobutene, reacting temperatures ranging from about 0° C. to 50° C. for about 5 hours to several days in a sealed vessel. The hydrolysis of the Compound (XXX) to the Compound (XXXI) is carried out by applying the method described above in relation to the method of producing the Compound (XXVII) from the Compound (XXVI). In this reaction, it is necessary to select a type of the Compound whose ester group is relatively stable against alkali (e.g. $R^{52}$=t-butyloxycarbonyl). The esterification of the Compound (XXXI) to the Compound (XXXII) can be carried out according to that as mentioned above in relation to the method of converting the Compound (XXII) to the Compound (XXIII). The reaction of oxidizing the Compound (XXXII) to the Compound (XXXIII) is carried out by allowing the former to react with an oxidizing agent in a solvent. As the oxidizing agent, use is made of potassium permanganate, manganese dioxide, dimethylsulfoxide (DMSO)-DCC, DMSO-acetic anhydride, DMSO-phosphorus pentoxide, etc., for example. As the solvent, use is made of dichloromethane, chloroform, acetonitrile, ethyl acetate, benzene, toluene, DMSO, N,N-dimethylformamide, acetone, ether, etc. In this reaction, an oxidizing agent is used in an amount of usually about an equivalent to an excess relative to the Compound (XXXII). The reaction temperatures are in a range of from about −80° C. to 60° C., and the reaction time ranges from about 10 minutes to 30 hours.

The Compound (XIX) wherein $R^{52}$ is an amidated carboxyl group can be produced by applying the above-mentioned method of amidating carboxylic acid to the above-mentioned Compound (XXVII) to produce the Compound (XXVIII) followed by conducting the method in accordance with the method described above in relation to the method of producing the Compound (XIX) from the Compound (XXVIII).

The Compound (XXI), which is a starting compound for the present invention, can be produced by various methods which have already been reported. For example, the Compound (XXI) is per se known in the references set forth below and it can be produced in accordance with the methods described therein or the methods analogous thereto.

(1) Organic Synthesis, Collective Vol. 3, 510 (1955)
(2) M. E. E. Blaise et al.: Bulletin de la Societe Chimique de France, 9, 458 (1911)

(3) W. H. Perkin et al.: Journal of the Chemical Society, 79, 729 (1901)
(4) J. C. Bardhan: Jounal of the Chemical Society, 2591 (1928)
(5) W. N. Haworth et al.: Journal of the Chemical Society, 105, 1342 (1914)
(6) F. C. Hartman: Biochemistry, 20, 894 (1981)
(7) G. Hesse et al.: Annalen der Chemie, 697, 62 (1966)

The Compound (XXI) can be produced in accordance with the following reaction scheme:

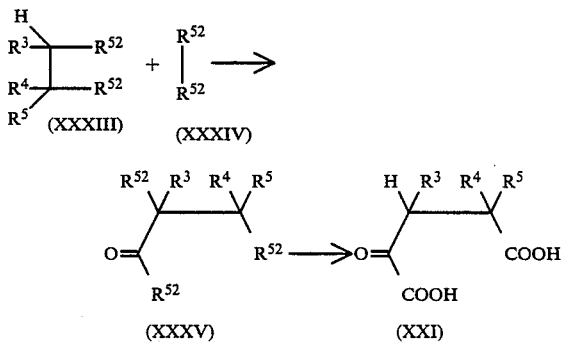

In the above formulae, $R^3$, $R^4$, $R^5$ and $R^{52}$ are of the same meanings as defined above.

The conversion of the Compound (XXXIII) to the Compound (XXXV) is a reaction which is well known as what is called Claisen condensation, where the Compound (XXXIII) and the Compound (XXXIV) are subjected to condensation in a solvent in the presence of a base. As the base, use is made of, for example, alkali metals such as lithium, sodium, potassium, etc., alkaline earth metals such as magnesium, calcium, etc., hydrides, alcoholates, amides, alkyl metals of them; or quaternary ammonium, etc. As the solvent, use is made of alcohols such as methanol, ethanol, etc. (in cases where an alcoholate is used, the alcohol to be used in one having the same alkoxy group as that of the alchoholate), ether, tetrahydrofuran, dioxan N,N-dimethylformamide, 1,2-dimethoxyethane, dichloromethane, benzene, toluene, etc. The reaction temperature normally ranges from about 0° C. to about 80° C., and the reaction time is in the range of from about 10 minutes to about 10 hours.

The conversion of the Compound (XXXV) to the Compound (XXI) is a process of producing the Compound (XXI) by treating the Compound (XXXV) with an acid, alkali or reducing agent. This reaction can be carried out in accordance with, for example, the above-mentioned method of producing the Compound (XXVII) from the Compound (XXVI) or of producing the Compound (XIX) from the Compound (XXVII).

METHOD OF PRODUCING COMPOUND (III)

This is a process of producing the Compound (III) by reacting the Compound (VIII) to obtain a compound represented by the formula:

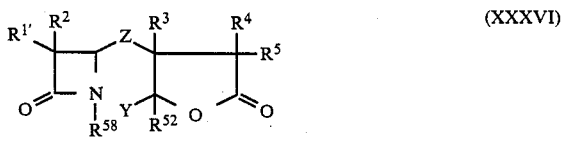

[wherein $R^{1'}$, $R^2$, $R^3$, $R^4$, $R^5$, $R^6$, $R^{58}$, Z and Y are of the same meanings as defined above, respectively], and, when $R^{58}$ of the compound thus obtained is a group convertible to hydrogen, by converting the group $R^{58}$ to hydrogen.

This reaction is usually carried out by reacting the Compound (VIII) with an activating agent in the presence or absence of a solvent. Activating agents employable here include the carboxyl group-activating agents described and exemplified above in relation to the reaction of converting the Compound (II) to (I'), and this reaction is carried out by treating the Compound (VIII) with an activating agent as mentioned above in a nearly equivalent or an excess amount relative to the said Compound (VIII) in a solvent or in the absence of solvent. This reaction may be carried out by using a base such as triethylamine, diisopropylethylamine, pyridine, 4-dimethylaminopyridine, etc., so long as it does not interfere with the reaction. As the solvent, use is made of, dichloromethane, chloroform, carbon tetrachloride, 1,2-dichloroethane, N,N-dimethylformamide, N,N-dimethylacetamide, acetonitrile, tetrahydrofuran, benzene, toluene, etc. The reaction temperature ranges normally from about −20° C. to about 100° C., and the reaction time is in a range of from about 30 minutes to about 50 hours. In the Compound (XXXVI), when $R^{58}$ is a group convertible to hydrogen among the definition given above, the Compound (XXXVI) is converted to the Compound (III) in accordance with the method of producing the Compound (II) from the Compound (VIII). The respective intermediate compounds thus obtained can be isolated by per se known means such as concentration, pH change, phase transfer, solvent extraction, lyophilization, crystallization, recrystallization, fractional distillation, chromatography, etc.

The Compound (II) and the Compound (III) thus obtained are novel substances, and they are useful as starting compounds for the production of, for example, the Compound (I').

As the esters of intermediate Compounds (II), (III), (IV), (V), (VI), (VII) and (VIII) and as the salts of Compounds (II), (III), (V), (VII) and (VIII), there are mentioned, for example, the esters mentioned above with regard to the group of the formula —COOR$^{51}$ and the salts of the Compound (I) respectively.

The Compound (I) obtained thus above, salts thereof and esters thereof are useful as pharmaceuticals, particularly having antibacterial activity on, for example, some species of gram-positive and gram-negative bacteria. The antibacterial spectra of typical compounds among the Compounds (I) against various microorganisms are as shown in Table 1 below.

TABLE 1

| | | Minimum Growth Inhibitory Concentration (Note 2) | | |
|---|---|---|---|---|
| Microorganism | (Note 1) (μg/ml) | Compound (I-5) | Compound (I-6) | Compound (I-18) |
| Escherichi coli | NIH JC 2 | 0.2 | 6.25 | <0.1 |
| Citrobacter freundii | IFO 12681 | 0.39 | 12.5 | <0.1 |
| Klebsiella pneumoniae | DT | <0.1 | 1.56 | <0.1 |
| Enterobacter cloacae | IFO 12937 | 12.5 | 100 | <0.1 |
| Serratia marcescens | IFO 12648 | 0.2 | 12.5 | <0.1 |
| Proteus vulgaris | IFO 3988 | <0.1 | 1.56 | <0.1 |
| Proteus mirabilis | IFO 3849 | 0.2 | 6.25 | 0.2 |
| Proteus morganii | IFO 3168 | 1.56 | 25 | 1.56 |

(Note 1) Culture Medium: Trypticase soy agar
Inoculum concentration: 10 CFU/m
(Note 2) Compounds (I-5), (I-6) and (I-18) are the compounds produced in the following Working Examples 5, 6 and 18, respectively.

The compounds of the present invention are of low toxicity.

As described thus above, the compounds of the present invention exhibit antibacterial action against certain species of gram-positive and gram-negative bacteria, which can be used as therapeutic agents or antibacterial agents for bacterial infections (e.g. respiratory infections, urinary tract infections, suppurative diseases, bile duct infections, intraintestinal infections, gynecological infections, surgical infections, etc.) in mammals (e.g. mice, rats, dogs, pigs, bovines and humans, etc.) suffering from bacterial infections.

The compounds of the present invention can be orally administered in combination with a suitable pharmacologically acceptable carrier, excipient or diluent in a dose form of, for example, tablet, granule, capsule, drop, etc. They can also be parenterally administered in a dose form of, for example, injection prepared by conventional means, incorporated with a conventional sterile carrier.

The daily dosage of the compounds of this invention, when they are administered in a form of, for example, injection, is in the range of from about 2 to about 100 mg/Kg, more preferably, about 5 to 40 mg/Kg in terms of the Compound (I).

On account of their antimicrobial properties, the compounds of this invention may be used an an antiinfective agent or a disinfectant for removing bacteria including the afore-mentioned bacteria from surgical instruments or hospital rooms.

For example, surgical instruments are put for 2 days in an aqueous solution containing 1000 μg/ml of any compound of this invention for the above purpose. However, in the case where esters of this invention are employed for this purpose, the corresponding deesterified compounds are put into use.

In producing the above-mentioned oral pharmaceutical preparations such as tablets, they can be optionally incorporated with a binder (e.g. hydroxypropylcellulose, hydroxypropylmethylcellulose, macrogol, etc.), a disintegrating agent (e.g. starch, carboxymethylcellulose calcium, etc.), an excipient (e.g. maltose, starch, etc.), a lubricant (e.g. magnesium stearate, talc, etc.), etc.

In producing the parenteral pharmaceutical preparations such as injections, they can be optionally incorporated with an isotonizing agent (e.g. glucose, D-sorbitol, D-mannitol, sodium chloride, etc.), a preservative (e.g. benzyl alcohol, chlorobutanol, methyl p-oxybenzoate, propyl p-oxybenzoate, etc.), a buffering agent (e.g. phosphate buffer solutions, sodium acetate buffer solution, etc.), etc.

The following working examples and reference examples will illustrate the present invention in further detail, but it should be understood that they are nothing more than practical embodiments and in no way limit the invention. They can, of course, be suitably modified unless they do not deviate from the scope of the invention.

Elution in the column chromatography in the working examples as well as in the reference examples was conducted under the observation by means of TLC (Thin Layer Chromatography), unless otherwise specified. For the TLC observation were employed 60F$_{254}$ (manufactured by E. Merck) as the TLC plate, the solvents used as eluents for column chromatography as the developing solvents, and a UV detector as detecting means. Besides, the following means was jointly employed for the detection; namely, 48% HBr was sprayed on the spots of the TLC plate, which was hydrolyzed by heating, then a ninhydrin reagent was sprayed thereon, followed by heating again and observing the change of the color to red to reddish purple. The eluate fractions containing the object prodcut was thus confirmed and collected.

Referring to the developing solvents, the numerical values in parenthesis ( ) show the mixed volume ratio of the respective solvents. In the case where two kinds of developing solvents are used, the solvent of the volume ratio given first elutes by-products and the solvent of the volume ratio shown after the arrow mark in the parenthesis ( ) elutes the object product, unless otherwise specified. For the purification by means of a column chromatography using Amberlite XAD-2, as the developing solvents were employed water first, then an aqueous solution of ethanol while increasing the concentration gradually, unless specifically referred thereto in the working examples and reference examples.

"Amberlite" is a product of Rohm & Haas Co. in U.S.A. Unless othewise specified, silica gel used for the column was Wako Gel C-300 (200–300 mesh) manufactured by Wako Pure Chemicals Industries, Ltd., and a flash chromatography was conducted in accordance with the method described in Journal of the Organic Chemistry, 43, 2923 (1978). NMR spectrum was measured with VARIAN EM 390 (90 MHz), VARIAN T 60 (60 MHz) or JEOL JNM-GX400 (400 MHz) spectrometer, using tetramethylsilane as internal or external standard and all the δ values were shown by ppm. As mass spectrum, those designated as FD-MS and SIMS respectively mean Field Desorption and Secondary Ion Mass Spectrum measured with Hitachi M-80A spectrometer. "Room temperature" means normally 0° C. to 40° C. Unless otherwise specified, % means weight %. Numerical values with parenthesis ( ), when a mixed solvent is employed, show mixed ratios by volume of the respective solvents. The abbreviations used in the working examples and reference examples have the meaning defined as follows.

s: singlet, d: doublet, t: triplet, q: quartet,
ABq: AB type quartet, dd: double doublet,
m: multiplet, sh: shoulder, b, br: broad,
J: coupling constant, mg: milligram, g: gram,
ml: milliliter, μl: microliter, l: liter,
ppm: part per million; Hz: Herz, DMSO: dimethyl sulfoxide, D$_2$O: heavy water

REFERENCE EXAMPLE 1

Production of 1-(4-nitrobenzyl) 2-oxoglutarate [Compound (1)]

(a) To a solution of 2.93 g of 2-oxoglutaric acid in 20 ml of dimethylformamide was added 3.63 g of dicyclohexylamine, and the mixture was heated to 50° C., followed by addition of 4.75 g of 4-nitrobenzyl bromide. The whole mixture was stirred at 70° C. for 15 minutes, to which was added, after cooling, 100 ml of ethyl acetate. Precipitating crystals were collected by filtration and washed with ethyl acetate. The filtrate and the washing were combined, which was washed with water and a saturated aqueous saline solution, followed by drying (MgSO$_4$). The solvent was distilled off under reduced pressure, and the residue was subjected to a silica gel chromatography, eluting with hexane-ethyl acetate-acetic acid (50:50:1), followed by collecting fractions containing the end product. The fractions were concentrated under reduced pressure to give 5.2 g of the subject Compound (1) as crystals, m.p. 100°–102° C.

IR$\nu_{max}^{KBr}$ cm$^{-1}$: 1735, 1707, 1530, 1345, 1275, 1085.

NMR (90 MHz, CDCl$_3$-d$_6$-DMSO)δ: 2.5–2.8 (2H, m), 2.9–3.3 (2H, m), 5.40 (2H, s), 7.62 (2H, d, J=9 Hz), 8.28 (2H, J=8 Hz).

Elemental Analysis for C$_{12}$H$_{11}$NO$_7$: Calcd.: C, 51.25; H, 3.94; N, 4.98. Found: C, 51.17; H, 3.92; N, 4.96.

(b) To a solution of 2.93 g of 2-oxoglutaric acid in 20 ml of dimethylformamide were added 2.79 ml of triethylamine and 4.53 g of 4-nitrobenzyl bromide, followed by stirring at room temperature for 5 hours. The reaction mixture was poured into ice-water, which was subjected to extraction (twice) with ethyl acetate, followed by the same procedure as Example 1 (a) to give 3.6 g of the subject Compound (1) as crystals.

(c) To a suspension of 3.36 g of monosodium 2-oxoglutarate in 30 ml of dimethylformamide was added 4.53 g of 4-nitrobenzyl bromide. The mixture was stirred at 50° to 60° C. for two hours. The reaction mixture was poured into ice-water, which was subjected to extraction (twice) with ethyl acetate, followed by the same procedure as Example 1 (a) to give 3.92 g of the subject Compound (1) as crystals.

REFERENCE EXAMPLE 2

Production of 1-methyl 2-oxoglutarate [Compound (2)]

In 100 ml of dimethylformamide was dissolved 27.93 g of 2-benzyloxycarbonylamino-5-oxo-2-tetrahydrofurancarboxylic acid prepared by the method described in Journal of Organic Chemistry, 6, 878 (1941). To the solution was added 4.0 g of sodium hydride (60% oil), to which was then added 28.4 g of methyl iodide, followed by allowing the reaction to proceed at room temperature for 4 hours. To the resultant was added 28.4 g of methyl iodide, and the mixture was stirred for further 3 hours. The reaction mixture was added to water, which was subjected to extraction with ethyl acetate. The organic layer was washed with a saturated aqueous solution of sodium hydrogencarbonate and a saturated aqueous saline solution, successively, then dried (MgSO$_4$). The solvent was distilled off, and precipitating crystals were collected by filtration, followed by washing with ether to give 27.25 g of methyl 2-benzyloxycarbonylamino-5-oxo-2-tetrahydrofurancarboxylate as colorless crystals, m.p. 134°–134.5° C.

IR$\nu_{max}^{KBr}$ cm$^{-1}$: 3295, 1780, 1758, 1700, 1540, 1308, 1196, 1049.

To 10 g of this product was added 20 ml of a 30% acetic acid solution of hydrogen bromide, and the mixture was stirred for 30 minutes. The reaction mixture was washed (decantation) twice with 500 ml (twice) of hexane-ether (9:1). To the residue was added water, which was subjected to extraction (4 times) with ethyl acetate. The organic layer was washed with a saturated aqueous saline solution, dried (MgSO$_4$), followed by distilling off the solvent. The residue was subjected to a silica gel column chromatography, eluting with hexane-ethyl acetate (1:1). Fractions containing the end product were collected and concentrated under reduced pressure to give 2.95 g of the subject Compound (1) as colorless crystals, m.p. 54.5°–55.0° C.

IR$\nu_{max}^{KBr}$ cm$^{-1}$: 3430, 1750, 1735, 1710, 1275, 1255, 1225, 1080.

NMR (90 MHz, CDCl$_3$)δ: 2.60–3.27 (4H, m), 3.88 (3H, s), 8.20 (1H, bs).

Elemental Analysis for C$_6$H$_8$O$_5$: Calcd.: C, 45.01; H, 5.04. Found: C, 44.92; H, 4.92.

REFERENCE EXAMPLE 3

Production of 1-(4-nitrobenzyl) 2-oxoglutarate [Compound (1)]

To a solution of 838 mg of 2-benzyloxycarbonylamino-5-oxo-2-tetrahydrofurancarboxylic acid in 5 ml of dimethylformamide was added 120 mg of sodium hydride (60% oil) while stirring under ice-cooling. To the mixture was then added 648 mg of 4-nitrobenzyl bromide, followed by stirring at room temperature for 2.5 hours. To the reaction mixture was added a saturated aqueous solution of sodium hydrogencarbonate, which was subjected to extraction with ethyl acetate. The organic layer was washed with a saturated aqueous saline solution and then dried (MgSO$_4$), followed by distilling off the solvent. The residue was subjected to a silica gel column chromatography, eluting with hexane-ethyl acetate (1:1). Fractions containing the end product were combined and concentrated under reduced pressure to give 687 mg of 4-nitrobenzyl 2-benzyloxycarbonylamino-5-oxo-2-tetrahydrofurancarboxylate as colorless crystals, m.p. 127°–127.5° C.

IR$\nu_{max}^{KBr}$ cm$^{-1}$: 3310, 1780, 1759, 1728, 1520, 1345, 1185, 1042.

Using 2.07 g of this compound, the reaction was allowed to proceed in the same manner as that in Reference Example 2 to give 1.14 g of the subject compound (1). The compound thus produced was in completely identical to the compound (1) obtained in Reference Example 1 in the melting point, IR and NMR spectrum.

REFERENCE EXAMPLE 4

Production of 1-benzyl 2-oxoglutarate [Compound (4)]

In 20 ml of anhydrous dimethylformamide was dissolved 2.92 g of 2-oxoglutaric acid. To the solution were added 3.63 g of dicyclohexylamine and 2.61 ml of benzyl bromide, followed by stirring at room temperature for 2 hours. To the reaction mixture was added ethyl acetate, and then precipitating crystals were filtered off. The filtrate was washed with water, then dried (Na$_2$SO$_4$), and the solvent was distilled off. The residue was subjected to a silica gel column chromatography, eluting with hexane-ethyl acetate-acetic acid (50:50:1). Fractions containing the end product were collected and concentrated under reduced pressure to give 3.20 g of the subject Compound (4) as colorless crystals. Recrystallization from ether-hexane gave colorless prisms, m.p. 51°–52° C.

IR$\nu_{max}^{Nujol}$ cm$^{-1}$: 1740, 1705, 1270, 1090, 1040.

NMR (90 MHz, CDCl$_3$)δ: 2.67 (2H, t, J=6 Hz), 2.97 (2H, m), 5.26 (2H, s), 7.35 (5H, s), 8.9 (1H, b).

Elemental Analysis for C$_{12}$H$_{12}$O$_5$: Calcd.: C, 61.01; H, 5.12. Found: C, 61.02; H, 5.12.

REFERENCE EXAMPLE 5

Production of 1-(4-nitrobenzyl) 4-methyl-2-oxoglutarate [Compound (5)]

In 6 ml of anhydrous dimethylformamide was dissolved 0.74 g of 4-methyl-2-oxoglutaric acid. To the solution were added 0.93 ml of dicyclohexylamine and 1.0 g of 4-nitrobenzyl bromide, and the mixture was stirred at room temperature for 14 hours. To the reaction mixture was added ethyl acetate, then precipitating crystals were filtered off. The filtrate was washed with water and dried (Na$_2$SO$_4$), followed by distilling off the solvent. The residue was subjected to a silica gel column chromatography, eluting with hexane-ethyl acetate (1:1→1:3). Then, fractions containing the object compound were collected and concentrated under reduced pressure to give 0.66 g of the subject Compound (5) as a pale yellow oily substance.

IR$\nu_{max}^{Neat}$ cm$^{-1}$: 1780-1700, 1520, 1345, 1220, 1170.

NMR (90 MHz, CDCl$_3$)$\delta$: 1.32 (3H, d, J=6 Hz), 2.2-3.3 (3H, m), 5.38 (2H, s), 6.0 (1H, b), 7.55 (2H, d, J=9 Hz), 8.22 (2H, d, J=9 Hz).

REFERENCE EXAMPLE 6

Production of 1-(4-nitrobenzyl) 2-oxo-3-phenylthioglutarate [Compound (6)]

To a suspension of 2.25 g of 3-bromo-2-oxoglutaric acid in 40 ml of dichloromethane was added 1.0 ml of thiophenol while stirring under ice-cooling, followed by addition of 4.15 ml of triethylamine. The reaction mixture was stirred at room temperature for 45 minutes, then the solvent was distilled off, and the residue was distributed to ethyl acetate and 1N-HCl. The ethyl acetate layer was separated, washed with the water and dried (Na$_2$SO$_4$), followed by distilling off the solvent to leave 2.28 g of 2-oxo-3-phenylthioglutaric acid as a pale yellow oily substance.

IR$\nu_{max}^{Neat}$ cm$^{-1}$: 3000(b), 1720, 1470, 1440, 1400, 1280, 1200.

NMR (90 MHz, CDCl$_3$)$\delta$: 2.87 (2H, d, J=8 Hz), 4.73 (1H, t, J=8 Hz), 7.40 (5H, s), 9.4 (2H, b).

To a solution of 2.28 g of this product in 18 ml of dimethylformamide were added 1.43 ml of dicyclohexylamine and 1.56 ml of 4-nitrobenzyl bromide while stirring under ice-cooling. The reaction mixture was stirred at room temperature for 15 hours, followed by diluting with ethyl acetate. Then, precipitating crystals were filtered off. The filtrate was washed with water, dried (Na$_2$SO$_4$), followed by distilling off the solvent. The residue was subjected to a silica gel column chromatography, eluting with hexane-ethyl acetate (1:2→1:3). Fractions containing the object compound were then collected and concentrated under reduced pressure to give 2.25 g of the subject Compound (6) as colorless crystals. Recrystallization from ether-hexane gave colorless prisms, m.p. 119°-120° C.

IR$\nu_{max}^{Nujol}$ cm$^{-1}$: 1745, 1730, 1700, 1520, 1440, 1350, 1280.

NMR (90 MHz, CDCl$_3$)$\delta$: 2.85 (2H, d, J=8 Hz), 4.7 (1H, m), 5.43 (2H, s), 6.7 (1H, b), 7.35 (5H, s), 7.60 (2H, d, J=9 Hz).

Elemental Analysis for C$_{18}$H$_{15}$NO$_7$S: Calcd.: C, 55.52; H, 3.88; N, 3.60. Found: C, 55.49; H, 3.90; N, 3.50.

REFERENCE EXAMPLE 7

Production of 1-(4-nitrobenzyl) 3-ethylthio-2-oxoglutarate [Compound (7)]

To a suspension of 1.00 g of 3-bromo-2-oxoglutaric acid in 20 ml of dichloromethane was added 0.33 ml of ethane thiol while stirring under ice-cooling, followed by addition of 1.83 ml of triehtylamine. The reaction mixture was stirred at room temperature for 3 hours, then the solvent was distilled off. The residue was distributed to ethyl acetate and 1N-HCl. The ethyl acetate layer was separated, washed with water and dried (Na$_2$SO$_4$), followed by distilling off the solvent to give 0.82 g of 3-ethylthio-2-oxoglutaric acid as a pale yellow oily substance.

IR$\nu_{max}^{Neat}$ cm$^{-1}$: 3000(b), 1720, 1400, 1250.

NMR (90 MHz, CDCl$_3$)$\delta$: 1.23(3H, t, J=8 Hz), 2.55(2H, q, J=8 Hz), 3.0(2H, b), 4.4(1H, b), 8.9(2H, b).

To a solution of 0.82 g of this product in 8 ml of dimethylformamide were added 0.65 ml of dicyclohexylamine and 0.70 g of 4-nitrobenzyl bromide while stirring under ice-cooling. The reaction mixture was stirred at room temperature for 3 hours, followed by dilution with ethyl acetate. Then precipitating crystals were filtered off, and the filtrate was washed with water and dried (Na$_2$SO$_4$), followed by distilling off the solvent. The residue was subjected to a silica gel column chromatography, eluting with hexane-ethyl acetate (3:2) and ethyl acetate. Fractions containing the object compound were combined and concentrated under reduced pressure to give 0.61 g of the subject Compound (7) as colorless crystals. Recrystallization from isopropyl ether gave colorless prisms, m.p. 100°-101° C.

IR$\nu_{max}^{Nujol}$ cm$^{-1}$: 1745, 1720, 1700, 1530, 1350, 1255.

NMR (90 MHz, CDCl$_3$)$\delta$: 1.18(3H, t, J=8 Hz), 2.48(2H, q, J=8 Hz), 2.95(2H, m), 4.3(1H, b), 5.41(2H, s), 7.0(1H, b), 7.57(2H, d, J=9 Hz), 8.25(2H, d, J=9 Hz).

Elemental Analysis for C$_{14}$H$_{15}$NO$_7$S: Calcd.: C, 49.26; H, 4.43; N, 4.10. Found: C, 49.32; H, 4.33; N, 3.99.

REFERENCE EXAMPLE 8

Production of 1-t-butyl 2-oxoglutarate [Compound (8)]

To a solution of 5.0 g of 5-oxo-2-tetrahydrofurancarboxylic acid in 100 ml of dichloromethane was added 0.3 ml of concentrated sulfuric acid, to which was further added an excess volume (ca. 50 ml) of isobutene. The reaction mixture was left standing overnight at room temperature under tight sealing, which was poured into a cooled saturated aqueous solution of sodium hydrogencarbonate. The dichloromethane layer was separated, washed with water, dried (Na$_2$SO$_4$) and concentrated to give t-butyl 5-oxo-2-tetrahydrofurancarboxylate as a colorless oily substance.

IR$\nu_{max}^{Neat}$ cm$^{-1}$: 1760.

NMR (60 MHz, CDCl$_3$)$\delta$: 1.50(9H, s), 2.4(4H, m), 4.8(1H, m).

This product was dissolved in 50 ml of absolute methanol, to which was added 100 mg of sodium methylate while stirring under ice-cooling. The reaction mixture was stirred for 3 hours under ice-cooling, which was then concentrated. The residue was poured into a mixture of ethyl acetate and an aqueous solution of ammonium chloride. The resulting ethyl acetate layer was separated and dried (Na$_2$SO$_4$), followed by distilling off the solvent to give 8.2 g of 1-t-butyl 5-methyl 2-hydoxyglutarate as colorless crystals. Recrystallization from hexane yielded colorless prisms, m.p. 36°-37° C.

IR$\nu_{max}^{Nujol}$ cm$^{-1}$: 3450, 1735, 1260, 1230, 1160, 1110.

NMR (90 MHz, CDCl$_3$)$\delta$: 1.47(9H, s), 1.7-2.6(4H, m), 2.87(1H, d, J=5 Hz), 3.63(3H, s), 4.1(1H, m).

Elemental Analysis for C$_{10}$H$_{18}$O$_5$: Calcd.: C, 55.03; H, 8.31. Found: C, 54.60; H, 8.35.

To a solution of 0.39 ml of oxalyl chloride in 12 ml of dichloromethane was added under nitrogen atmosphere at −70° C. while stirring a solution of 0.60 ml of dimethyl sulfoxide in 4 ml of dichloromethane. To the mixture was added a solution of 0.95 g of 1-t-butyl 5-methyl 2-hydoxyglutarate obtained as above in 3.5 ml of dichloromethane. The whole mixture was stirred for 15 minutes at −70° C., to which was added 3.0 ml of triethylamine. The temperature of the reaction mixture was raised to −40° C., and the reaction mixture was poured into ice-water, followed by extraction with dichloromethane. The extract was wahsed with water, dilute acetic acid and water, in sequence, which was then dried (Na$_2$SO$_4$), followed by distilling off the solvent. The residue was subjected to a silica gel column chromatography, eluting with hexane-ethyl acetate (5:1), followed by combining fractions containing the end product. Thus combined eluate was concentrated under reduced pressure to give 0.60 g of 1-t-butyl 5-methyl 2-oxoglutarate as a colorless oily substance.

IR$\nu_{max}^{Neat}$ cm$^{-1}$: 1730, 1370, 1295, 1260, 1200, 1160, 1080.

NMR (90 MHz, CDCl$_3$)δ: 1.57(9H, s), 2.63(2H, t, J=6 Hz), 3.10(2H, s, J=6 Hz), 3.69(3H, s).

In a mixture of 1 ml of tetrahydrofuran and 1 ml of water was dissolved 108 mg of this product, to which was added 0.4 ml of 1N-NaOH while stirring under ice-cooling. The reaction mixture was stirred for 45 minutes under ice-cooling, which was poured into a mixture of water and ethyl acetate. The aqueous layer was separated, to which was added 1N-HCl to adjust its pH to 4, followed by extraction with ethyl acetate. The extract was washed with an aqueous saline solution and dried (Na$_2$SO$_4$). The solvent was then distilled off, and the residue was subjected to a silica gel column chromatography, eluting with hexane-ethyl acetate (3:2→1:2). Fractions containing the end product were combined and concentrated under reduced pressure to give 26 mg of the subject Compound (8) as a colorless oily substance.

IR$\nu_{max}^{Neat}$ cm$^{-1}$: 1740, 1370, 1300, 1255, 1160, 1080.
NMR (90 MHz, CDCl$_3$)δ: 1.53(9H, m), 2.75(4H, b).

REFERENCE EXAMPLE 9

Production of 1-diphenylmethyl 2-oxoglutarate [Compound (9)]

Using 2.93 g of 2-oxoglutaric acid, 4.75 g of diphenylmethyl bromide and 3.63 g of dicyclohexylamine, the same procedure as that in Reference. Example 1 (a) was carried out to give 3.2 g of the subject Compound (9), m.p. 107°–109° C.

IR$\nu_{max}^{KBr}$ cm$^{-1}$: 1730, 1710.

NMR (60 MHz, CDCl$_3$)δ: 2.58–3.17(4H, m), 6.99(1H, s), 7.31–7.54(10H, m)

Elemental Analysis for C$_{18}$H$_{16}$O$_5$: Calcd.: C, 69.22; H, 5.16. Found: C, 69.30; H, 5.18.

REFERENCE EXAMPLE 10

Production of 1-diphenylmethyl 2-oxo-3-phenylthioglutarate [Compound (10)]

In 30 ml of dimethylformamide was dissolved 6.7 g of crude 2-oxo-3-phenylthioglutaric acid obtained by the method of Reference Example 6. To the solution were added 4.0 ml of dicyclohexylamine and 5.0 g of diphenylmethyl bromide at room temperature while stirring. The reaction mixture was stirred at room temperature for 15 hours, followed by dilution with ethyl acetate. Resulting crystalline precipitates were filtered off, and the filtrate was washed with water, then dried (Na$_2$SO$_4$), followed by distilling off the solvent. The residue was subjected to a silica gel column chromatography, eluting with hexane-ethyl acetate (3:1→1:1). Fractions containing the end product were combined and concentrated under reduced pressure to give 3.2 g of the subject Compound (10) as pale yellow crystals. Recrystallization from hexane-ethyl acetate gave colorless needles, m.p. 98°–100° C.

IR$\nu_{max}^{Nujol}$cm$^{-1}$: 1740, 1205, 1180.

NMR (60 MHz, CDCl$_3$)δ: 2.85(2H, d, J=8 Hz), 4.70(1H, t, J=8 Hz), 7.05(1H, s), 7.3(15H, m).

REFERENCE EXAMPLE 11

Production of 1-pivaloyloxymethyl 2-oxoglutarate [Compound (11)]

To a solution of 2.93 g of 2-oxoglutaric acid and 3.48 ml of N,N-diisopropylethylamine in 20 ml of dimethylformamide were added 3.13 g of sodium iodide and 3.02 ml of chloromethyl pivalate. The mixture was stirred at room temperature for 2 hours, followed by dilution with ethyl acetate. Resulting crystalline precipitates were filtered off. The filtrate was concentrated to dryness under reduced pressure. To the residue was added ethyl acetate, which was washed with water, then dried (MgSO$_4$), followed by distilling off the solvent. The residue was subjected to a silica gel column chromatography, eluting with dichloromethane-ethyl acetate (1:1). Fractions containing the end product were combined and concentrated under reduced pressure to give 1.52 g of the subject Compound (11) as a colorless oily substance.

IR$\nu_{max}^{Neat}$ cm$^{-1}$: 2970, 1750, 1710.

NMR (90 MHz, CDCl$_3$)δ: 1.24(9H, s), 2.67–3.19(4H, m), 5.89(2H, s).

REFERENCE EXAMPLE 12

Production of 1-(4-nitrobenzyl) 4-phenyl-2-oxoglutarate [Compound (12)]

To a solution of 4.26 g of 4-phenyl-2-oxoglutaric acid in 30 ml of dimethylformamide were added 2.67 ml of dicyclohexylamine and 2.9 g of 4-nitrobenzyl bromide, and the mixture was stirred at room temperature for 20 hours. The reaction mixture was diluted with ethyl acetate, then resulting crystaline precipitate were filtered off. The filtrate was washed with water and dried (MgSO$_4$), followed by distilling off the solvent. The residue was subjected to a silica gel column chromatography, eluting with hexane-ethyl acetate (2:1→1:1). Fractions containing the end product were combined and concentrated under reduced pressure to give 2.89 g of the subject Compound (12) as pale yellow crystals. Recrystallization from ethyl acetate-hexane gave pale yellow prisms, m.p. 149°–150° C.

IR$\nu_{max}^{KBr}$cm$^{-1}$: 1760, 1740, 1710, 1600.

NMR (90 MHz, CDCl$_3$)δ: 2.5–4.5(3H, m), 5.40(2H, s), 7.30(5H, s), 7.68(2H, d, J=9 Hz), 8.24(2H, d, J=9 Hz).

REFERENCE EXAMPLE 13

Production of 1-(4-nitrobenzyl) 4-benzyl-2-oxoglutarate [Compound (13)]

To a solution of 0.98 ml of diisopropylamine in 13 ml of anhydrous tetrahydrofuran was added under nitrogen atmosphere 4.29 m of 1.5M n-butyl lithium (hexane solution) at −78° C. while stirring. The mixture was stirred for 15 minutes, to which was added, taking 5 minutes, a solution of 1.18 g of 2-oxoglutaric acid dimethylester dimethylketal in 7 ml of anhydrous tetrahydrofuran. The mixture was stirred for 15 minutes, to which was added, taking 5 minutes, a solution of 0.76 ml of benzyl bromide and 0.28 ml of hexamethyl phosphoramide in 7 ml of anhydrous tetrahydrofuran. The mixture was stirred for 30 minutes at −78° C. The temperature of the reaction mixture was raised up to −20° C. under stirring over the period of 2 hours. To the resultant was added a saturated aqueous solution of ammonium chloride, followed by extraction with ethyl acetate. The extract was washed with water and dried (MgSO$_4$), followed by distilling off the solvent. The residue was subjected to a silica gel column chromatography, eluting with hexane-ethyl acetate (5:1→2:1) to give 1.64 g of 4-benzyl-2-oxoglutaric acid dimethylester dimethylketal as a pale yellow oily substance.

IR$\nu_{max}^{Neat}$cm$^{-1}$: 1740, 1600.

NMR (90 MHz, CDCl$_3$)δ: 2.2–3.0(5H, m), 3.07(3H, s), 3.17(3H, s), 3.57(3H, s), 3.68(3H, s), 7.0–7.4(5H, m).

This product was dissolved in 10 ml of methanol, to which was added 15 ml of 3.5M aqueous solution of potassium hydroxide. The mixture was stirred at room temperature for 3.5 hours, followed by distilling off methanol. To the reaction mixture was added 6N HCl to bring the pH to 1, which was saturated with sodium chloride and extracted with ethyl acetate. The extract was washed with an aqueous saline solution and dried (Na$_2$SO$_4$), followed by distilling off the solvent to leave 1.43 g of 4-benzyl-2-oxogulutalate dimethylketal as a yellow oily substance.

This oily substacne was dissolved in 40 ml of tetrahydrofuran, to which was added 40 ml of 1N HCl, followed by stirring at room temperature for 30 minutes. Tetrahydrofuran was then distilled off, and the aqueous layer was saturated with sodium chloride, followed by extraction with ethyl acetate. The extract was washed with an an aqueous saline solution and dried (Na$_2$SO$_4$), from which the solvent was distilled off to leave 1.40 g. of 4-benzyl-2-oxoglutaric acid as a yellow oily substance.

This oily substance was dissolved in 10 ml of dimethylformamide, to which were added 0.83 ml of dicyclohexylamine and 0.90 g of 4-nitrobenzyl bromide. The mixture was stirred at room temperature for 15 hours. To the reaction mixture was added ethyl acetate, then precipitating crystals were filtered off, and the filtrate was washed with water, dried (MgSO$_4$), followed by distilling off the solvent. The residue was subjected to a silica gel column chromatography, eluting with hexane-ethyl acetate (2:1). Fractions containing the end product were combined and concentrated under reduced pressure to give 1.35 g of the subject Compound (13) as a colorless oily substance.

IR$\nu_{max}^{Neat}$ cm$^{-1}$: 3700–3200, 3150–3000, 1760(b), 1600.

NMR (90 MHz, CDCl$_3$)δ: 2.5–3.4(5H, m), 5.30(2H, s), 7.0–7.4(5H, m), 7.45(2H, d, J=9 Hz), 8.18(2H, d, J=9 Hz).

Mass spectrum m/z: 371 (M+).

REFERENCE EXAMPLE 14

Production of of 1-(4-nitrobenzyl) 4-methoxymethyl-2-oxoglutarate [Compound (14)]

To a solution of 2.85 ml of diisopropylamine in 30 ml of anhydrous tetrahydrofuran was added 12.5 ml of 1.5M n-butyryl lithium (hexane solution) at −78° C. under nitrogen streams. The mixture was stirred for 15 minutes, to which was added a solution of 3.45 g of 2-oxoglutaric acid dimethylester dimethylketal in 15 ml of anhydrous tetrahydrofuran, taking 10 minutes, followed by stirring for 15 minutes. To the resultant were added a mixture of 1.32 ml of chloromethylether and 1.36 ml of hexamethylphosphoramide in anhydrous tetrahydrofuran over the period of 10 minutes. The temperature of the mixture was raised to −20° C. over the period of 30 minutes, followed by stirring the mixture at the same temperature for 3 hours. To the reaction mixture was added a saturated aqueous solution of ammonium chloride, and the mixture was subjected to extraction with ethyl acetate. The extract was washed with water and dried (MgSO$_4$), followed by distilling off the solvent. The residue was subjected to a silica gel column chromatography, eluting with hexane-ethyl acetate (2:1) to give 2.28 g of 4-methoxymethyl-2-oxoglutaric acid dimethylester dimethylketal as a pale yellow oily substance.

IR$\nu_{max}^{Neat}$ cm$^{-1}$: 1750.

NMR (90 MHz, CDCl$_3$)δ: 2.02(1H, dd, J=5, 15 Hz), 2.35(1H, dd, J=9, 15 Hz), 2.75(1H, m), 3.23(6H, s), 3.28(3H, s), 3.44(1H, d, J=5 Hz), 3.46(1H, d, J=6 Hz), 3.67(3H, s), 3.77(3H, s).

To a solution of 560 mg of this substance in 4 ml of methanol was added 6 ml of a 1.8M aqueous solution of potassium hydroxide. The mixture was stirred at room temperature for 3 hours. Methanol was distilled off, and the aqueous layer was washed with ether, followed by addition of 6N-HCl to adjust the pH to 1. The resultant was saturated with sodium chloride, which was subjected to extraction with ethyl acetate. The extract was washed with an aqueous saline solution, dried (MgSO$_4$), followed by distilling off the solvent to give 471 mg of 4-methoxymethyl-2-oxoglutaric acid dimethylketal as yellow oily substance. This oily substance was dissolved in 10 ml of tetrahydrofuran, to which was added 10 ml of 1N-HCl, and the mixture was stirred at room temperature for 4 days. Tetrahydrofuran was distilled off, and the aqueous layer was saturated with an aqueous solution of sodium chloride, which was subjected to extraction with ethyl acetate. The extract was washed with an aqueous solution of sodium chloride and dried (MgSO$_4$), followed by distilling off the solvent to leave 397 mg of 4-methoxymethyl-2-oxoglutaric acid as a colorless oily substance.

In 3 ml of dimethylformamide was dissolved 355 mg of this oily substance, to which were added 0.30 ml of dicyclohexylamine and 323 mg of 4-nitrobenzyl bromide, and the mixture was stirred at room temperature for 15 hours. To the reaction mixture was added ethyl acetate, and precipitating crystals were filtered off. The filtrate was washed with water and dried (MgSO$_4$), followed by distilling off the solvent. The residue was subjected to a silica gel column chromatography, eluting with hexane-ethyl acetate (2:1). Fractions containing the end product were combined and concentrated under reduced pressure to give 293 mg of the subject Compound (14) as a yellow oily substance.

IR$\nu_{max}^{Neat}$ cm$^{-1}$: 1750(b), 1600.

NMR (90 MHz, CDCl$_3$)δ: 3.05(3H, m), 3.48(3H, s), 3.6–3.9(2H, m), 5.37(2H, s), 7.52(2H, d, J=9 Hz), 8.21(2H, d, J=9 Hz).

REFERENCE EXAMPLE 15

Production of 2-oxoglutaric acid 1-anilide [Compound (15)]

To an acetonitrile solution (20 ml) of 1.46 g of 2-oxoglutaric acid was added 2.06 g of DCC, and the mixture was stirred at room temperature for 10 minutes. To the resultant was added 930 mg of aniline, followed by stirring at room temperature for 5 hours. White precipitates then formed were filtered off. To the filtrate was added ethyl acetate (40 ml), followed by extraction with an aqueous solution of sodium hydrogencarbonate (30 ml). The pH of the extract was adjusted to 3.0 with 2N HCl, followed by extraction with ethyl acetate. The organic layer was washed with water and dried (MgSO$_4$), followed by distilling off the solvent. The residue was subjected to a silica gel column chromatography, eluting with hexane-ethyl acetate (1:2). Fractions containing the end product were combined and concentrated under reduced pressure to give 390 mg of the subject Compound (15) as colorless crystals, m.p. 192°–193° C.

IR$\nu_{max}^{KBr}$ cm$^{-1}$: 3340, 1700, 1690, 1600, 1540, 1450, 1320.

NMR (90 MHz, CDCl$_3$-d$_6$-DMSO)δ: 2.4 2–2.70(2H, m), 2.90–3.32(2H, m), 7.01–7.90(5H, m).

REFERENCE EXAMPLE 16

Production of 2-oxoglutaric acid 1-pyrrolidine amide [Compound (16)]

Using 584 mg of 2-oxoglutaric acid and 284 mg of pyrrolidine, a reaction was allowed to proceed in the same manner as Reference Example 15 to give 412 mg of the subject Compound (16) as colorless crystals, m.p. 101°–102° C.

IR$\nu_{max}^{KBr}$ cm$^{-1}$: 2970, 1730, 1710, 1600, 1390 1330, 1210, 1170.

NMR (90 MHz, CDCl$_3$)δ: 1.81–2.06(4H, m), 2.65–2.84(2H, m), 3.08–3.27(2H, m), 3.43–3.80(4H, m), 8.60–9.01(1H, m).

REFERENCE EXAMPLE 17

Production of 2-oxoglutaric acid 1-n-propylamide [Compound (17)]

Using 1.46 g of 2-oxoglutaric acid and 0.828 ml of n-propylamine, a reaction was allowed to proceed in the same manner as Reference Example 15 to give 496 mg of the subject Compound (17) as pale yellow crystals, m.p. 79°–81° C.

IR$\nu_{max}^{KBr}$cm$^{-1}$: 3250, 2960, 1730, 1690, 1660, 1530, 1440, 1400.

NMR (90 MHz, CDCl$_3$)δ: 0.81–1.19(3H, t, J=6 Hz), 1.36–1.75(2H, m), 2.58–2.72(2H, m), 3.12–3.34(4H, m), 6.79–7.03(1H, m), 7.91–8.37(1H, m).

REFERENCE EXAMPLE 18

Production of 1-(4-nitrobenzyl) 3-bromo-2-oxoglutarate [Compound (18)]

In 15 ml of anhydrous chloroform was dissolved 1.5 g of 1-(4-nitrobenzyl) 2-oxoglutarate [Compound (1)]. To the solution was added dropwise gradually over the period of 4 hours, while stirring under heating at 50° C., a solution of 0.3 ml of bromine in 5 ml of anhydrous chloroform. To the reaction mixture, after cooling, was added a saturated aqueous saline solution, followed by extraction with dichloromethane. The organic layer was washed with water and dried, (MgSO$_4$), followed by distilling off the solvent under reduced pressure to give 1.89 g of the subject Compound (18) as a pale yellow oily substance.

IR$\nu_{max}^{neat}$cm$^{-1}$: 3300, 1800, 1735, 1605, 1520, 1350.

NMR (90 MHz, CDCl$_3$)δ: 2.67–3.55(2H, m), 5.30–5.38(1H, m), 5.46(2H, s), 7.58 and 8.22(4H, 2d, J=9 Hz), 8.80–9.50(1H, br).

REFERENCE EXAMPLE 19

Production of 1-(4-nitrobenzyl)-5-t-butyl 3-bromo-2-oxoglutarate [Compound (19)]

In 10 ml of anhydrous dichloromethane was dissolved 1.89 g of 1-(4-nitrobenzyl) 3-bromo-2-oxoglutarate (18), to which was added 0.1 ml of concentrated sulfuric acid while stirring under ice-cooling. To the mixture was added, under ice-cooling, 10 ml of liquefied isobutene. The reaction vessel was tightly sealed, and the temperature of the mixture was gradually raised, and the reaction mixture was left standing overnight at room temperature. The resulting solution was neutralized with an aqueous solution of sodium hydrogencarbonate, followed by introducing nitrogen gas to remove excess isobutene. To the residue was added water, and the mixture was subjected to extraction with dichloromethane. The organic layer was washed with water and dried (MgSO$_4$), followed by distilling off the solvent under reduced pressure. The residue was subjected to a silica gel column chromatography, eluting with dichloromethane. Fractions containg the end product were combined and concentrated under reduced pressure to give 1.448 g of the subject Compound (19) as a pale yellow substance.

IR$\nu_{max}^{neat}$cm$^{-1}$: 2980, 1735, 1605, 1525, 1370, 1350.

NMR (90 MHz, CDCl$_3$)δ: 1.42(9H, s), 2.82–3.41 (2H, m), 5.26–5.36(1H, m), 5.46(2H, s), 7.62 and 8.21(4H, 2d, J=9 Hz).

REFERENCE EXAMPLE 20

Production of 1-(4-nitrobenzyl)-5-ethyl 3-bromo-2-oxoglutarate [Compound (20)]

In accordance with the procedure of Reference Example 18, 1.0 g of 1-(4-nitrobenzyl) 2-oxoglutarate [Compound (1)] was subjected to bromination using primary chloroform as the solvent to give 772 mg of the subject Compound (20) as a pale yellow oily substance, while giving as the by-product 368.6 mg of Compound (18).

NMR (90 MHz, CDCl$_3$)δ: 1.23(3H, t, J=6 Hz), 2.89–3.48(2H, m), 4.14(2H, q, J=6 Hz), 5.26–5.4 2(1H, m), 5.46(2H, s), 7.63 and 8.23(4H, 2d, J=9 Hz).

REFERENCE EXAMPLE 21

Production of (3R,4R)-3-tritylamino-4-tritylthio-2-azetidinone [Compound (21)]

In 20 ml of tetrahydrofuran was dissolved 1.0 g of (3R,4R)-3-tritylamino-4-methanesulfonyl-2-azetidinone. To the solution were added, under ice-cooling, a solution of 816 mg of trimethyl mercaptane in 25 ml of tetrahydrofuran and 2.83 ml of a 1N aqueous solution of sodium hydroxide, and the mixture was stirred at room temperature for 25 minutes. The reaction mixture was concentrated under reduced pressure. To the residue was added 30 ml of water, and the mixture was subjected to extraction with 40 ml of ethyl acetate. The aqueous layer was concentrated under reduced pressure, and the resulting crystalline precipitates were collected by filtration. The filtrate was dried (MgSO$_4$), and the solvent was distilled off under reduced pressure. The residue was subjected to a silica gel column chromatography, eluting with ethyl acetate-n-hexane (1:5), and the fractions containing the end product were combined and concentrated under reduced pressure to give 486.5 mg of the subject compound (25) as white crystals.

IR $\nu_{max}^{KBr}$ cm$^{-1}$: 3400, 3060, 1760, 1490, 1445, 1180, 745, 700.

NMR (90 MHz, CDCl$_3$)δ: 2.89 (1H, d, J=8 Hz), 3.93 (1H, s), 4.39 (1H, d, J=5 Hz), 4.56 (1H, dd, J=5 Hz, 8 Hz), 7.14–7.59 (30H, m).

REFERENCE EXAMPLE 22

Production of
(3R,4R)-3-phenylacetamido-4-tritylthio-2-azetidinone
[Compound (22)]

In 10 ml of acetone was dissolved 302 mg of Compound (21) obtained in Reference Example 21. To the solution was added, under ice-cooling, 114 mg of p-toluene sulfonic acid monohydrate, followed by stirring at room temperature for one hour. The reaction mixture was concentrated under reduced pressure, to which was added ether to cause crystallization. The crystals were collected by filtration and washed with 10 ml of ether. The resulting white crystals were dissolved in 10 ml of dichloromethane, to which were added, under ice-cooling, 0.21 ml of triethylamine and 0.09 ml of phenylacetyl chloride, followed by stirring for one hour. The reaction mixture was concentrated under reduced pressure, and the residue was subjected to a silica gel column chromatography, eluting with ethyl acetate-n-hexane (1:1). Fractions containing the end product were combined and concentrated under reduced pressure to give 204 mg of the subject Compound (22) as white powders.

IR $\nu_{max}^{KBr}$ cm$^{-1}$: 3270, 3050, 1765, 1665, 1495, 1440, 740, 700.

NMR (90 MHz, CDCl$_3$)δ: 3.62 (2H, s), 4.63 (1H, d, J=5 Hz), 4.76 (1H, br.s), 5.43 (1H, dd, J=5 Hz, 9 Hz), 6.47 (1H, d, J=9 Hz), 7.27 (20H, s).

REFERENCE EXAMPLE 23

Production of
(3R,4R)-3-(4-nitro)benzyloxycarbonylamino-4-tritylthio-2-azetidinone [Compound (23)]

In 130 ml of acetone was dissolved 3.9125 g of Compound (21) obtained in Reference Example 21. To the solution was added, under ice-cooling, 1.482 g of p-toluenesulfonic acid monohydrate, followed by stirring at room temperature for one hour. The reaction mixture was concentrated under reduced pressure. To the residue was added 150 ml of ether to cause crystallization. Resulting crystals were collected by filtration and washed with 50 ml of ether to thereby obtain 3.211 g of p-toluene sulfonate of (3R,4R)-3-amino-4-tritylthio-2-azetidinone as white crystals.

IR $\nu_{max}^{KBr}$ cm$^{-1}$: 3050, 1760, 1495, 1445, 1185, 1120, 1030, 1010, 740, 700, 680.

NMR (90 MHz, d$_6$-DMSO)δ: 2.27 (3H, s), 4.43 (1H, d, J=5 Hz), 4.53–4.61 (1H, m), 7.07 (2H, d, J=8 Hz), 7.198–7.37 (15H, m), 7.48 (2H, d, J=8 Hz) 8.81 (3H, br.s), 8.99 (1H, s).

In 10 ml of tetrahydrofuran was suspended 799 mg of the p-toluene sulfonate obtained as above, to which were added, under ice-cooling, 10 m of water and 277 mg of sodium hydrogencarbonate. To this solution was added dropwise under ice-cooling a solution of 388 mg of 4-nitrobenzyloxycarbonyl chloride in 3 ml of tetrahydrofuran, followed by stirring for 40 minutes. The reaction mixture was concentrated under reduced pressure, which was subjected to extraction with ethyl acetate. The organic layer was washed with water and dried (MgSO$_4$), followed by distilling off the solvent under reduced pressure. The residue was subjected to a gel column chromatography, eluting with ethyl a n-hexane (1:1), followed by collecting fractions c ing the end product and concentrating under re pressure to give 760 mg of the subject Compour as white crystals.

IR $\nu_{max}^{KBr}$ cm$^{-1}$: 3290, 3060, 1775, 1730, 1525 1250, 745, 700.

NMR (90 MHz, CDCl$_3$)δ: 4.66 (1H, J=: 5.03–5.42 (4H, m), 6.13 (1H, d, J=9 Hz), 7.15–7. H, m). 7.49 (2H, d, J=9 Hz), 8.10 (2H, d, J=9 H

REFERENCE EXAMPLE 24

Production of
(3R,4R)-1-(t-butyldimethyl)silyl-3-phenylacetami
tritylthio-2-azetidinone [Compound (24)]

In 5 ml of N,N-dimethylformamide were diss 456 mg of Compound (22) obtained in Reference 187 mg of t-butyldimethylchlorosilane. To the so was added dropwise, while stirring under ice-cc 153 μl of triethylamine, followed by stirring at temperature for 14.5 hours. To the mixture were fi added 86 mg of t-butyldimethylchlorosilane and of triethylamine, followed by stirring at room ten ture for 2.5 hours. To the reaction mixture was adc ml of water, which was subjected to extraction w ml of ethyl acetate. The organic layer was washec water and dried (MgSO$_4$), followed by distilling c solvent. The residue was subjected to a silica ge umn chromatography, eluting with n-hexane-ethy tate (1:1). Fractions containing the end product combined and concentrated under reduced pressu give 451.5 mg of the subject Compound (24) as powders.

IR $\nu_{max}^{KBr}$ cm$^{-1}$: 3300, 2930, 2855, 1760, 1685, 1250, 840, 820, 740, 700.

NMR (90 MHz, CDCl$_3$)δ: 0.19 (6H, s), 0.86 (9 3.12 (1H, d, J=15 Hz), 3.39 (1H, d, J=15 Hz), 4.7ε d, J=5 Hz), 5.41 (1H, dd, J=5 Hz, 9 Hz), 5.95 (1 J=9 Hz), 7.10–7.38 (20H, m).

REFERENCE EXAMPLE 25

Production of
(3R,4R)-1-(t-butyldimethyl)silyl-3-phenylacetamic
mercapto-2-azetidinone [Compound (25)]

In 3 ml of methanol was dissolved 100 mg of ( pound (24) obtained in Reference Example 24. T solution was added dropwise a solution of 70 n mercuric acetate in 2 ml of methanol at −53° ( −47° C. The mixture was stirred at −53° C. to −4 for 70 minutes, followed by introducing hydroger fide gas at −70° C. or below for 5 minutes, followe introducing nitrogen gas for 30 minutes to elim hydrogen sulfide gas. The reaction mixtures was centrated under reduced pressure, and the residue dissolved in dichloromethane. Insoluble materials filtered off, and the filtrate was concentrated υ reduced pressure. The residue was subjected to a gel column chromatography, eluting with n-he: ethyl acetate (7:3). Fractions containing the end ↑ uct were combined and concentrated under red pressure to give 48 mg of the subject Compound (2 an oily product.

IR $\nu_{max}^{neat}$ cm$^{-1}$: 3300, 2960, 2940, 2860, 2550, 1740, 1680, 1540, 1255, 1020, 840, 820.

NMR (90 MHz, CDCl$_3$)δ: 0.26 (6H, s), 0.94 (9H, s), 1.81 (1H, d, J=8 Hz), 3.61 (2H, s), 4.96 (1H, dd, J=5 Hz, 8 Hz), 5.45 (1H, dd, J=5 Hz, 9 Hz), 6.85 (1H, d, J=9 Hz), 7.28 (5H, s).

REFERENCE EXAMPLE 26

Production of (3R,4R)-3-phenylacetamido-4-mercapto-2-azetidinone [Compound (26)]

In 1.2 ml of acetone was dissolved 27 mg of Compound (25) obtained in Reference Example 25. To the solution was added 0.5 ml of 1N HCl, and the mixture was stirred at room temperaure for one hour. To the reaction mixture was added under ice-cooling 20 ml of water, and the mixture was subjected to extraciton with 30 ml of dichloromethane. The organic layer was concentrated under reduced pressure to give 16.5 mg of the subject Compound (26) as white crystals.

IR $\nu_{max}^{KBr}$ cm$^{-1}$: 3270, 2540, 1780, 1760, 1725, 1660, 1550, 1250, 980, 700.

NMR (90 MHz, d$_6$-DMSO)δ: 2.89 (1H, d, J=9 Hz), 3.52 (2H, s), 4.98 (1H, dd, J=5 Hz, 9 Hz), 5.25 (1H, dd, J=5 Hz,9 Hz), 7.31 (5H, s), 8.73 (1H, br.s), 8.85 (1H, d).

REFERENCE EXAMPLE 27

Production of (3R,4R)-1-(t-butyldimethyl)silyl-3-(4-nitro)benzyloxycarbonylamino-4-tritylthio-2-azetidinone [Compound (27)]

In 4 ml of N,N-dimethylformamide were dissolved 367 mg of Compound (23) obtained in Reference Example 23 and 133 mg of t-butyldimethylchlorosilane. To the solution was added dropwise, while stirring under ice-cooling, 109 μl of triethylamine, followed by stirring at room temperature for 14 hours. To the resultant were further added 62 mg of t-butyldimethylchlorosilane and 47 μl of triethylamine, and the mixture was stirred at room temperature for 3 hours. To the resultant was added 40 ml of water, which was subjected to extraction with 40 ml of ethyl acetate. The organic layer was washed with water and dried (MgSO$_4$), followed by distilling off the solvent under reduced pressure. The residue was subejcted to a silica gel column chromatography, eluging with n-hexane-ethyl acetate (4:1). Fractions containing the end product were combined and concentrated under reduced pressure to give 286 mg of the subject Compound (27) as a white powdery product.

IR $\nu_{max}^{KBr}$ cm$^{-1}$: 2960, 2930, 2860, 1765, 1730, 1530, 1345, 1250, 740, 700.

NMR (90 MHz, CDCl$_3$)δ: 0.30 (6H, s), 0.96 (9H, s), 4.70–5.31 (5H, m), 7.18–7.49 (17H, m), 8.15 (2H, d, J=9 Hz).

REFERENCE EXAMPLE 28

Production of (3R,4R)-3-[(2R)-2-(4-ethyl-2,3-dioxo-1-piperazinecarboxamido)phenylacetamido]-4-tritylthio-2-azetidinone [Compound (28)]

In 10 ml of dichloromethane was suspended 383 mg of (2R)-2-(4-ethyl-2,3-dioxo-1-piperazinecarboxamido)-phenylacetic acid, to which were added dropwise under ice-cooling 165 μl of chlorotrimethylsilane and 181 μl of triethylamine, followed by stirring at room temperature for 30 minutes. The reaction mixture was cooled to −25° C. to −20° C., to which were added 101 μl of N,N-dimethylformamide and 78 μl of trichloromethyl chloroformate, followed by stirring at −25° C. to 20° C. for 2 hours. The reaction mixture was cooled to −70° C., to which were added 186 μl of pyridine, 533 mg of p-toluenesulfonate of (3R,4R)-3-amino-4-tritylthio-2-azetidinone and 1 ml of propylene oxide, then the cooling bath (dry ice-acetone bath) was removed. The temperature of the mixture was raised to room temperature over the period of one hour. The reaction mixture was concentrated under reduced pressure. The residue was subjected to a silica gel column chromatography, eluting with ethyl acetate. Fractions containing the end product were combined and concentrated under reduced pressure to give 496 mg of the subject Compound (28) as a white powdery product.

IR $\nu_{max}^{KBr}$ cm$^{-1}$: 3300, 1780, 1770, 1720, 1690, 1510, 1360, 1180, 740, 700.

NMR (90 MHz, CDCl$_3$)δ: 1.18 (3H, t, J=7 Hz), 3.22–3.93 (6H, m), 4.54 (1H, d, J=5 Hz), 5.21 (1H, br.s), 5.47–5.62 (2H, m), 7.17–7.57 (20H, m), 8.03 (1H, d, J=9 Hz), 10.06 (1H, d, J=6 Hz).

REFERENCE EXAMPLE 29

Production of (3R,4R)-1-(t-butyldimethyl)silyl-3-[(2R)-2-(4-ethyl-2,3-dioxo-1-piperazinecarboxamide)phenylacetamido]-4-tritylthio-2-azetidinone [Compound (29) ]

In 3 ml of dichloromethane was 200 mg of Compound (28) obtained in Reference Example, to which was added 47 μl of of triethylamine under ice-cooling. To the mixture was added dropwise, while stirring under ice-cooling, 70 μl of t-butyldimethylsilyl trifluoromethane sulfonate in nitrogen streams, followed by stirring at the same temperature for one hour. The reaction mixture was poured into 20 ml of water, which was extracted with dichloromethane. The organic layer was washed with a saturated aqueous solution of sodium hydrogen-carbonate and dried (MgSO$_4$), followed by distilling off the solvent. The residue was subjected to a silica gel column chromatography, eluting with ethyl acetate. Fractions containing the end product were combined and concentrated under reduced pressure to give 183.5 mg of the subject Compound (29) as a white powdery product.

IR $\nu_{max}^{KBr}$ cm$^{-1}$: 3300, 2930, 1765, 1730, 1695, 1500, 1360, 1250, 1180, 700.

NMR (90 MHz, CDCl$_3$)δ: 0.12 (6H, s), 0.91 (9H, s), 1.24 (3H, t, J=8 Hz), 3.26–4.40 (7H, m), 4.73 (1H, d, J=5 Hz), 5.48–5.63 (2H, m), 7.02–7.40 (20H, m), 10.00 (1H, d, J=7 Hz).

REFERENCE EXAMPLE 30

Production of (3R,4R)-3-[(2R)-2-(4-ethyl-2,3-dioxo-1-piperazinecarboxamido)-2-phenylacetamido]-2-azetidinone-4-thiol [Compound (30)]

In 35 ml of methanol was dissolved 1.0 g of Compound (29) obtained in Reference Example 29. This solution was cooled to −55° C. to −50° C., to which was then added dropwise over the period of 15 minutes, a solution of 534 mg of mercuric acetate in 14 ml of methanol, and the mixture was stirred. To the resultant were added, 43 minutes later, a solution of 267 mg of mercuric acetate in 7 ml of methanol and, 82 minutes later, a solution of 134 mg of mercuric acetate in 4 ml of methanol, in sequence. The mixture was stirred for 2 hours and 10 minutes in total, while maintaining at −55° C. to −50° C. To the reaction at temperatures not higher than −50° C., followed by introducing nitrogen gas for 20 minutes. The solvent of the reacition mixture was distilled off under reduced pressure. The residue was dissolved in dichloromethane, and insoluble materials were filtered off. The filtrate was concentrated to give 1.037 g of the subject Compound (30) in a crude state.

REFERENCE EXAMPLE 31

Production of 1-(4-bromo)benzyl 3-bromo-2-oxoglutarate [Compound (31)]

In 25 ml of dry chloroform was dissolved 3.0 g of 1-(4-bromo)benzyl 2-oxoglutarate sythesized in accordance with the procedure of Reference Example 3. To the solution was added dropwise, while stirring under heating at 50°~60° C., a solution of 0.54 ml of bromine in 10 ml of dry chloroform over the period of 6 hours. The reaction mixture was cooled to room temperature, to which was added 100 ml of dichloromethane, followed by washing with a saturated aqueous saline solution and drying (MgSO$_4$). The solvent was then distilled off under reduced pressure to give 3.6615 g of the subject Compound (31) as a pale yellow oily substance.

IR $\nu_{max}^{neat}$ cm$^{-1}$: 3360, 3000, 1800, 1740, 1595, 1490, 1405, 1280, 1210, 1070, 1010.

NMR (90 MHz, CDCl$_3$)δ: 2.88–3.50 (2H, m), 5.19–5.41 (3H, m), 7.26 and 7.51 (4H, 2 d, J=9 Hz), 9.43 (1H, br).

REFEREMCE EXAMPLE 32

Production of (3S,4S)-3-benzyloxycarbonylamino-4-iodomethyl-2-azetidinone [Compound (32)]

In 80 ml of dichloromethane were dissolved 1.9 g of (3S,4S)-3-benzyloxycarbonylamino-4-hydroxymethyl-2-azetidinone and 1.15 g of triethylamine. To the solution was added dropwise under ice-cooling 5 ml of a dichloromethane solution containing 1.13 g of methanesulfonyl chloride. The mixture was stirred for 40 minutes under ice-cooling, followed by washing with water and drying (MgSO$_4$). The solvent was distilled off under reduced pressure, and the residue was dissolved in 150 ml of 2-butanone. To this solution was added 4.28 g of sodium iodide, and the mixture was refluxed for 3.5 hours under heating. The solvent was distilled off under reduced pressure. To the residue were added 100 ml of ethyl acetate and 50 ml of tetrahydrofuran. The mixture was washed with a 10%(w/w) aqueous solution of sodium hydrogensulfite then with a saturated aqueous saline solution, followed by drying (MgSO$_4$). The solvent was distilled off under reduced pressure, and the resultant crystals were washed with ether, followed by collecting by filtration to yield 1.835 g of the subject Compound (32).

IR $\nu_{max}^{KBr}$ cm$^{-1}$: 3320, 1768, 1727, 1693, 1528, 1258.

NMR (90 MHz, d$_6$-DMSO)δ: 3.22 (2H, m), 3.99 (1H, m), 4.91 (1H, dd, J=4 Hz, 10 Hz), 5.05 (2H, s), 7.33 (5H, s), 8.00 (1H, d, J=10 Hz), 8.48 (1H, s).

REFERENCE EXAMPLE 33

Production of (3S,4S)-3-benzyloxycarbonylamino-4-tritylthiomethyl-2-azetidinone [Compound (33)]

In 30 ml of N,N-dimethylformamide was dissolved 1.06 g of trimethyl mercaptan. To this solution was added 0.147 g of sodium hydride (60% oil) under ice-cooling in nitrogen streams, followed by stirring at room temperature for 5 minutes. To the mixture was added 1.2 g of (3S,4S)-3-benzyloxycarbonylamino-4-iodomethyl-2-azetidinone, followed by stirring at 60° C. to 70° C. for 1.5 hour. The reaction mixture was cooled to ro m temperature, to which was added 100 ml of ethyl acetate, followed by washing with water and a saturated aqueous saline solution. The resultant was dried (MgSO$_4$), and the solvent was distilled off under reduced pressure. The residue was subjected to a silica gel column chronmatography, eluting with ethyl acetate-hexane (2:3). Fractions containing the end product were then combined and concentrated under reduced pressure to give 1.38 g of the subject Compound (33) as powders.

IR $\nu_{max}^{KBr}$ cm$^{-1}$: 3275, 1762, 1715, 1243.

NMR (90 MHz, CDCl$_3$)δ: 2.40 (2H, m), 3.47 (1H, m), 4.93 (1H, m), 5.06 (2H, s), 5.36 (1H, d, J=9 Hz), 7.15–7.50 (20H, m).

REFERENCE EXAMPLE 34

Production of silver salt of (3S,4S)-3-benzyloxycarbonylamino-2-azetidinone-4-thiol [Compound (34)]

In 20 ml of methanol was dissolved 1.19 g of Compound (33) obtained in Reference Example 33. To this solution were added 30 ml of a methanol solution containing 0.439 g of silver nitrate and 0.204 g of pyridine. The mixture was stirred at room temperature for 4 hours. Resulting precipitates were collected by filtration, washed with methanol and dried under reduced pressure to give 0.88 g of the subject Compound (34).

IR $\nu_{max}^{KBr}$ cm$^{-1}$: 3275, 1763, 1681, 1255.

REFERENCE EXAMPLE 35

Production of 4-nitrobenzyl (6S,7S)-2-hydroxy-3-(t-butyloxycarbonylmethyl)-7-benzyloxycarbonylamino-8-oxo-4-thia-1-azabicyclo[4,2,0]octane-2-carboxylate [Compound (35a)] and 1-(4-nitrobenzyl)-5-(t-butyl) 3-[(3S,4S)-3-benzyloxycarbonylamino-2-azetidinon-4-yl]methylthio-2-oxoglutarate [Compound (35b)]

In 10 ml of dichloromethane was suspended 0.1 g of Compound (34) obtained in Reference Example 34. To the suspension was introduced under ice-cooling hydrogen sulfide gas for 2 hours. Insoluble materials were filtered off, and the filtrate was concentrated under reduced pressure. The residue was dissolved in a mixture of 3 ml of acetone and 2 ml of hexamethyl phosphoramide. To the solution was added in nitrogen streams 0.168 g of Compound (19) obtained in Reference Example 19, and the mixture was stirred at room temperature for 2.5 hours. To the reaction mixture was added ethyl acetate (25 ml), which was washed with water, then with a saturated aqueous saline solution, followed by drying (MgSO$_4$). The solvent was distilled off under reduced pressure, and the residue was subjected to a silica gel column chromatography, eluting with ethyl acetate-hexane (2:3→1:1). Fractions containing the end product were combined and concentrated under reduced pressure to give 46 mg of the subject Compound (35a) as an oily substance then 81 mg of a mixture of the subject Compound (35a) and the subject Compound (35b) at the ratio of 3:5 as an oily substance.

Compound (35a)

IR $\nu_{max}^{Neat}$ cm$^{-1}$: 3380, 1768, 1730, 1525, 1346, 1255.

NMR (90 MHz, CDCl$_3$)δ: 1.41 (9H, s), 2.28 (2H, m), 2.45–3.03 (2H, m), 3.86 (1H, dd, J=6 Hz, 7 Hz), 4.12 (1H, m), 4.36 (1H, s), 4.82 (1H, dd, J=4 Hz, 6 Hz), 5.07 (2H, s), 5.35 (2H, ABq, J=12 Hz, 20 Hz), 5.57 (1H, d, J=6 Hz), 7.31 (5H, s), 7.56 (2H, d, J=9 Hz), 8.18 (2H, d, J=9 Hz).

REFERENCE EXAMPLE 36

Production of 1-(4-nitrobenzyl) 3-[(3S,4S)-3-benzyloxycarbonylamino-2-azetidinon-4-yl]methylthio-2-oxoglutarate [Compound (36)]

In 1.5 ml of dichloromethane was dissolved 0.282 g of a mixture of Compound (35a) and Compound (35b) obtained in Reference Example 35. To the solution were added under ice-cooling 0.5 ml of anisole and 5 ml of trifluoroacetic acid. The mixture was stirred at the same temperature for 2.5 hours. The solvent was distilled off under reduced pressure, and the residue was washed with 10 ml portion each of hexane three times, followed by distilling off the solvent under reduced pressure to give a crude product of the subject Compound (36). This product was used in the following Example 1 without purification.

REFERENCE EXAMPLE 37

Production of (3S,4S)-4-hydroxymethyl-3-(4-nitrobenzyloxycarbonylamino)-2-azetidinone [Compound (37)]

In 120 ml of ethanol was dissolved 5 g of (3S,4S)-3-benzyloxycarbonylamino-4-hydroxymethyl-2-azetidinone. To the solution was added 0.5 g of 10% palladium-carbon, which was stirred for one hour while introducing hydrogen gas. Insoluble materials were filtered off, and the filtrate was concentrated under reduced pressure. The residue was dissolved in a mixture of 100 ml of tetrahydrofuran and 50 ml of water. To this solution were added under ice-cooling 2.86 g of sodium hydrogencarbonate and 5.18 g of carbo(4-nitro)benzoxy chloride, and the mixture was stirred for one hour at the same temperature. To the reaction mixture were added 200 ml of ethyl acetate, 50 ml of methanol and 50 ml of a saturated aqueous saline solution. The organic layer was separated. The aqueous layer was subjected to extraction with 50 ml of ethyl acetate, and the extract was combined with the organic layer, which was washed with a saturated aqeuous saline solution and dried (MgSO$_4$). The solvent was distilled off under reduced pressure. The resulting crystals were washed with ether and collected by filtration to give 5.75 g of the subject Compound (37).

IR $\nu_{max}^{KBr}$ cm$^{-1}$: 3460, 3298, 1755, 1715, 1705, 1563, 1542, 1352, 1276.

NMR (90 MHz, DMSO—d$_6$) δ: 3.57 (3H, m), 4.73(1H, t, J=5 Hz), 4.87 (1H, dd, J=4 Hz, 9 Hz), 5.20(2H, s), 7.62(2H, d, J=9 Hz), 7.88(1H, d, J=9 Hz), 8.18(1H, s) 8.23(2H, d, J=9 Hz).

REFERENCE EXAMPLE 38

Production of (3S,4S)-4-iodomethyl-3-(4-nitrobenzyloxycarbonylamino)-2-azetidinone [Compound (38)]

In a mixture of 20 ml of N,N-dimethylformamide and 30 ml of tetrahydrofuran were dissolved 6.08 g of Compound (37) obtained in Reference Example 38 and 3.13 g of triethylamine. To this solution was added dropwise under ice-cooling 8 ml of a tetrahydrofuran solution containing 3.07 g of methanesulfonyl chloride. The reaction mixture was stirred for one hour under ice-cooling, to which was added 200 ml of ethyl acetate, followed by washing with 80 ml each portion of water three times and drying (MgSO$_4$). The solvent was distilled off under reduced pressure. The residue was dissolved in 300 ml of 2-butanone, to which was added 10.98 g of sodium iodide, followed by refluxing under heating for 3 hours. The solvent was distilled off under reduced pressure. To the residue were added 200 ml of ethyl acetate and 700 ml of tetrahydrofuran. The mixture was washed with a 10% aqueous solution of sodium hydrogensulfite then with a saturated aqueous saline solution, followed by drying (MgSO$_4$). The solvent was distilled off under reduced pressure to leave crystals, which were washed with ether and collected by filtration to obtain 7.037 g of the subject Compound (38), m.p. 208°–209° C. (decomp.)

IR $\nu_{max}^{KBr}$ cm$^{-1}$: 3330, 1762, 1730, 1690, 1543, 1515, 1326, 1283, 1261.

NMR (90 MHz, DMSO—d$_6$) δ: 3.26 (2H, m), 4.00 (1H, m), 4.93 (1H, dd, J=4 Hz, 10 Hz), 7.62 (2H, d, J=10 Hz), 8.25 (2H, d, J=9 Hz), 8.57 (1H, s).

REFERENCE EXAMPLE 39

Production of (3S,4S)-3-(4-nitrobenzyloxycarbonylamino)-4-tritylthiomethyl-2-azetidinone [Compound (39)]

In 80 ml N,N-dimethylformamide was dissolved 4.42 g of trityl mercaptan. To this solution was added 0.61 g of sodium hydride (60% oil) under ice-cooling in nitrogen streams, followed by stirring at room temperature for 5 minutes. To the mixture was then added 5 g of of Compound (38) obtained in Reference Example 38, followed by stirring for one hour at 55° to 60° C. The reaction mixture was cooled to room temperature, to which was added 400 ml of ethyl acetate, followed by washing with water and a saturated aqueous saline solution and drying (MgSO$_4$). The solvent was distilled off under reduced pressure, and the residue was subjected to a silica gel column chromatography, eluting with ethyl acetate-hexane (3:2), followed by combining fractions containing the end product and concentrating under reduced pressure to give 5.77 g of the subject Compound (39) as powders.

IR $\nu_{max}^{KBr}$ cm$^{-1}$: 3300, 1760, 1728, 1522, 1346. NMR (90 MHz, CDCl$_3$) δ: 2.39 (2H, d, J=7 Hz), 3.40 4.89 (1H, dd, J=4 Hz, 9Hz), 5.13 (2H, ABq, J=13 Hz, 15 Hz), 5.93 (1H, s), 6.05 (1H, d, J=9 Hz), 7.10~7.53 (17 H, m), 8.08 (2H, d, J=9 Hz).

REFERENCE EXAMPLE 40

Production of 4-nitrobenzyl(6S,7S)-2-hydroxy-3-ct-butyloxycarbonylmethyl)-7-(4-nitrobenzyloxycarbonylamino)-8-oxo-4-thia-1-azabicyclo[4,2,0]octane-2-carboxylate [Compound (40a)] and 1-(4-nitrobenzyl)-5-(t-butyl) 3-[(3S,4S)-3-(4-nitro)benzyloxycarbonylamino-2-azetidinon-4-yl]methylthio-2-oxoglutarate [Compound (40b)]

In a mixture of 100 ml of dichloromethane and 150 ml of methanol was dissolved Compound (39) obtained in Reference Example 39. To this solution were added 100 ml of a methanol solution containing 1.5 g of silver nitrate and 0.7 g of pyridine. The mixture was stirred for 1.5 hour at room temperature. Resulting precipitates were collected by filtration and washed with methanol.

The precipitates were suspended in a mixture of 100 ml of dichloromethane and 100 ml of methanol. This suspension was vigorously stirred for 30 minutes while introducing hydrogen sulfide gas under ice-cooling. Insoluble materials were filtered off, and the filtrate was concentrated under reduced pressure. The residue was dissolved in a mixture of 40 ml of acetone and 10 m of hexamethylphosphoramide. To the solution were added under nitrogen streams 3.05 g of Compound (19) obtained in Reference Example 19 and 0.699 g of pyridine. The mixture was then stirred for one hour at room temperature. To the reaction mixture was added 150 ml of ethyl acetate, and the mixture was washed with water then with a saturated aqueous saline solution, followed by drying (MgSO$_4$). The solvent was distilled off under reduced pressure. The residue was subjected to a silica gel column chromatography, eluting ethyl acetone-hexane (3:2). Fractions containing the end product were combined and concentrated under reduced pressure to give 2.64 g of a mixture of the subject Compound (40a) and Compound (40b) at the ratio of 1:1 as an oily substance.

IR $\nu_{max}^{Neat}$ cm$^{-1}$: 3325, 1755, 1728, 1524, 1347, 1247.

REFERENCE EXAMPLE 41

Production of 1-(4-nitrobenzyl) 3-[(3S,4S)-3-(4-nitrobenzyloxycarbonylamino)-2-azetidinon-4-yl]methylthio-2-oxoglutarate [Compound (41)]

In 3 ml of anisole was dissolved 2.44 g of the mixture of Compound (40a) and Compound (40b) obtained in Reference Example 40. To the solution was added under ice-cooling 30 ml of trifluoroacetic acid, and the mixture was stirred at the same temperature for 5 hours. The solvent was distilled off under reduced pressure. The residue was washed with a 100 ml each portion of hexane, and the solvent was distilled off under reduced pressure to give the subject Compound (41) in a crude state, which was used in the following Example 2 without purification.

REFERENCE EXAMPLE 42

Production of 1-(4-nitrobenzyl)-5-(t-butyl)2-oxoglutarate [Compound (42)]

In 600 ml of dichloromethane was dissolved 15 g of 1-(4-nitrobenzyl)2-oxoglutarate [Compound (1)], to which were added under ice-cooling 80 ml of liquefied isobutene and 1 ml of sulfuric acid. The mixture was left standing at room temperature for 2 days in a tightly sealed vessel. The reaction mixture was neutralized with an aqueous solution of sodium hydrogencarbonate, followed by removing an excess volume of isobutene while introducing nitrogen gas. The organic layer was separated, washed with water and dried (MgSO$_4$). The solvent was distilled off, and the residue was subjected to a silica gel column chromatography, eluting with ethyl acetate-hexane (1:3). Fractions containing the end product were combined and concentrated under reduced pressure to give 14.93 g of the subject Compound (42) as crystals.

IR $\nu_{max}^{KBr}$ cm$^{-1}$: 1750, 1723, 1513, 1345, 1270, 1238, 1210, 1161, 1077.

NMR (90 MHz, CDCl$_6$) δ: 1.43 (9H, s), 2.60 (2H, t, J=6 Hz), 3.10 (2H, t, J=6 Hz), 5.40 (2H, s), 7.55 (2H, d, J=9 Hz), 8.23 (2H, d, J=9 Hz).

REFERENCE EXAMPLE 43

Production of diethyl 3-methylene-2-oxoglutarate [Compound (43)]

To 1 g of diethyl 2-oxoglutarate acid were added under ice-cooling 2.5 ml of N,N,N',N'-tetramethyldiaminomethane and 2.5 ml of acetic anhydride, and the mixture was stirred at room temperature for 15 hours. The solvent was distilled off under reduced pressure, and the residue was subjected to a silica gel column chromatography, eluting with ethyl acetate-hexane (1:4). Fractions containing the end product were combined and concentrated under reduced pressure to give 0.744 g of the subject Compound (43) as an oily substance.

IR $\nu_{max}^{KBr}$ cm$^{-1}$: 1735, 1635, 1250, 1130, 1045.

NMR (90 MHz, CDCl$_3$) δ: 1.24 (3H, t, J=7 Hz), 1.36 (3H, t, J=7 Hz), 3.36 (2H, s), 4.14 (2H, ABq, J=7 Hz), 4.36 (2H, ABq, J=7 Hz), 6.27 (1H, s), 6.37 (1H, s).

REFERENCE EXAMPLE 44

Production of 1-(4-nitrobenzyl)-5-(t-butyl) 3-methylene-2-oxoglutarate [Compound (44)]

In 0.55 ml of N,N,N',N'-tetramethyldiaminomethane was suspended 0.337 g of Compound (42) obtained in Reference Example 42 in nitrogen streams at −20° C. To the suspension was added 0.47 ml of acetic anhydride, and the mixture was stirred at room temperature for 6 hours. The solvent was distilled off under reduced pressure, and the residue was subjected to a silica gel column chromatography, eluting with ethyl acetate-hexane (1:2). Fractions containing the end product were combined and concentrated under reduced pressure to give 0.318 g of the subject Compound (44) as crystals, m.p. 86°-87° C.

IR $\nu_{max}^{KBr}$ cm$^{-1}$: 1752, 1720, 1683, 1515, 1350.

NMR (90 MHz, CDCl$_3$) δ: 1.43 (9H, s), 3.33 (2H, s), 5.43 (2H, s), 6.21 (1H, s), 6.30 (1H, s), 7.60 (2H, d, J=9 Hz), 8.27 (2H, d, J=9 Hz).

REFERENCE EXAMPLE 45

Production of (4-nitro)benzyl (6R,7R)-3-t-butyloxycarbonylmethyl-2-hydroxy-8-oxo-7-phenoxyacetamido-5-thia-1-azabicyclo[4,2,0]octane-2-carboxylate [Compound (45a)] and 1-(4-nitrobenzyl-5-(t-butyl) 3-[(3R,4R)-3-phenoxyacetamido-2-azetidinon-4-yl]thiomethyl-2-oxoglutarate [Compound (45b)]

In 4 ml of acetone were suspended, in nitrogen streams, 0.242 g of (3R,4R)-4-mercapto-3-phenoxyacetamido-2-azetindinone and 0.335 g of Compound (44) obtained in Reference Example 44. To the suspension was added 0.5 ml of hexamethylphosphoramide, followed by stirring at room temperature for one hour. To the reaciton mixture was added 30 ml of ethyl acetate. The mixture was washed with water and dried (MgSO$_4$). The solvent was distilled off under reduced pressure, and the residue was subjected to a silica gel column chromatography, eluting with ethyl acetate-hexane (3:2). Fractions containing the end product were combined and concentrated under reduced pressure to give 0.556 g of a mixture of the subject Compound (45a) and Compound (45b) as powders.

IR $\nu_{max}^{KBr}$ cm$^{-1}$: 3400, 1775, 1758, 1730, 1693, 1525, 1350.

REFERENCE EXAMPLE 46

Production of 1-(4-nitrobenzyl) 3-[(3R,4R)-3-phenoxyacetamido-2-azetidinon-4-yl]thiomethyl-2-oxoglutarate [Compound (46)]

In 0.1 ml of anisole was dissolved 0.215 g of the mixture of Compound (45a) and Compound (45b) obtained in Reference Example 45. To the solution was added, under ice-cooling, 4 ml of trifluoroacetic acid, and the mixture was stirred at the same temperature for 2 hours. The solvent was distilled off under reduced pressure. To the residue were added 5 ml of dichloromethane and 5 ml of hexane. The mixture was subjected to concentration under reduced pressure twice. The resulting residue was washed with 5 ml of hexane. The solvent was distilled off to leave the subject Compound (46) in a crude state, which was used in the following Example 9 as it was.

REFERENCE EXAMPLE 47

Production of 4-nitro)benzyl (6R,7R)-3-t-butyloxycarbonylmethyl-2-hydroxy-8-oxo-7-phenylacetamido-5-thia-1-azabicyclo[4,2,0]octane-2-carboxylate [Compound (47a) and 1-(4-nitrobenzyl)-5-(t-butyl) 3-[(3R,4R)-3-phenylacetamido-2-azetidinon-4-yl]thiomethyl-2-oxoglutarate [Compound (47b)]

In 50 ml of acetone were suspended 4.02 g of (3R,4R)-mercapto-3-phenylacetamido-2-azetidinone and 5.49 g of Compound (44) obtained in Reference 44. To this suspension was added 10 ml of hexamethylphosphoramide, and the mixture was stirred at room temperature for one hour. To the reaction mixture was added 200 ml of ethyl acetate, which was washed with water and dried ($MgSO_4$). The solvent was distilled off under reduced pressure, and the residue was subjected to a silica gel column chromatography, eluting with ethyl acetate-hexane (3:2). Fractions containing the end product were combined and concentrated under reduced pressure to give 9.40 g of a mixture of the subject Compound (47a) and Compound (47b) as powders.

IR $\nu_{max}^{KBr}$ cm$^{-1}$: 3400, 1785m 1774, 1760, 1635, 1526, 1350.

REFERENCE EXAMPLE 48

Production of 1-(4-nitrobenzyl) 3-[(3R,4R)-3-phenylacetamido-2-azetidinon-4-yl]thiomethyl-2-oxoglutarate [Compound (48)]

In 5 ml of anisole was dissolved 9.40 g of the mixture of Compound (47a) and Compound (47b) obtained in Reference Example 47. To this solution was added, under ice-cooling, 100 ml of trifluoroacetic acid, and the mixture was stirred at the same temperature for 2 hours. The solvent was distilled off under reduced pressure. To the residue were added 50 ml of dichloromethane and 50 ml of hexane. The mixture was subjected to distillation under reduced pressure twice. The residue was washed with 50 ml of hexane, and the solvent was distilled off under reduced pressure to give the subject Compound (48) in a crude state, which was used, without purification, in the following Example 12.

REFERENCE EXAMPLE 49

Production of 4-nitrobenzyl (6R,7R)-3-t-butyloxycarbonylmethyl-2-hydroxy-8-oxo-7-phenylacetamido-5-thia-1-azabicyclo [4,2,0]octane-2-carboxylate [Compound (47a)]

In 60 ml of dichloromethane was dissolved 4.70 g of the mixture of Compound (47a) and Compound (47b) as obtained in Reference Example 47. To the solution was added 50 g of silica gel, which was stirred at room temperature for 3 hours. To the reaction mixture was added 400 ml of ethyl acetate, then insolubles were filtered off. The filtrate was concentrated under reduced pressure to give 4.70 g of the subject Compound (47a). This product was employed for the subsequent Reference Example 50 without subjecting to purification.

REFERENCE EXAMPLE 50

Production of 4-nitrobenzyl (6R,7R)-3-carboxylmethyl-2-hydroxy-8-oxo-7-phenylacetamido-5-thia-1-azabicyclo[4,2,0] octane-2-carboxylate [Compound (50)]

In 2.5 ml of anisole was dissolved 4.70 g of Compound (47a) as obtained in Reference Example 49. To the solution was added 50 ml of trifluoroacetic acid under ice-cooling, and the mixture was stirred for 2 hours at the same temperature. To the reaction mixture was added 50 ml of dichloromethane. The solvent was distilled off under reduced pressure. To the residue were added 25 ml of dichloromethane and 25 ml of hexane, then the mixture was subjected to concentration under reduced pressure. This procedure was conducted twice. The residue was washed with 25 ml of hexane to give a crude product of the subject Compound (50), which was employed without purification for Example 23 to be given hereafter.

REFERENCE EXAMPLE 51

Production of (3S,4R)-1-t-butyldimethylsilyl-3-methoxy-3-phenylacetamido-4-triphenylmethylthio-2-azetidinone [Compound (51)]

In 8 ml of anhydrous tetrahydrofuran was dissolved 0.1 g of (3R,4R)-1-t-butyldimethylsilyl-3-phenylacetamido-4-triphenylmethylthio-2-azetidinone. To the solution were added in nitrogen streams at −78° C. 0.67 ml of a methanol solution containing 0.50 mM of lithium methoxide and 0.027 g of t-butyl hypochlorite. The temperature of the mixture was raised to −25° C. taking 15 minutes. The reaction mixture was cooled to −78° C., to which was added 0.034 g of acetic acid, followed by distilling off the solvent under reduced pressure. The residue was dissolved in 10 ml of ethyl acetate, and the solution was washed with a 10%(w/w) aqueous solution of sodium thiosulfate, followed by drying ($MgSO_4$). The solvent was distilled off under reduced pressure. The residue thus obtained was allowed to pass through a column of silica gel, followed by elution with ethyl acetate-hexane (1:3). Fractions containing the object compound were collected and concentrated under reduced pressure to give 0.079 g of the subject Compound (51) as an oil IR $\nu_{max}^{neat}$ cm$^{-1}$: 3390, 1765, 1688, 1491, 1245.

NMR (90 MHz, CDCl₃) δ: 0.33 (3H, s), 0.38 (3H, s), 0.96 (9H, s), 3.23 (3H, s), 3.32 (2H, s), 4.46 (1H, s), 4.59 (1H, s), 7.10–7.50 (20H, m).

REFERENCE EXAMPLE 52

Production of 1-(4-nitrobenzyl)-5-(t-butyl) 3-[(3s,4R)-1-t-butyldimethylsilyl-3-methoxy-3-phenylacetamido-2-oxoazetidine-4-yl]thiomethyl-2-oxoglutarate [Compound (52)]

In 40 ml of anhydrous methanol was dissolved 1.11 g of Compound (51) as obtained in Reference Example 51. To the solution was added dropwise at −15 to −13° C. 15 ml of an anhydrous methanol solution containing 0.739 g of mercuric acetate. The mixture was stirred at the same temperature for 15 minutes. The reaction mixture was cooled to −78° C., to which was introduced hydrogen sulfide gas for 5 minutes, followed by introduction of nitrogen gas for 10 minutes. The solvent was distilled off under reduced pressure. To the residue was added 50 ml of dichloromethane, and insolubles were filtered off. The filtrate was concentrated under reduced pressure to a volume of about 10 ml, to which was added 0.978 g of Compound (44) as obtained in REference Example 44, followed by stirring at room temperature for 1 hour in nitrogen streams. The solvent was evaporated off under reduced pressure, and the residue thus obtained was allowed to pass through a column of silica gel, followed by elution with ethyl acetate-hexane (1:2→1:1). Fractions containing the object compound were combined and concentrated under reduced pressure to give 0.984 g of the subject Compound (52) as an oily product.

IR $\nu_{max}^{neat}$ cm⁻¹: 3310, 1760, 1735, 1690, 1525, 1346, 1250.

REFERENCE EXAMPLE 53

Production of 4-nitrobenzyl (6R,7S)-3-t-butyloxycarbonylmethyl-2-hydroxy-7-methoxy-7-phenylacetamido-8-oxo-5-thia-1-azabicyclo[4,2,0]octane-2-carboxylate [Compound (53)]

In 3 ml of acetonitrile was dissolved 0.143 g of Compound 52 as obtained in Reference Example 52. To the solution were added under ice-cooling 0.3 ml of methanol, 0.047 g of acetic acid and 0.034 g of potassium fluoride. The mixture was stirred at the same temperataure for 10 minutes. To the reaction mixture was added 10 ml of ethyl acetate, which was washed with a saturated aqueous saline solution, followed by drying (MgSO₄). The solvent was distilled off under reduced pressure, and the residue was allowed to pass through a column of silica gel, followed by eluting with ethyl acetate-hexane (1:1). Fractions containing the object compound were combined and concentrated under reduced pressure to give 0.097 g of the subject Compound (53) as an oily product.

IR $\nu_{max}^{neat}$ cm⁻¹: 3305, 1760, 1726, 1672, 1520, 1347.

REFERENCE EXAMPLE 54

Production of 4-nitrobenzyl (6R,7S)-3-carboxymethyl-2-hydroxy-7-methoxy-7-phenylacetamido-8-oxo-5-thia-1-azabicyclo [4,2,0]octane-2-carboxylate [Compound (54)]

In 0.2 ml of anisole was dissolved 0.105 g of Compound (53) as obtained in Reference Example 53. To the solution was added under ice-cooling 2 ml of trifluoroacetic acid, and the mixture was stirred at the same temperature for 3 hours. To the reaction mixture was added 3 ml of dichloromethane, then the solvent was distilled off under reduced pressure. To the residue thus obtained were added 2 ml of dichloromethane and 2 ml of hexane then the mixture was concentrated under reduced pressure. This procedure was repeated twice. The residue thus obtained was washed with 3 ml of hexane to give a crude product of the subject Compound (54), which was employed, withou purification, for Example 41 to be given hereafter.

REFERENCE EXAMPLE 55

Production of dimethyl 2-bromo-4,4-dimethylglutarate [Compound (55)]

To 45 g of thionyl chloride was added 32.6 g of 2,2-dimethyl glutaric acid, and the mixture was stirred at 70° C. for 4 hours. To the reaction mixture were added 40 ml of phosphorus tribromide and 21 ml of bromine, and the mixture was stirred at 90° C. for 14 hours. To the resulting mixture was added dropwise an excess amount of absolute methanol, which was stirred at room temperature overnight. Methanol was distilled off under reduced pressure, and the residue was dissolved in 200 ml of ethyl acetate, followed by washing with water and drying (MgSO₄). The solvent was distilled off under reduced pressure, and the residue was allowed to pass through a column of silica gel. Elution was conducted with ethyl acetate-hexane (1:4). Fractions containing the object compound were combined and concentrated under reduced pressure to give 49.3 g of the subject Compound (55) as an oily product.

IR $\nu_{max}^{neat}$ cm⁻¹: 1750, 1740, 1200

NMR (90 MHz, CDCl₃) δ: 1.20 (6H, d, J=8 Hz), 2.26 (1H, dd, J=6, 18 Hz), 2.56 (1H, dd, J=11, 18 Hz), 3.70 (6H, s), 4.30 (1H, dd, J=6, 11 Hz).

REFERENCE EXAMPLE 56

Production of dimethyl 4,4-dimethyl-2-hydroxyglutarate [Compound (56a)] and 3,3-dimethyl-5-methoxycarbonyltetrahydro-2-furanone [Compound (56b)]

To 150 ml of a 3.7N sodium hydroxide solution was added 36.6 g of Compound (55) as obtained in Reference Example 55, and the mixture was stirred at room temperature overnight, followed by further stirring at 70° C. for 150 minutes. To the reaction mixture was added 100 ml of benzene, followed by concentration under reduced pressure. This procedure was conducted three times to give white solids. To the solids were added 100 ml of N,N-dimethylformamide, 100 ml of methyl iodide and 10 g of n-tetrabutylammonium bromide. The resulting suspension was stirred at room temperature for 2 days and insoluble materials were filtered off. To the filtrate was added 200 ml of ethyl acetate, followed by washing with water three times and drying (MgSO₄). The solvent was distilled off under reduced pressure to give 17.1 g of a mixture of the subject Compound (56a) and the subject Compound (56b). The product thus obtained was employed, without purification, for the subsequent Reference Example 57.

REFERENCE EXAMPLE 57

Production of dimethyl 4,4-dimethyl-2-oxoglutarate [Compound (57)]

In 10 ml of anhydrous methylene chloride was dissolved 1.1 ml of oxalyl chloride. To the solution was added dropwise 1 ml of anhydrous dimethyl sulfoxide at −70° C. The mixture was stirred at −70° C. for 10 minutes, to which was then added dropwise 1.1 g of the mixture of Compound (56a) and Compound (56b) as obtained in Reference Example 56. The mixture was stirred at −70° C. for 20 minutes, followed by addition of 3.7 ml of triethyamine dropwise, which was stirred at −65° C. for 15 minutes. To the reaction mixture was added 30 ml of dichloromethane, and the solution was washed with water and a saturated aqueous saline solution and dried (MgSO$_4$). The solvent was distilled off under reduced pressure. The residue thus obtained was allowed to pass through a column of silica gel, followed by elution with ethyl acetate-hexane (1:4). Fractions containing the object compound were combined and concentrated under reduced pressure to give 418 mg of the subject Compound (57) as an oil.

IR $\nu_{max}^{neat}$ cm$^{-1}$: 1750, 1730.

NMR(90 MHz, CDCl$_3$) δ: 1.27(3H, s), 3.08(2H, s), 3.65(3H, s), 3.85(3H, s).

REFERENCE EXAMPLE 58

Production of 1-(4-nitrobenzyl) 4,4-dimethyl-2-oxoglutarate [Compound (58)]

To 70 ml of a 0.6N sodium hydroxide solution was added 4.1 g of Compound (57) as obtained in Reference Example 57, and the mixture was stirred at room temperature for 1 day. To the reaction mixture was added an excess amount of Dowex 50-H type ion-exchange resin, which was stirred at room temperature for 3 hours. The resin was filtered off and the filtrate was lyophilized to give white solids, which was dissolved in 60 ml of N,N-dimethylformamide. To the solution was added 2 ml of dicyclohexylamine, and the mixture was stirred at 50° C. for 20 minutes. To the reaction mixture was added 2.16 g of 4-nitrobenzyl bromide, and the mixture was stirred at 70° C. for 70 minutes. The resulting mixture was cooled, to which was added 10 ml of ethyl acetate. Precipitating crystals were filtered off, and the filtrate was washed with water three times and dried (MgSO$_4$). The solvent was distilled off under reduced pressure, and the residue was allowed to pass through a column of silica gel, followed by elution with ethyl acetate-hexane (1:2). Fractions containing the object compound were combined and concentrated under reduced pressure to give 2.04 g of the subject Compound (58) as an oily product.

IR $\nu_{max}^{neat}$ cm$^{-1}$: 1785, 1770, 1750.

NMR(90 MHz, CDCl$_3$) δ: 1.36(6H, s), 2.47(2H, bs), 5.37(2H, s), 7.50(2H, d, J=9 Hz), 8.23(2H, d, J=9 Hz).

REFERENCE EXAMPLE 59

Production of 1-(4-nitrobenzyl) 3-bromo-4,4-dimethyl-2-oxoglutarate [Compound (59)]

In 5 ml of acetic acid was dissolved 910 mg of Compound (58) as obtained in Reference Example 58. To the solution were added 166 μl of bromine and several drops of a 30% hydrogen bromide acetic acid solution and the mixture was stirred at 50° C. for 50 minutes. To the reaction mixture was added 30 ml of ethyl acetate, which was washed with water 5 times and dried (MgSO$_4$). The solvent was distilled off under reduced pressure, and the residue was allowed to pass through a column of silica gel, followed by elution with ethyl acetate-hexane (1:2). Fractions containing the object compound were combined and concentrated under reduced pressure to give 664 mg of the subject Compound (59) as an oil.

IR $\nu_{max}^{CHCl_3}$ cm$^{-1}$: 1790, 1760, 1750.

NMR(90 MHz, CDCl$_3$) δ: 1.34(3H, s), 1.47(3H, s), 4.65(1H, s), 5.44(2H, s), 7.54(2H, d, J=9 Hz), 8.25 (2H, d, J=9 Hz).

REFERENCE EXAMPLE 60

Production of dimethyl 2-t-butyldimethylsilyloxy-4,4-dimethyl-2-pentenedioate [Compound (60)]

In 5 ml of dichloromethane was dissolved 298 mg of Compound (57) as obtained in Reference Example 57. To the solution were added at −78° C. in nitrogen streams 0.29 ml of triethylamine and 0.4 ml of t-butyldimethylsilyl trifluoromethanesulfonate. The mixture was gradually warmed to room temperature. To the reaction mixture was added 30 ml of dichloromethane, then the mixture was washed with water and dried (MgSO$_4$). The solvent was distilled off under reduced pressure, and the residue thus obtained was allowed to pass through a column of silica gel, followed by elution with ethyl acetate-hexane (1:6). Fractions containing the object compound were combined and concentrated under reduced pressure to give 148 mg of the subject Compound (60) as an oily product.

NMR(90 MHz, CDCl$_3$) δ: 0.15(6H, s), 0.90(9H, s), 1.40(6H, s), 3.67(3H, s), 3.74(3H, s), 5.95(1H, s).

REFERENCE EXAMPLE 61

Production of dimethyl 4,4-dimethyl-3-methylthio-2-oxoglutarate [Compound (61)]

To 3 ml of dichloromethane were added 60 mg of Compound (60) as obtained in Reference Example 60, 29 mg of methyl methanethiosulfonate and 10 pieces of Molecular Sieves (3A). To the mixture was added 60 mg of tetra-n-butylammonium fluoride at −78° C., and the mixture was stirred at room temperature for 1 day. To the resulting mixture were further added 20 mg of methyl methanethiosulfonate and 40 mg of tetra-t-butylammonium fluoride, and the mixture was stirred at room temperature for 1 day. Insolubles were filtered off, and the filtrate was concentrated under reduced pressure. The residue thus obtained was allowed to pass through a column of silica gel, followed by elution with ethyl acetate-hexane (1:4). Fractions containing the object compound were then combined and concentrated under reduced pressure to give 29 mg of the subject Compound (61) as an oily product.

IR $\nu_{max}^{CHCl_3}$ cm$^{-1}$: 1740, 1730.

NMR(90 MHz, CDCl$_3$) δ: 1.38(3H, s), 1.41(3H, s), 2.26(3H, s), 3.67(3H, s), 3.91(3H, s), 4.25(1H, s).

REFERENCE EXAMPLE 62

Production of dimethyl 4,4-dimethyl-2-oxo-3-phenylthioglutarate [Compound (62)]

In 2 ml of dichloromethane was dissolved 59 mg of Compound (60) as obtained in Reference Example 60. To the solution was added a solution of 36 mg of phenylsulfenylchloride in 1.5 ml of dichloromethane at −70° C., and the mixture was stirred at room temperature for 3 days. To the reaction mixture was added 15 ml of dichloromethane, which was washed with water and dried (MgSO$_4$). The solvent was distilled off under reduced pressure, and the residue thus obtained was allowed to pass through a column of silica gel, followed by elution with ethyl acetate-hexane (1:6). Fractions containing the object compound were combined and concentrated under reduced pressure to give 7 mg of the subject Compound (62) as an oily product.

IR $\nu_{max}^{CHCl_3}$ cm$^{-1}$: 1800, 1740, 1730, 1720.

NMR(90 MHz, CDCl$_3$) δ: 1.43(3H, s), 1.47(3H, s), 3.63(3H, s), 3.73(3H, s), 4.82(2H, s), 7.2–7.8(5H, m).

REFERENCE EXAMPLE 63

Production of 1-(4-nitrobenzyl)-5-(t-butyl) 2-t-butyldimethylsilyloxy-2-pentenedioate [Compound (63)]

In 2 ml of anhydrous dichloromethane was dissolved 0.1 g of Compound (42) as obtained in Reference Example 42. To the solution were added 0.094 g of t-butyldimethylsilyl trifluoromethanesulfonate and 0.042 g of triethylamine at −78° C. in nitrogen streams. The temperature of the mixture was raised to −30° C. while stirring. The reaction mixture was washed with a 1% aqueous solution of sodium hydrogen-carbonate and with a saturated aqueous saline solution, followed by drying (MgSO$_4$). The solvent was distilled off under reduced pressure, and the residue thus obtained was allowed to pass through a column of silica gel, followed by elution with ethyl acetate-hexane (1:7). Fractions containing the object compound were combined and concentrated under reduced pressure to give 0.134 g of the subject Compound (63) as an oily product.

IR $\nu_{max}^{neat}$ cm$^{-1}$: 1727, 1522, 1346, 1250, 1146, 1132.

NMR(90 MHz, CDCl$_3$) δ: 0.16(6H, s), 0.95(9H, s), 1.45(9H, s), 3.15(2H, d, J=7 Hz), 5.27(2H, s), 6.24(1H, t, J=7 Hz), 7.52 (2H, d, J=9 Hz), 8.22(2H, d, J=9 Hz).

REFERENCE EXAMPLE 64

Production of 1-(4-nitrobenzyl)-5-(t-butyl) 3-methylthio-2-oxoglutarate [Compound (64)]

In 2 ml of anhydrous dichloromethane was dissolved 0.115 g of Compound (63) as obtained in Reference Example 63. To the solution was added 0.2 g of Molecular Sieves in nitrogen streams. To the mixture was then added at −78° C. 1 ml of an anhydrous dichloromethane solution containing 0.039 g of methyl methanethiosulfonate and 0.074 g of tetra-n-butylammonium fluoride. The temperature of the mixture was raised to 0° C. taking 30 minutes while stirring, then insolubles were filtered off. The filtrate was concentrated under reduced pressure, and the residue thus obtained was allowed to pass through a column of silica gel, followed by elution with ethyl acetate-hexane (1:4). Fractions containing the object compound were combined and concentrated under reduced pressure to give 0.036 g of the subject Compound (64) as an oily product.

IR $\nu_{max}^{neat}$ cm$^{-1}$: 1720, 1525, 1348.

NMR(90 MHz, CDCl$_3$) δ: 1.41(9H, s), 1.90(3H, s), 2.63(1H, dd, J=6, 17 Hz), 3.01(1H, dd, J=9, 17 Hz), 4.41(1H, dd, J=6, 9 Hz), 5.21 (2H, s), 7.57(2H, d, J=9 Hz), 8.24(2H, d, J=9 Hz).

REFERENCE EXAMPLE 65

Production of 1-(4-nitrobenzyl)-5-(t-butyl) 3-phenylthio-2-oxoglutarate [Compound (65)]

In 3 ml of dichloromethane was dissolved 65 mg of Compound (63) as obtained in Reference Example 63. To the solution was added a solution of 21 mg of phenylsulfenylchloride in 2 ml of dichloromethane at −60° C., and the mixture was stirred at room temperature for 3 days. To the reaction mixture was added 15 ml of dichloromethane, and the mixture was washed with water, followed by drying (MgSO$_4$). The solvent was distilled off under reduced pressure, and the residue thus obtained was allowed to pass through a column of silica gel, followed by elution with ethyl acetate-hexane (1:5). Fractions containing the object compound were combined and concentrated under reduced pressure to give 31 mg of the subject Compound (65) as an oily product.

NMR(90 MHz, CDCl$_3$) δ: 0.93(9H, s), 2.72(1H, dd, J=11, 18 Hz), 3.03 (1H, dd, J=8, 18 Hz), 4.18(1H, dd, J=8, 11 Hz), 5.19(2H, s), 7.23 (5H, m), 7.42(2H, d, J=9 Hz), 8.13(2H, d, J=9 Hz).

REFERENCE EXAMPLE 66

Production of 1-(4-nitrobenzyl)-5-(t-butyl) 4,4-dimethyl-2-oxoglutarate [Compound (66)]

To 20 ml of dichloromethane were added 945 mg of Compound (58) as obtained in Reference Example 58 and 20 ml of dichloromethane. To the solution were added, under ice-cooling, 0.1 ml of sulfuric acid and 5 ml of isobutene. The mixture in a sealed vessel was left standing at room temperautre in a dark place for 5 days. The reaciton mixture was washed with water and dried (MgSO$_4$). The solvent was distilled off under reduced pressure, and the residue thus obtained was allowed to pass through a column of silica gel, followed by elution with ethyl acetate-hexane (1:2). Fractions containing the object compound were combined and concentrated under reduced pressure to give 385 mg of the subject Compound (66) as an oily product. Besides, 591 mg of Compound (58) was recovered.

IR $\nu_{max}^{neat}$ cm$^{-1}$: 1740, 1530, 1350.

NMR(90 MHz, CDCl$_3$) δ: 1.25(6H, s), 1.40(9H, s), 3.03(2H, s), 5.36(2H, s), 7.58(2H, d, J=9 Hz), 8.22(2H, d, J=9 Hz).

REFERENCE EXAMPLE 67

Production of 1-(4-nitrobenzyl)-5-(t-butyl) 4,4-dimethyl-3-methylene-2-oxoglutarate [Compound (67)]

A mixture of 400 mg of Compound (66) as obtained in Reference Example 66, 0.6 ml of N,N,N',N'-tetramethyldiaminomethane and 0.5 ml of acetic anhydride was stirred for 1 hour under ice-cooling then overnight at room temperature. To the reaction mixture was added 30 ml of ethyl acetate, which was washed with water twice, followed by drying (MgSO$_4$). The solvent was distilled off under reduced pressure. The residue thus obtained was allowed to pass through a column of silica gel, followed by elution with ethyl acetate-hexane (1:2). Fractions containing the object compound were combined and concentrated under reduced pressure to give 379 mg of the subject Compound (67) as pale yellow solids.

IR $\nu_{max}^{KBr}$ cm$^{-1}$: 1740, 1735, 1685.

NMR(90 MHz, CDCl$_3$) δ: 1.37(15H, s), 5.41(2H, s), 6.16(2H, d, J=13 Hz), 7.56(2H, d, J=9 Hz), 8.23(2H, d, J=9 Hz).

REFERENCE EXAMPLE 68

Production of 4-nitrobenzyl (6R,7R)-3-(2-t-butyloxycarbonylisopropyl)-2-hydroxy-8-oxo-7-phenylacetamido-5-thia-1-azabicyclo[4,2,0]octane-2-carboxylate [Compound (68a)] and 1-(4-nitrobenzyl)-5-(t-butyl) 4,4-dimethyl-3-[(3R,4R)-3-phenylacetamido-2-azetidinon-4-yl]thiomethyl-2-oxoglutarate [Compound (68b)]

In 5 ml of acetone were dissolved 350 mg of Compound (67) as obtained in Reference Example 67 and 220 mg of (3R,4R)-4-mercapto-3-phenylacetamido-2-azetidinone, and the solution was stirred for 10 minutes. To the solution was added 0.7 ml of hexamethylphosphoramide in nitrogen streams, and the mixture was stirred at room temperature for 4 days. Acetone was distilled off under reduced pressure. To the residue thus obtained was added 30 ml of ethyl acetate, which was washed with water twice, followed by drying (MgSO$_4$). The solvent was distilled off under reduced pressure, and the residue was allowed to pass through a column of silica gel, followed by elution with ethyl acetate-hexane (1:1). Fractions containing the object compound were combined and concentrated under reduced pressure to give 40 mg of the subject Compound (68a) and 67 mg of the subject Compound (68b) respectively as oily products.

Compound (68a)

IR $\nu_{max}^{CHCl_3}$ cm$^{-1}$: 1780, 1730, 1685.

NMR(90 MHz, CDCl$_3$) δ: 1.15(6H, bs), 1.40(9H, s), 2.62(1H, dd, J=2, 12 Hz), 2.6–2.9(1H, m), 3.18(1H, dd, J=10, 12 Hz), 3.60(2H, s), 5.12(1H, d, J=5 Hz), 5.33(2H, q), 5.43(1H, dd, J=5, 9 Hz), 6.23(1H, bd, J=9 Hz), 7.29(5H, d, J=2 Hz), 7.56(2H, d, J=9 Hz), 8.20(2H, d, J=9 Hz).

Compound (68b)

IR $\nu_{max}^{CHCl_3}$ cm$^{-1}$: 1770, 1750, 1680.

NMR(90 MHz, CDCl$_3$) δ: 1.16(6H, s), 1.35(9H, s), 2.5–2.7(2H, m), 3.60(2H, s), 3.95(1H, dd, J=5, 9 Hz), 4.90(1H, d, J=5 Hz), 5.36 (2H, q), 5.42(1H, dd, J=5, 9 Hz), 6.58(1H, bd, J=9 Hz), 6.77 (1H, bs), 7.27(5H, s), 7.57(2H, d, J=9 Hz), 8.18(2H, d, J=9 Hz).

REFERENCE EXAMPLE 69

Production of 1-(4-nitrobenzyl) 4,4-dimethyl-3-[(3R,4R)-3-phenylacetamido-2-azetidinon-4-yl]thiomethyl-2-oxoglutarate [Compound (69)]

To 10 ml of 1,2-dichloromethane were added 187 mg of Compound (68b) as obtained in Reference Example 68 and 2.3 g of silica gel (200 to 300 mesh). The mixture was stirred at 70° C. for 1 day. The silica gel was filtered off, and the filtrate was concentrated under reduced pressure. The residue was allowed to pass through a column of silica gel, followed by elution with ethyl acetate-hexane (3:2). Fractions containing the object compound were combined and concentrated under reduced pressure to give 70 mg of the subject Compound (69) as an oily product. Besides, 71 mg of Compound (68b) was recovered.

IR $\nu_{max}^{CHCl_3}$ cm$^{-1}$: 1780, 1760, 1525.

NMR(90 MHz, CDCl$_3$) δ: 1.16(3H, s), 1.23(3H, s), 2.3–3.0(3H, m), 3.58(2H, s), 4.82(1H, d, J=4 Hz), 5.28(2H, s), 5.36(1H, m), 5.78(1H, bd, J=8 Hz), 6.6–6.9(2H, m), 7.27(5H, s), 7.47(2H, d, J=8 Hz), 8.16(2H, d, J=8 Hz).

EXAMPLE 1

Production of (4-nitro)benzyl (9S,10S)-10-benzyloxycarbonylamino-4,11-dioxo-3-oxa-7-thia-1-azatricyclo[7,2,0,0$^{2,6}$] undecane-2-carboxylate In 5 ml of dichloromethane was dissolved the crude Compound (36) obtained in Reference Example 36. To this solution was added, under nitrogen streams, 0.145 g of dicyclohexylcarbodiimide, and the mixture was stirred at room temperature for one hour. To the residue was added 15 ml of ethyl acetate, and insoluble materials were filtered off. The filtrate was concentrated under reduced pressure, and the residue was subjected to a silica gel column chromatography, which was eluted with ethyl acetate-hexane (2:3). Fractions containing the end product were combined and concentrated under reduced pressure to give 95 mg of Isomer A and 63 mg of Isomer B of the subject compound, respectively in a powdery state.

Isomer A: (2R, 6R, 9S, 10S)-isomer

IR $\nu_{max}^{CHCl_3}$ cm$^{-1}$: 1850, 1780, 1725, 1344.

NMR(90 MHz, CDCl$_3$) δ: 2.45–3.10(4H, m), 4.10 (2H, m), 4.95(1H, dd, J=4 Hz, 7 Hz), 5.10(2H, s), 5.33(2H, ABq, J=13 Hz, 14 Hz), 5.66(1H, d, 7 Hz), 7.33(5H, s), 7.53(2H, d, J=9 Hz), 8.19(2H, d, J=9 Hz).

Isomer B: (2S, 6S, 9S, 10S)-isomer

IR $\nu_{max}^{CHCl_3}$ cm$^{-1}$: 1816, 1770, 1755, 1720, 1343.

NMR(90 MHz, CDCl$_3$) δ: 2.26–3.27(4H, m), 3.66 (1H, m), 4.10(1H, m), 4.90(1H, dd, J=5 Hz, 7 Hz), 5.08(2H, s), 5.36(2H, ABq, J=14 Hz, 15 Hz), 6.07(1H, d, J=7 Hz), 7.32(5H, s), 7.54(2H, d, J=9 Hz), 8.22(2H, d, J=9 Hz).

EXAMPLE 2

Production of ((4-nitor)benzyl (9S,10S)-4,11-dioxo-10-(4-nitrobenzyloxycarbonylamino)-3-oxa-7-thia-1-azatricyclo [7,2,0,0$^{2,6}$]undecane-2-carboxylate In a mixture of 20 ml of dichloromethane and 10 ml of tetrahydrofuran was dissolved the crude Compound (41) obtained in Reference Example 41. To this solution was added 2.33 g of dicyclohexylcarbodiimide under nitrogen streams, which was stirred at room temperature for one hour. The solvent was distilled off under reduced pressure. To the residue was added 50 ml of ethyl acetate, and insoluble materials were filtered off. The residue was subjected to a silica gel column chromatography. Elution was conducted with ethyl acetate-hexane (3:2). Fractions containing the end product were combined and concentrated under reduced pressure to give 0.941 g of Isomer A and 0.732 g of Isomer B of the subject compound, respectively in a powdery state.

Isomer A: (2R, 6R, 9S, 10S)-isomer

FD-MS m/z: 572 (M+).

IR $\nu_{max}^{KBr}$ cm$^{-1}$: 3375, 1805, 1780, 1730, 1520, 1349.

NMR(90 MHz, CDCl$_3$) δ: 2.30–3.12(4H, m), 4.15 (1H, d, J=6 Hz), 4.18(1H, m), 5.00(1H, dd, J=5 Hz, 7 Hz), 5.20(2H, s), 5.39(2H, ABq, J=12 Hz, 13 Hz), 5.75(1H, d, J=7 Hz), 7.47(2H, d, J=9 Hz), 7.54(2H, d, J=9 Hz), 8.18(4H, d, J=9 Hz).

Isomer B: (2S, 6S, 9S, 10S)-isomer

FD-MS m/z: 572 (M+).

IR $\nu_{max}^{KBr}$ cm$^{-1}$: 3350, 1812, 1772, 1724, 1520, 1345.

NMR(90 MHz, CDCl$_3$) δ: 2.30–3.30(4H, m), 3.70 (1H, t, J=10 Hz), 4.14(1H, m), 4.96(1H, dd, J=5 Hz, 8 Hz), 5.17(2H, s), 5.39(2H, ABq, J=13 Hz, 14 Hz), 6.41(1H, d, J=8 Hz), 7.48(2H, d, J=9 Hz), 7.50(2H, d, J=9 Hz), 8.13(2H, d, J=9 Hz), 8.19(2H, d, J=9 Hz).

EXAMPLE 3

Production of sodium (2R,6R,9S,10S)-4,11-dioxo-10-phenylacetamido-3-oxa-7-thia-1-azatricyclo[7,2,0,0$^{2,6}$] undecane-2-carboxylate In 4 ml of ethyl acetate was dissolved 0.15 g of the Isomer A obtained in Example 2. To the solution were added 4 ml of a 0.1 mol. phosphate buffer solution of pH 7.0 and 0.075 g of 10% palladium-carbon. Into the mixture was introduced, while stirring under ice-cooling, hydrogen gas. In 1.5 hour after starting of the reaction, 0.075 g of 10% palladium-carbon was added to the reaction system, followed by stirring for further one hour. The catalyst was filtered off, and the aqueous layer was separated, then the organic layer was subjected to extraction with 2 ml of water. The aqueous layers were combined, to which were added, under ice-cooling, 4 ml of tetrahydrofuran, 0.032 g of sodium hydrogencarbonate and 0.0473 g of phenylacetyl chloride. The mixture was stirred at the same temperature for 30 minutes. Tetrahydrofuran contained in the reaction mixture was distilled off, followed by washing the residue with 3 ml of ethyl acetate. The aqueous solution thus obtained was subjected to a Amberlite XAD-2 column chromatography, eluting with water-ethanol (90:10). Fractions containing the end product were combined, from which ethanol was distilled off under reduced pressure, followed by freeze-drying to give 0.078 g of the subject compound as powders.

IR $\nu_{max}^{KBr}$ cm$^{-1}$: 3410, 3250, 1790, (sh), 1780(sh), 1766, 1662, 1659, 1362, 1195.

NMR(90 MHz, D$_2$O) δ: 2.10–3.10(4H, m), 3.78(2H, s), 3.78(1H, m), 4.16(1H, d, J=6 Hz), 5.25(1H, d, J=6 Hz), 7.48(5H, s).

EXAMPLE 4

Production of Sodium (2S,6S,9S,10S)-4,11-dioxo-10-phenylacetamido-3-oxa-7-thia-1-azatricyclo[7,2,0,0$^{2,6}$]undecane-carboxylate In 4 ml of ethyl acetate was dissolved 0.15 g of Isomer B obtained in Example 2. To this solution were added 4 ml of 0.1 mol. phosphate buffer solution of pH 7.0 and 0.075 g of 10% palladium-carbon. Into the mixture was introduced hydrogen gas while stirring under ice-stirring. In 1.5 hour after starting of the reaction, 0.075 g of 10% palladium-carbon was added to the reaction system, followed by stirring for further one hour. The catalyst was filtered off, and the aqueous layer was separated. The organic layer was subjected to extraction with 2 ml of water. Aqueous layers were combined, to which were added under ice-cooling 4 ml of tetrahydrofuran, 0.032 g of sodium hydrogencarbonate and 0.0473 g of phenylacetic acid. The mixture was stirred for 30 minutes at the same temperature. Tetrahydrofuran contained in the reaction mixture was distilled off under reduced pressure, and the residue was washed with 3 ml of ethyl acetate. Thus-obtained aqueous solution was subjected to a Amberlite XAD-2 column chromatography eluting with water-ethanol (90:10). Fractions containing the end product were combined, from which ethanol was distilled off under reduced pressure. The residue was freeze-dried to give 0.057 g of the subject compound as powders.

IR$\nu_{max}^{KBr}$ cm$^{-1}$: 3450, 3270, 1793, 1752 (sh), 1743, 1663, 1653, 1640, 1364.

NMR (90 MHz, D$_2$O)δ: 2.37–3.20 (4H, m), 3.76 (2H, s), 3.89 (1H, t, J=10 Hz), 4.32 (1H, m), 4.99 (1H, d, J=5 Hz), 7.47 (5H, s).

EXAMPLE 5

Production of sodium (2R, 6R, 9S, 10S)-10-[2-(2-aminothiazol-4-yl)-(Z)-2-methoxyiminoacetamido]-4,11-dioxo-3-oxa-7-thia-1-azatricyclo[7,2,0,0$^{2,6}$]undecane-2-carboxylate In 5 ml of ethyl acetate was dissolved 0.20 g of Isomer A obtained in Example 2. To this solution were added 5 ml of a 0.1 mol. phosphate buffer solution and 0.1 g of 10% palladium-carbon. Into the mixture was introduced hydrogen gas while stirring under ice-cooling. In one hour after starting of the reaction, 0.1 g of 10% palladium-carbon was added to the reaction system, followed by stirring for further two hours. The catalyst was filtered off, then the aqueous layer was separated, followed by extraction of the organic layer with 1 ml of water. The aqueous layers were combined, to which were added under ice-cooling 4 ml of tetrahydrofuran, 0.086 g of sodium hydrogencarbonate and 0.136 g of hydrochloride of 2-(2-chloroacetamidothiazol-4-yl)-(Z)-2-methoxyiminoacetyl chloride. The mixture was stirred for two hours at the same temperature. Tetrahydrofuran contained in the reaction mixture was distilled off under reduced perssure. To the residue was added 0.088 g of sodium N-methyldithiocarbamate, and the mixture was stirred at room temperature for two hours. The reaction mixture was washed with 5 ml of ethyl acetate, and subjected to a Amberlite XAD-2 column chromatography. Fractions eluted with water-ethanol (95:5) were combined, from which ethanol was distilled off, followed by freeze-drying the residue to give 0.116 g of the subject compound as powders.

IR$\nu_{max}^{KBr}$ cm$^{-1}$: 3430, 1787, 1775, 1768, 1670, 1554, 1385, 1368.

NMR (90 MHz, D$_2$O)δ: 2.43–3.45 (4H, m), 4.10 (3H, s), 4.23 (1H, d, J=7 Hz), 4.41 (1H, m), 5.45 (1H, d, J=6 Hz), 7.09 (1H, s).

EXAMPLE 6

Production of sodium (2S, 6S, 9S, 10S)-10-[2-(2-aminothiazol-4-yl)-(Z)-2-methoxyiminoacetamido]-4,11-dioxo-3-oxa-7-thia-1-azatricyclo[7,2,0,0$^{2,6}$]undecane-2-carboxylate In 5 ml of ethyl acetate was dissolved 0.20 g of Isomer B obtained in Example 2. To this solution were added 5 ml of a 0.1M phosphate buffer solution of pH 7 and 0.1 g of 10% palladium-carbon. Into the mixture was introduced hydrogen gas while stirring under ice-cooling. One hour after starting of the reaction, 0.1 g of 10% palladium-carbon was added to the reaction system, followed by stirring for further two hours. The catalyst was filtered off, then the aqueous layer was separated, followed by extraction of the organic layer with 1 ml of water. The aqueous layers were combined, to which were added under ice-cooling 4 ml of tetrahydrofuran, 0.086 g of sodium hydrogencarbonate and 0.136 g of hydrochloride of 2-(2-chloroacetamidothiazol-4-yl)-(Z)-methoxyiminoacetyl chloride. The mixture was stirred for two hours at the same temperature. Tetrahydrofuran contained in the reaction mixture was distilled off under reduced pressure. To the residue was added 0.088 g of sodium N-methyldithiocarbamate, and the mixture was stirred at room temperature for two hours. The reaction mixture was washed with 5 ml of ethyl acetate, and was subjected to Amberlite XAD-2 column chromatography. Fractions eluted with water-ethanol (95:5) were combined, from which ethanol was distilled off, followed by freeze-drying the residue to give 0.108 g of the subject compound as powders.

IR$\nu_{max}^{KBr}$ cm$^{-1}$: 3420, 1795, 1754, 1652, 1525, 1365.

NMR (90 MHz, D$_2$O)δ: 2.55–3.10 (4H, m), 3.94 (1H, m), 4.07 (3H, s), 4.47 (1H, m), 5.18 (1H, d, J=5 Hz), 7.05 (1H, s).

EXAMPLE 7

Production of sodium (2R, 6R, 9S, 10S)-10-[2-(2-aminothiazol-4-yl)-(Z)-2-[1-(4-nitrobenzyloxycarbonyl)-1-methylethoxyimino]acetamido]-4,11-dioxo-3-oxa-7-thia-1-azatricyclo[7,2,0,0$^{2,6}$]undecane-2-carboxylate In 6 ml of ethyl acetate was dissolved 0.2 g of Isomer A obtained in Example 2. To this solution were added 6 ml of a 0.1M phosphate buffer solution of pH 7.0 and 0.1 g of 10% palladium-carbon, to which was introduced hydrogen gas while stirring under ice-cooling. In one hour and two hours after starting of the reaction, 0.1 g each of palladium-carbon was added to the reaction system. The catalyst was filtered off, and the aqueous layer was separated, followed by extraction of the organic layer with 1 ml of water. The aqueous layers were combined to which were added under ice-cooling 5 ml of tetrahydrofuran, 0.088 g of sodium hydrogencarbonate and 0.21 g of hydrochloride of 2-(2-chloroacetamidothiazol-4-yl)-(Z)-2-[1-(4-nitrobenzyloxycarbonyl)-1-methylethoxyimino]acetyl chloride. The mixture was stirred at room temperature for 30 minutes. to the reaction mixture was added 0.09 of sodium N-methyldithiocarbamate, and the mixture was stirred for one hour at room temperature. The reaction mixture was concentrated under reduced pressure to a volume of about 8 ml. The residue was subjected to a Amberlite XAD-2 column chromatography. Fractions eluted with water-ethanol (75:25) were combined, from which ethanol was distilled off under reduced pressure, followed by freeze-drying to give 0.178 g of the subject compound as powder.

IR$\nu_{max}^{KBr}$ cm$^{-1}$: 3420, 1765, 1655, 1522, 1348.

NMR (90 MHz, D$_2$O)δ: 1.68 (6H, s), 2.38–3.40 (4H, m), 4.10–4.50 (2H, m), 5.37 (1H, d, J=5 Hz), 5.43 (2H, ABq, J=12 Hz, 17 Hz), 6.97 (1H, s), 7.83 (2H, d, J=9 Hz), 8.15 (2H, d, J=9 Hz).

EXAMPLE 8

Production of Sodium (2R, 6R, 9S, 10S)-10-[2-(2-aminothiazol-4-yl)-(Z)-2-(1-carboxy-1-methylethoxyimino)acetamido]-4,11-dioxo-3-oxa-7-thia-1-azatricyclo[7,2,0,0$^{2,6}$]undecane-2-carboxylate In 5 ml of water was dissolved 0.148 g of the compound obtained in Example 7. To this solution were added 5 ml of a 0.1M phosphate buffer solution, 5 ml of ethanol and 0.075 g of 10% palladium-carbon. Into the mixture was introduced hydrogen gas while stirring under ice-cooling. In 1.5 hour after starting of the reaction, 0.04 g of 10% palladium-carbon was added to the reaction system, followed by stirring for further one hour. The catalyst was filtered off, and the filtrate was concentrated under reduced pressure to a volume of about 5 ml. The residue was subjected to a Amberlite XAD-2 column chromatography. Fractions eluted with water were combined and freeze-dried to give 0.091 g of the subject compound as powders.

IR$\nu_{max}^{KBr}$ cm$^{-1}$: 3410, 1762, 1652, 1580, 1362.

NMR (90 MHz, D$_2$O)δ: 1.56 (3H, s), 1.59 (3H, s), 2.45–3.10 (4H, m), 4.26 (1H, d, J=7 Hz), 4.40 (1H, m) 5.43 (1H, d, J=5 Hz), 7.08 (1H, s).

EXAMPLE 9

Production of (4-nitro)benzyl (9R, 10R)-4,11-dioxo-10-phenoxyacetamido-3-oxa-8-thia-1-azatricyclo[7,2,0,0$^{2,6}$]undecane-2-carboxylate In 5 ml of dichloromethane was dissolved Compound (46) obtained in Reference Example 46 in a crude state. To this solution was added 0.205 g of hydrochloride of 1-ethyl-3-(3-dimethylaminopropyl)carbodiimide under ice-cooling in nitrogen streams. The mixture was stirred for one hour at room temperature. The solvent was distilled off under reduced pressure, and the residue was subjected to a silica gel column chromatography, followed by elution with ethyl acetate-hexane (4:3→3:2). Fractions containing the end product were combined and concentrated under reduced pressure to give 0.096 g of Isomer A of the subject compound as crystals. Besides, 0.090 g of Isomer B of the subject compound was obtained as powders.

Isomer A: (2R, 6R, 9R, 10R)-isomer

Melting point: 206°–207° C.

IR$\nu_{max}^{KBr}$ cm$^{-1}$: 3412, 1800, 1793, 1755, 1690, 1520, 1350.

NMR (90 MHz, DMSO-d$_6$) δ: 2.60–3.20 (5H, m), 4.60 (2H, s), 5.05 (1H, d, J=4 Hz), 5.32 (1H, dd, J=4 Hz, 9 Hz), 5.43 (2H, s), 7.00 (3H, m), 7.30 (2H, m), 7.68 (2H, d, J=9 Hz), 8.23 (2H, d, J=9 Hz), 8.73 (1H, d, J=9 Hz).

Isomer B: (2S, 6S, 9R, 10R)-isomer

IR$\nu_{max}^{KBr}$ cm$^{-1}$: 3360, 1813, 1782, 1750, 1690, 1520, 1350.

NMR (90 MHz, CDCl$_3$)δ: 2.40–3.40 (5H, m), 4.53 (2H, s), 5.08 (1H, d, J=4 Hz), 5.43 (2H, s), 5.55 (1H, dd, J=4 Hz, 9 Hz), 6.78–7.75 (8H, m), 8.22 (2H, d, J=9 Hz).

EXAMPLE 10

Production of Sodium (2R, 6R, 9R, 10R)-4,11-dioxo-10-phenoxyacetamido-3-oxa-8-thia-1-azatricyclo[7,2,0,0$^{2,6}$]undecane-2-carboxylate In 6 ml of ethyl acetate was dissolved 0.2 g of Isomer A obtained in Example 9, to which were added 6 ml of a 0.1M phosphate buffer solution of pH 7.0 and 0.1 g of 10% palladium-carbon, followed by stirring the mixture at 8° to 10° C. for one hour while introducing hydrogen gas. To the reaction mixture was added 0.1 g of 10% palladium-carbon, and the mixture was stirred for further two hours. The catalyst was filtered off, and the aqueous layer was separated, followed by extracting the organic layer with 1 ml of water. The aqueous layers were combined and subjected to a Amberlite XAD-2 column chromatography. Fractions eluted with water-ethanol (85:15) were combined, from which ethanol was distilled off under reduced pressure, followed by freeze-drying the residue to give 0.135 g of the subject compound as powders.

IR$\nu_{max}^{KBr}$ cm$^{-1}$: 3450, 1788, 1775, 1550.

NMR (90 MHz, D$_2$O)δ: 2.76–3.35 (5H, m), 4.83 (2H, s), 5.28 (1H, d, J=4 Hz), 5.56 (1H, d, J=4 Hz), 7.08–7.65 (5H, m).

EXAMPLE 11

Production of sodium (2S, 6S, 9R, 10R)-4,11-dioxo-10-phenoxyacetamido-3-oxa-8-thia-1-azatricyclo[7,2,0,0$^{2,6}$]undecane-2-carboxylate In 6 ml of ethyl acetate was dissolved 0.2 g of Isomer B obtained in Example 9, to which were added 6 ml of a 0.1M phosphate buffer solution of pH 7.0 and 0.1 g of 10% palladium-carbon, followed by stirring the mixture for one hour at 8° to 10° C. while introducing hydrogen gas. To the reaction mixture was added 0.1 g of 10% palladium-carbon, and the mixture was stirred for further two hours. The catalyst was filtered off, and the aqueous layer was separated, followed by subjecting the organic layer to extraction with 1 ml of water. The aqueous layers were combined and subjected to a Amberlite XAD-2 column chromatography. Fractions eluted with water-ethanol (85-15) were combined, from which ethanol was distilled off under reduced pressure, followed by freeze-drying to give 0.131 g of the subject compound as powders.

IR$\nu_{max}^{KBr}$ cm$^{-1}$: 3450, 1800, 1790, 1772, 1750, 1653.

NMR (90 MHz, D$_2$O)δ: 2.67–3.60 (5H, m), 4.82 (2H, s), 5.35 (2H, s), 7.03–7.60 (5H, m).

EXAMPLE 12

Production of (4-nitro)benzyl (9R, 10R)-4,11-dioxo-10-phenylacetamido-3-oxa-8-thia-1-azatricyclo[7,2,0,0$^{2,6}$]undecane-2-carboxylate In 100 ml of dichloromethane was dissolved the crude Compound (48) obtained in Reference Example 48, to which was added 6.16 g of hydrochloride of 1-ethyl-3-(3-dimethylaminopropyl)carbodiimide under ice-cooling in nitrogen streams, and the mixture was stirred for one hour. The solvent was distilled off under reduced pressure, and the residue was subjected to a silica gel column chromatography, followed by elution with ethyl acetate-hexane (4:3→2:1). Fractions containing the end product were combined and concentrated under reduced pressure to obtain 4.19 g of Isomer A and 2.67 g of Isomer B of the subject compound, respectively as powders Isomer A: (2R, 6R, 9R, 10R)-isomer IR$\nu_{max}^{KBr}$ cm$^{-1}$: 3350, 1800 (sh), 1782, 1755, 1519, 1348.

NMR (90 MHz, CDCl$_3$)δ: 2.44–3.40 (5H, m), 3.63 (2H, s), 4.96 (1H, d, J=5 Hz), 5.35 (2H, s), 5.45 (1H, dd, J=5Hz, 9 Hz), 6.15 (1H, d, J=9 Hz), 7.33 (5H, s), 7.53 (2H, d, J=9 Hz), 7.33 (5H, s), 7.53 (2H, d, J=9 Hz), 8.22 (2H, d, J=9 Hz).

Isomer B: (2S, 6S, 9R, 10R)-isomer

IR$\nu_{max}^{KBr}$ cm$^{-1}$: 3360, 1810, 1773, 1748, 1680, 1520, 1346.

NMR (90 MHz, CDCl$_3$)δ: 2.35–3.35 (5H, m), 3.55 (2H, s), 5.03 (1H, d, J=4 Hz), 5.32 (2H, s), 5.46 (1H, dd, J=4 Hz, 9 Hz), 7.08 (1H, d, J=9 Hz), 7.25 (5H, s), 7.48 (2H, d, J=9 Hz), 8.15 (2H, d, J=9 Hz).

EXAMPLE 13

Production of sodium (2R, 6R, 9R, 10R)-4,11-dioxo-10-phenylacetamido-3-oxa-8-thia-1-azatricyclo[7,2,0,0$^{2,6}$]undecane-2-carboxylate In 4 ml of ethyl acetate was dissolved 0.15 g of Isomer A obtained in Example 12, to which were added 4 ml of a 0.1M phosphate buffer solution and 0.075 g of 10% palladium-carbon. The mixture was stirred for one hour at 8° to 10° C. while introducing hydrogen gas. To the reaction mixture was added 0.075 g of 10% palladium-carbon, which was stirred for further two hours. The catalyst was filtered off, and the aqueous layer was separated, followed by subjecting the remaining organic layer to extraction with 1 ml of water. The aqueous layers were combined and subjected to a Amberlite XAD-2 column chromatography. Fractions eluted with water-ethanol (90:10) were combined, from which ethanol was distilled off under reduced pressure, followed by freeze-drying the residue to obtain 0.08 g of the subject compound as powders.

IR$\nu_{max}^{KBr}$ cm$^{-1}$: 3340, 1785, 1770, 1670.

NMR (90 MHz, D$_2$O)δ: 2.65–3.33 (5H, m), 3.79 (2H, s), 5.22 (1H, d, J=4 Hz), 5.45 (1H, d, J=4 Hz), 7.46 (5H, s).

EXAMPLE 14

Production of sodium (2S, 6S, 9R, 10R)-4,11-dioxo-10-phenylacetamido-3-oxa-8-thia-1-azatricyclo[7,2,0,0$^{2,6}$]undecane-2-carboxylate In 4 ml of ethyl acetate was dissolved 0.15 g of Isomer B obtained in Example 12, to which were added 4 ml of a 0.1M buffer solution of pH 7.0 and 0.075 g of 10% palladium-carbon. The mixture was stirred for one hour at 8° to 10° C. while introducing hydrogen gas. To the reaction mixture was added 0.075 g of 10% palladium-carbon, which was stirred for further two hours. The catalyst was filtered off, and the aqueous layer was separated, followed by subjecting the remaining organic layer to extraction with 1 ml of water. The aqueous layers were combined and subjected to a Amberlite XAD-2 column chromatography. Fractions eluted with water-ethanol (90:10) were combined, from which ethanol was distilled off under reduced pressure, followed by freeze-drying the residue to obtain 0.07 g of the subject compound as powders.

IR$\nu_{max}^{KBr}$ cm$^{-1}$: 3440, 1802, 1795, 1753, 1655, 1358.

NMR (90 MHz, D$_2$O)δ: 2.70–3.60 (5H, m), 3.79 (2H, s), 5.36 (2H, s), 7.50 (5H, s).

EXAMPLE 15

Production of (4-nitro)benzyl (2R, 6R, 9R, 10R)-4,11-dioxo-10-phenylacetamido-3-oxa-8-thia-1-azatricyclo[7,2,0,0$^{2,6}$]undecane-2-carboxylate In 4 ml of anhydrous dichloromethane was dissolved 0.1 g of Isomer A obtained in Example 9. To the solution were added at −78° C. 0.092 g of N,N-dimethylaniline and 0.079 g of phosphorus pentachloride. The mixture was stirred at temperatures ranging from −45° C. to 40° C. for 1.5 hour. To the reaction mixture was added 0.2 ml of anhydrous methanol −78° C., and the mixture was stirred at temperatures ranging from −35° C. to −30° C. for 3 hours to which was added 2 ml water. The mixture was stirred for 30 minutes, followed by adding a saturated aqueous solution of sodium hydrogencarbonate to adjust the pH to 6.5. The organic layer was separated, and the remaining aqueous layer was subjected to extraction with 2 ml of dichloromethane. The organic layers were combined and washed with a saturated aqueous saline solution, followed by drying (MgSO$_4$). From the resultant was distilled off the solvent, and the residue was dissolved in 5 ml of dichloromethane. To this solution were added under ice-cooling 0.038 g of triethylamine and 0.044 g of phenylacetyl-chloride, and the mixture was stirred at the same temperature for 30 minutes. The reaction mixture was washed with 2N HCl then with a saturated aqeuous saline solution, followed by drying (MgSO$_4$). The solvent was distilled off under reduced pressure, and the residue was subjected to a silica gel column chromatography, followed by elution wih ethyl acetate-hexane (3:2). Fractions containing the end product were combined and concentrated under reduced pressure to give 0.07 g of the subject compound as powder. NMR spectrum of this product was in complete agreement with that of Isomer A obtained in Example 12.

EXAMPLE 16

Production of (4-nitro)benzyl (2R, 6R, 9R, 10R)-10-[2-(2-chloroacetamidothiazol-4-yl)-(Z)-2-methoxyiminoacetamido]-4,11-dioxo-3-oxa-8-thia-1-azatricyclo[7,2,0,0$^{2,6}$]undecane-2-carboxylate In 4 ml of anhydrous dichloromethane was dissolved 0.1 g of Isomer A obtained in Example 9. To the solution were added 0.092 g of N,N-dimethylaniline and 0.079 g of phosphorus pentachloride at −78° C., and the mixture was stirred for 1.5 hour at temperatures ranging from −45° C. to −40° C. To the reaction mixture was added 0.2 ml of anhydrous methanol at −78° C., and the mixture was stirred for 3 hours at temperatures ranging from −35° C. to −30° C., after which was added 2 ml of water. The mixture was stirred at 0° C. for 30 minutes, followed by adding a saturated aqueous solution of sodium hydrogencarbonate to make the pH to 6.5. The organic layer was separated, and the aqueous layer was extracted with 2 ml of dichloromethane. The organic layers were combined, washed with a saturated aqueous saline solution, followed by drying (MgSO$_4$). The solvent was distilled off under reduced pressure, and the residue was dissolved in 5 ml of dichloromethane. To this solution were added under ice-cooling 0.046 g of triethylamine and 0.076 g of hydrochloride of 2-(2-chloroacetamidothiazol-4-yl)-(Z)-2-methoxyiminoacetyl chloride. The mixture was stirred at the same temperature for 15 minutes. The reaction mixture was washed with 2N HCl then with a saturated saline solution, followed by drying (MgSO$_4$). The solvent was distilled off under reduced pressure, and the residue was subjected to a silica gel column chromatography. Elution was carried out with ethyl acetate-hexane (2:1), followed by subjecting fractions containing the end product to concentration under reduced pressure to give 0.086 g of the subject compound as powders.

IR$\nu_{max}^{KBr}$ cm$^{-1}$: 3450~3150, 1810, 1805, 1790, 1780, 1690, 1542, 1523, 1348.

NMR (90 MHz, CDCl$_3$)δ: 2.53–3.15 (5H, m), 4.07 (3H, s), 4.26 (2H, s), 5.14 (1H, d, J=5 Hz), 5.39 (2H, s), 5.68 (1H, dd, J=5 Hz, 9 Hz), 7.25 (1H, d, J=9 Hz), 7.41 (1H, s), 7.55 (2H, d, J=9 Hz), 8.21 (2H, d, J=9 Hz).

EXAMPLE 17

Production of (4-nitro)benzyl (2R, 6R, 9R, 10R)-10-[2-(2-aminothiazol-4-yl)-(Z)-2-methoxyiminoacetamido]-4,11-dioxo-3-oxa-8-thia-1-azatricyclo[7,2,0,0$^{2,6}$]undecane-2-carboxylate In 5 ml of anhydrous N,N-dimethylformamide was dissolved 0.334 g of the compound obtained in Example 16, to which was added 0.132 g of sodium N-methyldithiocarbamate, folowed by stirring at room temperature for 1.5 hour. To the reaction mixture was added 30 ml of ethyl acetate, which was washed with water and then dried (MgSO$_4$). The solvent was distilled off under reduced pressure, and the residue was subjected to a silica gel column chromatography, followed by elution with ethyl acetate-chloroform-methanol (15:15:1). Fractions containing the end product were combined and concentrated under reduced pressure to give 0.206 g of the subject compound as powders.

IR$\nu_{max}^{KBr}$ cm$^{-1}$: 3440, 3370, 1802, 1783, 1525, 1350.

NMR (90 MHz, DMSO-d$_6$)δ: 2.70–3.20 (5H, m), 3.86 (3H, s), 5.15 (1H, d, J=5 Hz), 5.30–5.60 (3H, m), 6.77 (1H, s), 7.14 (2H, s), 7.72 (2H, d, J=9 Hz), 8.23 (2H, d, J=9 Hz), 9.61 (1H, d, J=8 Hz).

EXAMPLE 18

Production of sodium (2R, 6R, 9R, 10R)-10-[2-(2-aminotiaxol-4-yl)-(Z)-2-methoxyiminoacetamido]-4,11-dioxo-3-oxa-8-thia-1-azatricyclo[7,2,0,0$^{2,6}$]undecane-2-carboxylate In 6 ml of ethyl acetate was dissolved 0.196 g of the compound obtained in Example 17. To this solution were added 6 ml of a 0.1M phosphate buffer solution of pH 7.0 and 0.1 g of 10% palladium-carbon. The mixture was stirred at 8° to 10° C. for 40 minutes while introducing hydrogen gas. To the reaction mixture was added 0.1 g of 10% palladium-carbon, and the mixture was stirred for further one hour. The catalyst was filtered off, and the aqueous layer was separated, followed by subjecting the organic layer to extraction with 1m of water. The aqueous layers were combined and subjected to a Amberlite XAD-2 column chromatography, followed by elution with water. Fractions containing the end product were combined and freeze-dried to give 0.127 g of the subject compound as powders.

IR$\nu_{max}^{KBr}$ cm$^{-1}$: 3420, 1790 (sh), 1780, 1775, 1665, 1650.

NMR (90 MHz, D$_2$O)δ: 2.73–3.10 (5H, m), 4.09 (3H, s), 5.37 (1H, d, J=4 Hz), 5.67 (1H, d, J=4 Hz), 7.17 (1H, s).

EXAMPLE 19

Production of (4-nitro)benzyl (2S,6S,9R,10R)-10-amino-4,11-dioxo-3-oxa-8-thia-1-azatricyclo[7,2,0,0$^{2,6}$]undecane-2-carboxylate hydrochloride In 15 ml of anhydrous dichloromethane was dissolved 1 g of Isomer B obtained in Example 12. To the solution were added at −78° C. 0.92 g of N,N-dimethylaniline and 0.79 g of phosphorus pentachloride, and the mixture was stirred at temperatures ranging from −60° C. to −55° C. for one hour. To the reaction mixture was added at −78° C. 1 ml of absolute methanol, and the mixture was stirred at temperatures ranging from −26° C. to −24° C. for 3.5 hours. To the resultant was added 10 ml of water, and the mixture was stirred for 30 minutes under ice-cooling, followed by collecting the precipitates by filtration. The precipitates were washed with water then with ether, followed by drying to give 0.606 g of the subject compound.

IR$\nu_{max}^{KBr}$cm$^{-1}$: 3430, 2785, 2600, 1804, 1773, 1744, 1525, 1352.

EXAMPLE 20

Production of (4-nitro)benzylethyl (2S,6S,9R,10R)-10-[2-(2-chloroacetamidothiazol-4-yl)-(Z)-2-methoxyiminoacetamido]-4,11-dioxo-3-oxa-8-thia-1-azatricyclo[7,2,0,0$^{2,6}$]undecane-2-carboxylate In 3 ml of dichloromethane was suspended 0.043 g of the compound obtained in Example 19, and thereto were added under ice-cooling 0.040 g of triethylamine and 0.040 g of hydrochloride of 2-(2-chloroacetamido-thiazol-4-yl)-(Z)-2-methoxyimino acetyl chloride. The mixture was stirred at the same temperature for 20 minutes. The reaction mixture was washed with 1N HCl, then with a saturated aqueous saline solution, followed by drying (MgSO$_4$). The solvent was distilled off under reduced pressure, and the residue was subjected to a silica gel column chromatography, followed by elution with ethyl acetate-hexane (3:1). Fractions containing the end product were combined and concentrated under reduced pressure to give 0.065 g of the subject compound as powders.

IR$\nu_{max}^{KBr}$cm$^{-1}$: 3270, 1813, 1780, 1750, 1690 1522, 1346.

NMR ((90 MHz, CDCl$_3$)$\delta$: 2.33–3.48(5H, m), 4.02(3H, s), 4.25(2H, s), 5.14(1H, d, J=4 Hz), 5.35(2H, s), 5.47(1H, dd, J=4 Hz, 10 Hz), 7.37(1H, s), 7.52(2H, d, J=9 Hz), 8.04(1H, d, J=10 Hz), 8.25(2H, d, J=9 Hz), 10.40(1H, br, s).

EXAMPLE 21

Production of (4-nitro)benzyl (2S,6S,9R,10R)-10-[2-(2-aminothiazol-4-yl)-(Z)-2-methoxyiminoacetamido]-4,11-dioxo-3-oxa-8-thia-1-azatricyclo[7,2,0,0$^{2,6}$]undecane-2-carboxylate In 8 ml of N,N-dimethylformamide was dissolved 0.359 g of the compound obtained in Example 20. To the solution were added 5 ml of a 0.1M phosphate buffer solution of pH 6.86 and 0.142 g of sodium N-methyldithiocarbamate, and the mixture was stirred at room temperature for 1.5 hour. To the reaction mixture was added 40 ml of ethyl acetate, and the mixture was washed with water and dried (MgSO$_4$). The solvent was distilled off under reduced pressure, and the residue was subjected to a silica gel column chromatography, followed by elution with ethy acetate-chloroform-methanol (10:10:1). Fractions containing the end product were combined and concentrated under reduced pressure to give 0.218 g of the subject compound as powders.

IR$\nu_{max}^{KBr}$cm$^{-1}$: 3340, 1812, 1784, 1753, 1665, 1522, 1347.

NMR (90 MHz, DMSO-d$_6$)$\delta$: 2.30–3.40(5H, m), 3.85(3H, s), 5.13(1H, d, J=5 Hz), 5.43(2H, s), 5.55 (1H, dd, J=5 Hz, 9 Hz), 6.68(1H, s), 7.15(2H, s), 7.71(2H, d, J=9 Hz), 8.26(2H, d, J=9 Hz), 9.53(1H, d, J=9 Hz)

EXAMPLE 22

Production of sodium (2S,6S,9R,10R)-10-[2-(2-aminothiazol-4-yl)-(Z)-2-methoxyiminoacetamido]-4,11-dioxo-3-oxa-8-thia-1-azatricyclo[7,2,0,0$^{2,6}$]undecane-2-carboxylate:

In 5 ml of ethyl acetate was suspended 0.218 g of the compound obtained in Example 21. To the suspension were added 5 ml of a 0.1M phosphate buffer solution of pH 7.0 and 0.12 g of 10% palladium-carbon, and the mixture was stirred for 50 minutes at temperatures ranging from 8° C. to 12° C. To the reaction mixture was added 0.12 g of 10% palladium-carbon, and the mixture was stirred for further two hours. The catalyst was filtered off, and the aqueous layer was separated, followed by subjecting the remaining organic layer to extraction with 1 ml of water. The aqueous layers were combined and subjected to a Amberlite XAD-2 column chromatography, followed by elution with water. Fractions containing the end product were combined and freeze-dried to give 0.104 g of the subject compound as powders.

IR$\nu_{max}^{KBr}$cm$^{-1}$: 3410, 1797, 1775, 1755, 1646, 1533.

NMR (90 MHz, D$_2$O)$\delta$: 2.70–3.33(5H, m), 4.07(3H, s), 5.46(1H, d, J=4 Hz), 5.55(1H, d, J=4 Hz), 7.15(1H, s).

EXAMPLE 23

Production of 4-nitrobenzyl (2R,6R,9R,10R)-4,11-dioxo-10-phenylacetamido-3-oxa-8-thia-1-azatricyclo[7,2,0,0$^{2,6}$]undecane-2-carboxylate, (2S,6S,9R,10R)-isomer and (2R,6S,9R,10R)-isomer In 50 ml of dichloromethane was dissolved the crude product of Compound (50) as obtained in Reference Example 50. To the solution was added 3.08 g of hydrochloride of 1-ethyl-3-(3-dimethylaminopropyl)carbodiimide under ice-cooling in nitrogen streams. The mixture was stirred at room temperature for 30 minutes. The solvent was distilled off under reduced pressure. The residue thus obtained was allowed to pass through a column of silica gel, followed by elution with ethyl acetate-hexane (4:3→2:1). Fractions containing the object compound were combined and concentrated under reduced pressure to give 2.09 g of (2R,6R,9R,10R)-isomer of the subject compound as crystals and 1.33 g of a mixture of (2S,6S,9R,10R)-isomer and (2R,6S,9R,10R)-isomer of the subject compound as powders. This mixture was dissolved in 5 ml of ethyl acetate, which was left standing. Precipitating crystals were collected by filtration to obtain 0.34 g of (2R,6S,9R,10R)-isomer of the subject compound. The filtrate was concentrated under reduced pressure to give 0.99 g of (2S,6S,9R,10R)-isomer of the subject compound. Incidentally, the (2R,6R,9R,10R)-isomer and the (2S,6S,9R,10R)-isomer were respectively identical with the isomer A and the isomer B as obtained in Example 12.

(2R,6S,9R,10R)-isomer: m.p. 216°–217° C. (decomp.).

IR$\nu_{max}^{KBr}$cm$^{-1}$: 3410, 1795, 1757, 1683, 1522, 1510, 1345.

NMR(90 MHz, CDCl$_3$)$\delta$: 2.00–3.43(5H, m), 3.62(2H, s), 5.32(2H, s), 5.40(1H, d, J=5 Hz), 5.72(1H, dd, J=5,9 Hz), 6.18(1H, d, J=9 Hz), 7.31(5H, s), 7.50(2H, d, J=9 Hz), 8.25(2H, d, J=9 Hz).

Elemental Analysis for C$_{24}$H$_{21}$N$_3$O$_8$S: Calcd.: C, 56.36; H, 4.14; N, 8.21; S, 6.27. Found: C, 56.48; H, 4.13; N, 8.21; S, 6.31.

EXAMPLE 24

Production of sodium
(2R,6S,9R,10R)-4,11-dioxo-10-phenylacetamido-3-oxa-8-thia-1-azatricyclo[7,2,0,0$^{2,6}$]undecane-2-carboxylate In 12 ml of ethyl acetate was dissolved 0.12 g of the (2R,6S,9R,10R)-isomer as obtained in Example 23. To the solution were added 6 ml of a 0.1M phosphate buffer solution of pH 7.0 and 0.075 g of 10% palladium-carbon. The mixture was stirred for 1 hour under ice-cooling while introducing hydrogen gas. To the reaction mixture was added 0.06 g of 10% palladium-carbon, which was stirred for further one hour. The catalyst was filtered off, and the aqueous layer was separated, followed by subjecting the organic layer to extraction with 2 ml of water. The extract and the aqueous layer were combined and allowed to pass through a column of Amberlite XAD-2, followed by elution with water-ethanol (9:1). The resulting fractions were combined, from which ethanol was distilled off, followed by lyophilizing the residue to give 0.038 g of the subject compound as powders.

IR$\nu_{max}^{KBr}$cm$^{-1}$: 3420, 1800, 1755, 1640.
NMR(90 MHz, D$_2$O)δ: 2.60–3.30(5H, m), 3.77(2H, s), 5.33(2H, s), 7.48(5H, s).

EXAMPLE 25

Production of 4-nitrobenzyl
(2R,6S,9R,10R)-10-[2-(2-chloroacetamidothiazol-4-yl)-(Z)-2-methoxyiminoacetamido]-4,11-dioxo-3-oxa-8-thia-1-azatricyclo[7,2,0,0$^{2,6}$]undecane-2-carboxylate In 15 ml of anhydrous dichloromethane was dissolved 0.1 g of the (2R,6S,9R,10R)-isomer as obtained in Example 23. To the solution were added at −78° C. 0.092 g of N,N-dimethylaniline and 0.079 g of phosphorus pentachloride. The mixture was stirred at temperatures ranging from −50° C. to −45° C. for 1 hour, to which was added 0.6 ml of absolute methanol, followed by stirring at temperatures ranging from −35° C. to −30° C. for 3 hours. To the reaction mixture was added 5 ml of ice-water, and the mixture was stirred at 0° C. for 30 minutes, followed by adding thereto a saturated aqueous solution of sodium hydrogencarbonate to bring the pH to 6.5. The organic layer was separated, and the aqueous layer was subjected to extraction with 3 ml of dichloromethane. The extract was combined with the organic layer and dried (MgSO$_4$). The solvent was distilled off under reduced pressure, and the residue was dissolved in 10 ml of dichloromethane. To the solution were added under ice-cooling 0.046 g of triethylamine and 0.076 g of hydrochloride of 2-(2-chloroacetamidothiazol-4-yl)-(Z)-2-methoxyiminoacetyl chloride. The mixture was stirred at the same temperature for 15 minutes. The reaciton mixture was washed with 2N HCl then with a saturated aqueous saline solution, followed by drying (MgSO$_4$). The solvent was distilled off under reduced pressure, and the residue was allowed to pass through a column of silica gel, followed by elution with ethyl acetate-hexane (3:1). Fractions containing the object compound were combined and concentrated under reduced pressure to give 0.097 g of the subject compound as a powder.

IR$\nu_{max}^{KBr}$cm$^{-1}$: 3330, 1800, 1750, 1690, 1524, 1347.
NMR(90 MHz, CDCl$_3$)δ: 2.30–3.47(5H, m), 4.07(3H, s), 4.28(2H, s), 5.39(2H, s), 5.54(1H, d, J=4 Hz), 5.88(1H, dd, J=4,9 Hz), 6.99(1H, d, J=9 Hz), 7.38(1H, s), 7.53(2H, d, J=9 Hz), 8.19(2H, d, J=9 Hz), 10.00(1H, br.s).

EXAMPLE 26

Production of 4-nitrobenzyl
(2R,6S,9R,10R)-10-[2-(2-aminothiazol-4-yl)-(Z)-2-methoxyiminoacetamido]-4,11-dioxo-3-oxa-8-thia-1-azatricyclo[7,2,0,0$^{2,6}$]undecane-2-carboxylate In 6 ml of N,N-dimethylformamide was dissolved 0.3 g of the compound as obtained in Example 25. To the solution were added under ice-cooling 2 ml of a 0.1M phosphate buffer solution of pH 7.0 and 0.119 g of sodium N-methyldithiocarbamate. The mixture was stirred at room temperature for 2 hours. To the reaction mixture was added 30 ml of ethyl acetate, followed by washing with water and drying (MgSO$_4$). The solvent was distilled off under reduced pressure, and the residue thus obtained was allowed to pass through a column of silica gel, followed by elution with ethyl acetat-chloroform-methanol (10:10:1). Fractions containing the object compound were combined and concentrated under reduced pressure to give 0.232 g of the subject compound as powders.

IR$\nu_{max}^{KBr}$cm$^{-1}$: 3360, 1800, 1752, 1665, 1521, 1346.
NMR(90 MHz, CDCl$_3$-MeOH-d$_6$)δ: 2.30–3.47(5H, m), 4.02(3H, s), 5.44(2H, ABq, J=13, 18 Hz), 5.59(1H, d, J=4 Hz), 5.78(1H, d, J=4 Hz), 6.83(1H, s), 7.62(2H, d, J=9 Hz), 8.24(2H, d, J=9 Hz).

EXAMPLE 27

Production of sodium
(2R,6S,9R,10R)-10-[2-(2-aminothiazol-4-yl)-(Z)-2-methoxyiminoacetamido]-4,11-dioxo-3-oxa-8-thia-1-azatricyclo[7,2,0,0$^{2,6}$]undecane-2-carboxylate In 6 ml of ethyl acetate was dissolved 0.09 g of the compound as obtaiend in Example 26. To the solution were added 5 ml of a 0.1M phosphate buffer solution of pH 7.0 and 0.04 g of 10% palladium carbon, and the mixture was stirred under ice-cooling for 1 hour, while introducing hydrogen gas. To the reaction mixture was added 0.04 g of 10% palladium-carbon, and the mixture was stirred for 1 hour, followed by supplementing 0.02 g of 10% palladium-carbon. The mixture was stirred for 1 hour. The catalyst was filtered off, and the aqueous layer was separated, then the organic layer was subjected to extraction with 1 ml of water. The extract was combined with the aqueous layer and allowed to pass through a column of Amberlite XAD-2, followed by elution with water then with 50% ethanol. Fractions containing the object compound were combined and lyophilized to obtain 0.054 g of the subject compound as powders.

SIMS m/z: 464 (M+1).
IR$\nu_{max}^{KBr}$cm$^{-1}$: 3420, 1782, 1648, 1532.
NMR(90 MHz, D$_2$O): 2.55–3.27(5H, m), 4.10(3H, s), 5.82(2H, s), 7.15(1H, s).

EXAMPLE 28

Production of 4-nitrobenzyl
(2R,6R,9R,10R)-10-[2-(2-chloroacetamidothiazol-4-yl)-(Z)-2-[1-(4-nitrobenzyloxycarbonyl)-1-methylethoxyimino]acetamido]-4,11-dioxo-3-oxa-8-thia-1-azatricyclo[7,2,0,0$^{2,6}$]-undecane-2-carboxylate In 10 ml of anhydrous dichloromethane was dissolved 0.25 g of the (2R,6R,9R,10R)-isomer as obtained in Example 23. To the solution were added at −78° C.

0.23 g of N,N-dimethylaniline and 0.198 g of phosphorus pentachloride. The mixture was stirred for 1 hour at 31 50° C. to −45° C. To the reaction mixture was added 0.6 ml of absolute methanol at −78° C. The mixture was stirred for 3 hours at −25° C. to −24° C., to which was added 5 ml of ice-water, followed by stirring for 30 minutes at 0° C. To the resulting mixtrue was added a saturated aqueous solution of sodium hydrogencarbonate to adjust the pH at 6.5. The organic layer was separated, and the aqueous layer was extracted with 3 ml of dichloromethane. The extract was combined with the organic layer and dried (MgSO$_4$). The solvent was distilled off under reduced pressure, and the residue was dissolved in 10 ml of dichloromethane. To the solution were added under ice-cooling 0.116 g of triehtylamine and 0.287 g of 2-(2-chloroacetamidothiazol-4-yl)-(Z)-2-[1-(4-nitrobenzyloxycarbonyl)-1-methylethoxyimino]acetyl chloride.monohydrochloride. The mixture was stirred at the same temperature for 15 minutes. The reaction mixture was washed with 2N HCl and dried (MgSO$_4$). The solvent was distilled off under reduced pressure, and the residue was allowed to pass through a column of silica gel, followed by elution with ethyl acetate-hexane (3:2). Fractions containing the object compound were combined and concentrated under reduced pressure to give 0.42 g of the subject compound as powders.

IR$\nu^{KBr}_{max}$cm$^{-1}$: 3400, 1785, 1753, 1690, 1525, 1347.

NMR(90 MHz, CDCl$_3$)δ: 1.64(3H, s), 1.70(3H, s), 2.40-3.40(5H, m), 4.28(2H, s), 5.12(1H, d, J=5 Hz), 5.25(2H, s), 5.40(2H, s), 5.65(1H, dd, J=5,9 Hz), 7.26(1H, s), 7.42(1H, d, J=9 Hz), 7.55(2H, d, J=9 Hz), 7.58(2H, d, J=9 Hz), 8.12(2H, d, J=9 Hz), 8.22(2H, d, J=9 Hz).

EXAMPLE 29

Production of 4-nitrobenzyl (2R,6R,9R,10R)-10-82-(2-aminothiazol-4-yl)-(Z)-2-[1-(-4-nitrobenzyloxycarbonyl)-1-methylethoxyimino]acetamido]-4,11-dioxo-3-oxa-8-thia-1-azatricyclo[7,2,0,0$^{2,6}$]undecane-2-carboxylate In 5 ml of N,N-dimethylformamide was dissolved 0.383 g of the compound as obtained in Example 28. To the solution were added under ice-cooling 2 ml of a 0.1M phosphate buffer solution of pH 7.0 and 0.115 g of sodium N-methyldithiocarbamate. The mixture was stirred for 1.5 hour at room temperature, to which was added 30 ml of ethyl acetate, followed by washing with water then drying (MgSO$_4$). The solvent was distilled off under reduced pressure, and the residue was allowed to pass through a column of silica gel, followed by elution with ethyl acetate-hexane (3:1). Fractions containing the object compound were combined and concentrated under reduced pressure to give 0.26 g of the subject compound as powders.

IR$\nu_{max}^{KBr}$cm$^{-1}$: 3450, 3375, 1785, 1752, 1522, 1347.

NMR(90 MHz, DMSO-d$_6$)δ: 1.49(6H, s), 2.40-3.40(5H, m), 5.18(1H, d, J=5 Hz), 5.32(2H, s), 5.38(2H, ABq, J=13, 18 Hz), 5.55(1H, dd, J=5, 8 Hz), 6.75(1H, s), 7.28(2H, br.s), 7.62(2H, d, J=9 Hz), 7.70(2H, d, J=9 Hz), 8.12(2H, d, J=9 Hz), 8.22(2H, d, J=9 Hz), 9.55(1H, d, J=8 Hz).

EXAMPLE 30

Production of sodium (2R,6R,9R,10R)-10-[2-(2-aminothiazol-4-yl)-(Z)-2-(2-(1-carboxy-1-methylethoxyimino)acetamido]-4,11-dioxo-3-oxa-8-thia-1-azatricyclo[7,2,0,0$^{2,6}$]undecane-2-carboxylate In 8 ml of ethyl acetate was dissolved 0.235 g of the compound as obtained in Example 29. To the solution were added 5 ml of a 0.1M phosphate buffer of pH 7.0 and 0.1 g of 10% palladium-carbon, which was stirred at 12°-15° C. for 1 hour while introducing hydrogen gas. To the reaction mixture was added 0.1 g of 10% palladium-carbon, which was stirred for 1 hour. To the resulting mixture was supplementally added 0.1 g of 10% palladium-carbon, which was stirred for 1 hour. The catalyst was filtered off, and the aqueous layer was separated, and the organic layer was extracted with 3 ml of water. The extract was combined with the aqueous layer and allowed to pass through a column of Amberlite XAD-2, followed by elution with water. Fractions containing the object compound were combined and lyophilized to give 0.113 g of the subject compound as a powdery product.

SIMS m/z: 558(M+1), 580(M+Na).

IR$\nu_{max}^{KBr}$cm$^{-1}$: 3425, 1770, 1660, 1590, 1535, 1365.

NMR(90 MHz, D$_2$O)δ: 1.58(3H, s), 1.61(3H, s), 2.70-3.47(5H, m), 5.37(1H, d, J=4 Hz), 5.69(1H, d, J=4 Hz), 7.14(1H, s).

EXAMPLE 31

Production of 4-nitrobenzyl (2R,6R,9R,10R)-10-[2-(2-chloroacetamidothiazol-4-yl)acetamido]-4,11-dioxo-3-oxa-8-thia-1-azatricyclo[7,2,0,0$^{2,6}$]undecane-2-carboxylate In 7 ml of anhydrous dichloromethane was dissolved 0.1 g of the (2R,6R,9R,10R)-isomer as obtained in Example 23. To the solution were added at −78° C. 0.078 g of N,N-dimethylaniline and 0.08 g of phopshorus pentachloride, which was stirred for 1 hour at temperatures ranging from −50° C. to −45° C. To the reaction mixture was added 0.3 ml of absolute methanol at −78° C., followed by stirring for 3 hours at temperatures ranging from −25° C. to −24° C. To the mixture was added 3 ml of ice-water, which was stirred at 0° C. for 30 minutes, followed by adding a saturated aqueous solution of sodium hydrogencarbonate to adjust the pH at 6.5. The organic layer was separated, and the aqueous layer was subjeeted to extraction with 3 ml of dichloromethane. The combined organic layer was dried (MgSO$_4$) and concentrated under reduced pressure to a volume of about 5 ml to give the solution of the corresponding 10-amino compound.

To 0.5 ml of dimethylformamide were dissolved 0.058 g of 2-(2-chloroacetamidothiazol-4-yl)acetic acid and 0.038 g of 1-hydroxy-1H-benzotriazole.monohydrate. To the solution were added under ice-cooling 3 ml of dichloromethane and 0.051 g of dicyclohexylcarbodiimide, and the mixture was stirred at room temperature for 1 hour. To the reaction mixture was added the solution containing said 10-amino compound, followed by stirring at room temperature for 2 hours. Insolubles were filtered off, and the filtrate was concentrated under reduced pressure. The residue was dissolved in 10 ml of ethyl acetate, and it was washed with a saturated aqueous solution of sodium hdyrogencarbonate, 2N HCl and a saturated aqueous saline solution in seqence, followed by drying (MgSO$_4$). The solvent was distilled off under reduced pressure, and the residue was allowed to pass through a column of silica gel, followed by elution with ethyl acetate-hexane (3:1 to 4:1). Fractions containing the object compound were combined and concentrated under reduced pressure to give 0.062 g of the subject compound as powders.

FD-MS m/z: 610(M+1).

IR$\nu_{max}^{KBr}$cm$^{-1}$: 3300, 1783, 1760, 1690, 1522, 1348.

NMR(90 MHz, DMSO-d$_6$)δ: 2.70–3.40(5H, m), 3.60(2H, ABq, J=27, 30 Hz), 4.30(2H, s), 5.29(1H, d, J=4 Hz), 5.35(1H, dd, J=4,9 Hz), 5.42(2H, ABq, J=14,17 Hz), 6.93(1H, s), 7.71(2H, d, J=9 Hz), 8.22(2H, d, J=9 Hz), 8.98(1H, d, J=9 Hz).

EXAMPLE 32

Production of 4-nitrobenzyl (2R,6R,9R,10R)-10-[2-(2-aminothiazol-4-yl)acetamido]-4,11-dioxo-3-oxa-8-thia-1-azatricyclo[7,2,0,0$^{2,6}$]undecane-2-carboxylate In 6 ml of N,N-dimethylformamide was dissolved 0.255 g of the compound as obtained in Example 31. To the solution were added under ice-cooling 2 ml of a 0.1M phosphate buffer solution and 0.108 g of sodium N-methyldithiocarbamate. The mixture was stirred at room temperature for 2 hours. To the reaction mixture was added 20 ml of ethyl acetate, followed by washing with water and drying (MgSO$_4$). The solvent was distilled off under reduced pressure, and the residue was allowed to pass through a column of silica gel, followed by elution with ethyl acetate-chloroform-methanol (10:10:1). Fractions containing the object compound were combined and concentrated to give 0.144 g of the subject compound as powders.

FD-MS m/z: 534(M+1).

IR$\nu_{max}^{KBr}$cm$^{-1}$: 3350, 1780, 1677, 1518, 1346.

NMR(90 MHz, DMSO-d$_6$)δ: 2.55–3.60 (7H, m), 5.07(1H, d, J=5 Hz), 5.34(1H, dd, J=5,9 Hz), 5.38(2H, ABq, J=13,18 Hz), 6.23(1H, s), 6.78(2H, s), 7.71(2H, d, J=9 Hz), 8.24(2H, d, J=9 Hz), 8.87(1H, d, J=9 Hz).

EXAMPLE 33

Production of sodium (2R,6R,9R,10R)-10-[2-(2-aminotiazol-4-yl) acetamido]-4,11-dioxo-3-oxa-8-thia-1-azatricyclo[7,2,0,0$^{2,6}$] undecane-2-carboxylate In 5 ml of ethyl acetate was dissolved 0.137 g of the compound as obtained in Example 32. To the solution were added 5 ml of a 0.1M phosphate buffer solution and 0.07 g of 10% palladium-carbon. The mixture was stirred for 1 hour at temperatures ranging from 10° C. to 15° C., while introducing hydrogen gas. To the reaction mixture was added 0.05 g of 10% palladium-carbon, and it was stirred for 1 hour, followed by supplementing 0.05 g of 10% palladium-carbon and stirring for 1 hour. The catalyst was filtered off, and the aqueous layer was separated, then the organic layer was subjected to extraction with 2 ml of water. The extract was combined with the aqueous layer, which was allowed to pass through a column of Amberlite XAD-2. The column was subjected to elution with water, and fractions containing the object compound were combined and lyophilized to obtain 0.07 g of the subject compound as powders.

IR$\nu_{max}^{KBr}$ cm$^{-1}$: 3410, 1773, 1667, 1650, 1520.

NMR(90 MHz, D$_2$O) δ: 2.75–3.35(5H, m), 3.67(2H, s), 5.24(1H, d, J=5 Hz), 5.48(1H, d, J=5 Hz), 6.61(1H, s).

EXAMPLE 34

Production of 4-nitrobenzyl (2R, 6R, 9R, 10R)-10-[2-(2-chloroacetamidothiazol-4-yl)-(Z)-2-(4-nitrobenzyloxycarbonylmethoxyimino)acetamido]-4,11-dioxo-3-oxa-8-thia-1-azatricyclo[7,2,0,0$^{2,6}$]undecane-2-carboxylate In 10 ml of anhydrous dichlormethane was dissolved 0.3 g of the (2R,6R,9R,10R)-isomer as obtained in Example 23. To the solution were added at −78° C. 0.284 g of N,N-dimethylaniline and 0.245 g of phosphorus pentachloride, and the mixture was stirred for 1 hour at temperatures ranging from −50° C. to −45° C. To the reaction mixture was added 0.8 ml of absolute methanol at −78° C., and the mixture was stirred for 3 hours at −25° C. to −24° C. To the resulting mixture was added 10 ml of ice-water, and the mixture was stirred at 0° C. for 30 minutes, followed by adding a saturated aqueous solution of sodium hydrogencarbonate to adjust the pH at 6.5. The organic layer was separated, and the aqueous layer was subjected to extraction with 5 ml of dichloromethane. The combined organic layer was dried (MgSO$_4$) and concentrated under reduced pressure to a volume of about 10 ml to give the solution the corresponding 10-amino compound. To the solution were added under ice-cooling 0.143 g of triethylamine and 0.364 g of 2-(2-chloroacetamidothiazol-4-yl)-2-(4-nitrobenzyloxycarbonylmethoxyimino)acetyl chloride monohydrochloride, and the mixture was stirred at the same temperature for 15 minutes. The solvent was distilled off under reduced pressure, and the residue was allowed to pass through a column of silica gel, followed by elution with ethyl acetate-hexane (2:1). Fractions containing the object compound were combined and concentrated under reduced pressure to give 0.438 g of the subject compound as powders.

FD-MS $^m$/z:832 (M+1).

IR$\nu_{max}^{KBr}$ cm$^{-1}$: 3350, 1785, 1763, 1690, 1525, 1350

NMR (90 MHz, CDCl$_3$)δ: 2.40–3.45 (5H, m), 4.26 (2H, s), 4.96 (2H, s), 5.10 (1H, d, J=5 Hz), 5.27 (2H, s), 5.39 (2 H, s), 5.62 (1H, bd, J=5, 9 Hz), 7.26 (1H, s), 7.50 (2H, d, J=9 Hz), 7.58 (2H, d, J=9 Hz), 8.07 (1 H, d, J=9 Hz), 8.23 (4H, d, J=9 Hz).

EXAMPLE 35

Production of 4-nitrobenzyl (2R,6R,9R,10R)-10-[2-(2-aminothiazol-4-yl)-(Z)-2-(4-nitrobenzyloxycarbonylmethoxyimino)acetamido]-4,11-dioxo-3-oxa-8-thia-1-azatricyclo[7,2,0,0$^{2,6}$]undecane-2-carboxylate In 6 ml of N,N-dimethylformamide was dissolved 0.41 g of the compound as obtained in Example 34. To the solution were added under ice-cooling 2 ml of a 0.1M phosphate buffer solution of pH 7.0 and 0.127 g of sodium N-methyldithiocarbamate, and the mixture was stirred for 2 hours at room temperature. To the reaction mixture was added 20 ml of ethyl acetate, and it was washed with water, followed by drying (MgSO$_4$). The solvent was distilled off under reduced pressure, and the residue was allowed to pass through a column of silica gel, followed by elution with ethyl acetate-chloroform-methanol (10:10:1). Fractions containing the object compound were combined and concentrated under reduced pressure to obtain 0.315 g of the subject compound as powders.

FD-MS m/z: 756 (M+1).

IR$\nu_{max}^{KBr}$cm$^{-1}$: 3475–3250, 1782, 1760, 1685, 1522, 1348.

NMR (90 MHz, DNSO-d$_6$)δ: 2.70–3.45 (5H, m), 4.78(2H, s), 5.16 (1H, d, J=5 Hz), 5.33(2 H, s), 5.40(2H, ABq, J=15, 21 Hz), 5.52 (1H, d, J=5,9 Hz), 6.83(1 H, s), 7.21(2H, s), 7.65(2H, d, J=9 Hz), 7.68(2H, d, J=9 Hz), 8.18(2H, d, J=9 Hz) , 9.62(1H, d, J=9 Hz).

EXAMPLE 36

Production of sodium (2R,6R,9R,10R)-10-[2-(2-aminothiazol-4-yl)-(Z)-2-carboxymethoxyiminoacetamido]-4,11-dioxo-4,11-dioxo-3-oxa-8-thia-1-azatricyclo[7,2,0,0$^{2,6}$]undecane-2-carboxylate In 10 ml of ethyl acetate was dissolved 0.29 g of the compound as obtained in Example 35. To the solution were added 8 ml of a 0.1 M phosphate buffer solution of pH 7.0 and 0.15 g of 10% palladium-carbon. The mixture was stirred for 1 hour at temperatures ranging from 15° C. to 20° C., under a hydrogen gas atmosphere.

To the reaction mixture was added 0.15 g of 10% palladium-carbon, carbon, and the mixture was stirred for 1 hour, and treated with 0.07 g of additional 10% palladium-carbon, followed by stirring for 1 hour. The catalyst was filtered off, and the aqueous layer was separated, followed by subjecting the organic layer to extraction with 2 ml of water. The extract was combined with the aqueous layer and allowed to pass thorugh a column of Amberlite XAD-2, followed by elution with water. Fractions containing the object compound were combined and lyophilized to give 0.144 g of the subject compound as a powdery product.

SIMS m/z: 530(M+1), 552(M+Na).

IR$\nu_{max}^{KBr}$cm$^{-1}$: 3425, 1770, 1653, 1610, 1530.

NMR(90 MHz, D$_2$O)δ: 2.65–3.40(5H, m), 4.66(2H, s), 5.34(1H, d, J=4 Hz), 5.67(1H, d, J=4 Hz), 7.17(1H, s).

EXAMPLE 37

Production of 4-nitrobenzyl (2R,6R,9R,10R)-10-[2-(2-aminothiazol-4-yl)-(Z)-2-methoxyiminoacetamido]-4,11-dioxo-3-oxa-8-thia-1-azatricyclo[7,2,0,0$^{2,6}$]undecane-2-carboxylate In 10 ml of anhydrous dichloromethane was dissolved 0.35 g of the (2R,6R,9R,10R)-isomer as obtained in Example 23. To the solution were added at −78° C. 332 g of N,N-dimethylaniline and 0.285 g of phosphorus pentachloride, and the mixture was stirred for 1 hour at temperatures ranging from −50° C. to −45° C. To the reaction mixture was added at −78° C. 1.5 ml of absolute methanol, and the mixture was stirred for 3 hours at −25° C. to −24° C. To the resulting mixture was added 8 ml of ice-water, which was stirred at 0° C. for 30 minutes, followed by addition of a saturated aqueous solution of sodium hydrogencarbonate to adjust the pH at 6.5. To organic layer was separated, and the aqueous layer was subjected to extraction with 5 ml of dichloromethane. The combined organic layer was dried (MgSO$_4$) and concentrated under reduced pressure to a volume of about 8 ml to give the solution or the corresponding 10-amino compound solution were added 2 ml of N,N-dimethylformamide and 0.24 g of 2-benzothiazolyl 2-(2-aminothiadiazol-4-yl)-(Z)-2-methoxyiminothioacetate, and the mixture was stirred at room temperature for 18 hours. The solvent was distilled off under reduced pressure, and the residue was dissolved in a mixture of 40 ml of ethyl acetate and 10 ml of tetrahydrofuran. The solution was washed with 2N HCl, a saturated aqueous solution of sodium hydrogencarbonate and an aqueous saline solution in sequence, followed by drying (MgSO$_4$). The solvent was distilled off under reduced pressure, and the residue was allowed to pass through a column of silica gel, followed by elution with ethyl acetate-chloroform-methanol (12:12:1). Fractions containing the object compound were combined and concentrated under reduced pressure to obtain 0.182 g of the subject compound as powders.

IR$\nu_{max}^{KBr}$cm$^{-1}$: 3430, 3340, 1782, 1682, 1523, 1347.

NMR(90 MHz,DMSO-d$_6$)δ: 2.70–3.40(5H,m), 3.90(3H, s), 5.17 (1H, d, J=5 Hz), 5.38(2H, ABq, J=12,19 Hz), 5.60(1H, dd, J=5,9 Hz, C$_{10}$-H), 7.70(2H, d, J=9 Hz), 8.08(2H, s, NH$_2$), 8.25(2H, d, J=9 Hz), 9.63(1H, d, J=9 Hz).

EXAMPLE 38

Production of sodium (2R,6R,9R,10R)-10-[2-(2-aminothiadiazol-4-yl)-(Z)-2-methoxyiminoacetamido]-4,11-dioxo-3-oxa-8-thia-1-azatricyclo[7,2,0,0$^{2,6}$]undecane-2-carboxylate In 10 ml of ethyl acetate was dissolved 0.157 g of the compound as obtained in Example 37. To the solution were added 6 ml of a 0.1 M phosphate buffer solution of pH 7.0 and 0.1 g of 10% palladium-carbon. The mixture was stirred for 1 hour at temperature ranging from 15° C. to 20° C. while introducing hydrogen gas. To the reaction mixture was added 0.07 g of 10% palladium-carbon, which was stirred for 1 hour. To the resulting mixture was further added 0.07 g of 10% palladium-carbon, which was stirred for 1 hour. The catalyst was filtered off, and the aqueous layer was separated, followed by subjecting the organic layer to extraction with 3 ml of water. The extract was combined with the aqueous layer and allowed to pass through a column of Amberlite XAD-2, followed by elution with water. Fractions containing the object compound were combined and lyophilized to obtain 0.083 g of the subject compound as powders.

SIMS m/z: 465(M+1).

IR$\nu_{max}^{KBr}$cm$^{-1}$: 3420, 1770, 1650.

NMR(90 MHz, D$_2$O)δ: 2.75–3.36(5H, m), 4.19(3H, s), 5.38(1H, d, J=5 Hz), 5.72(1H, d, J=5 Hz).

EXAMPLE 39

Production of 4-nitrobenzyl (2R,6R,9R,10R)-4,11-dioxo-10-(D-2-hydroxy-2-phenylacetamido)-3-oxa-8-thia-1-azatricyclo[7,2,0,0$^{2,6}$]undecane-2-carboxylate In 10 ml of anhydrous dichloromethane was dissolved in 0.4 g of the (2R,6R,9R,10R)-isomer as obtained in Example 23. To the solution were added at −78° C., 0.38 g of N,N-dimethylaniline and 0.326 g of phosphorus pentachloride, and the mixture was stirred for 1 hour at temperatures ranging from −50° C. to −45° C. To the reaction mixture was added at −78° C. 1 ml of absolute methanol, and the mixture was stirred for 3 hours at temperatures ranging from −25° C. to −24° C. To resulting mixture was added 5 ml of ice-water, which was stirred for 30 minutes at 0° C., followed by adding a saturated aqueous solution of sodium hydrogencarbonate to adjust the pH at 6.5. The organic layer was separated, and the aqueous layer was subjected to extraction with 3 ml of dichloromethane. The combined organic layer was dried (MgSO$_4$) and concentrated under reduced pressure to a volum of about 8 ml. to give the solution of the corresponding 10-amino compound. To the solution were added 0.238 g f D-mandelic acid, 0.132 g of 1-hydroxy-1 H-benzotriazole monohydrate and 0.356 g of dicyclohexylcarbodiimide, and the mixture was stirred at room temperature for 2 hours. The solvent was distilled off under reduced pressure. To the residue was added 30 ml of ethyl acetate, and insolubles were filtered off. The filtrate was washed with a saturated aqueous solution of hydrogencarbonate, water and 2N HCl in sequence, followed by drying (MgSO$_4$). The solvent was distilled off under reduced pressure, the residue was allowed to pass through a column of silica gel, followed by elution with ethyl acetate–hexane (3:2). Fractions containing the object compound were combined and concentrated to give 0.226 g of the subject compound as powders.

IR$\nu_{max}^{KBr}$cm$^{-1}$: 3400, 1802, 1781, 1755, 1680, 1520, 1348.

NMR(90 MHz,CDCl$_3$)δ: 2.45–3.43(6H, m), 4.99(1H, d, J=5 Hz), 5.34(1H, s), 5.37(2H, s), 5.44(1H, dd, J=5,9 Hz), 7.37(5H, s), 7.37(1H, d, J=9 Hz), 7.53(2H, d, J=9 Hz), 8.20(2H, d, J=9 Hz).

EXAMPLE 40

Production of sodium (2R,6R,9R,10R)-4,11-dioxo-10-(D-2-hydroxy-2-phenylacetamido)-3-oxa-8-thia-1-azatricyclo[7,2,0,0$^{2,6}$]undecane-2-carboxylate In 10 ml of ethyl acetate was dissolved 0.2 g of the compound as obtained in Example 39. To the solution were added 6 ml of a 0.1 M phosphate buffer solution and 0.1 g of 10% palladium-carbon. The mixture was stirred for 1 hour at 12° C. to 15° C. while introducing hydrogen gas. To the reaction mixture was added 0.1 g of 10% palladium-carbon, which was stirred for 1 hour. To the resulting mixture was further added 0.5 g of 10% palladium-carbon, and it was stirred for 1 hour. The catalyst was filtered off, and the aqueous layer was separated, followed by subjecting the organic layer to extraction with 3 ml of water. The extract was combined with the aqueous layer and allowed to pass through a column of Amberlite XAD-2, followed by elution with water then with 10% ethanol. Fractions containing the object compound were combined and lyophized to obtain b 0.1 g of the subject compound as powders.

IR$\nu_{max}^{KBr}$cm$^{-1}$: 3425, 1773, 1652, 1360.

NMR(90 MHz,D$_2$O)δ: 2.60–3.35(5H, m), 5.26(1H, d, J=5 Hz), 5.38(1H, s), 5.50(1H, d, J=5 Hz), 7.59(5H, s).

EXAMPLE 41

Production of 4-nitrobenzyl (9R,10S)-4,11-dioxo-10-methoxy-10-phenylacetamido-3-oxa-8-thia-1-azatricyclo[7,2,0,0$^{2,6}$]undecane-2-carboxylate In 10 ml of dichloromethane was dissolved the crude product of Compound (54) as obtained in Reference Example 54. To the solution was added under ice-cooling in nitrogen streams 0.93 of hydrochloride of 1-ethyl-3-(3-dimethylaminopropyl)carbodiimide, and the mixture was stirred at room temperature for 15 minutes. The solvent was distilled off under reduced pressure, and the residue was allowed to pass through a column of silica gel, followed by elution with ethyl acetate-hexane (3:2 to 2:1). Fractions containing the object compound were combined and concentrated under reduced pressure to obtain the isomer A and a mixture of the isomers B and C as powders respectively in a yield of 0.32 g and 0.353 g.

Isomer A

FD-MS m/z: 541(M+).

IR$\nu_{max}^{KBr}$cm$^{-1}$: 3345, 1800, 1777, 1680, 1517, 1343.

NMR(90 MHz,CDCl$_3$)δ: 2.35–3.40(5H, m), 3.42(3H, s), 3.68(2H, s), 4.83(1H, s), 5.39(2H, s), 6.05(1H, s), 7.37(5H, s), 7.62(2H, d, J=9 Hz), 8.20(2H, d, J=9 Hz).

Mixture of Isomer B and Isomer C

FD-MS m/z: 541(M+).

IR$\nu_{max}^{KBr}$cm$^{-1}$: 3330, 1811, 1775, 1680, 1515, 1343.

EXAMPLE 42

Production of sodium (9R,10S)-4,11-dioxo-10-methoxy-10-phenylacetamido-3-oxa-8-thia-1-azatricyclo[7,2,0,0$^{2,6}$]undecane-2-carboxylate In 4 ml of ethyl acetate was dissolved 0.20 g of the isomer A as obtained in Example 41. To the solution were added 4 ml of a 0.1 M phosphate buffer solution of pH 7.0 and 0.1 g of 10% palladium-carbon, and the mixture was stirred for 1 hour at temperatures ranging from 8° C. to 12° C. To the reaction mixture was added 0.1 g of 10% palladium-carbon, and the mixture was stirred for 1 hour, followed by further addition of 0.05 g of 10% palladium-carbon. The mixture was stirred for 1 hour, from which was removed the catalyst by filtration. The aqueous layer was separated, and the remaining organic layer was subjected to extraction with 2 ml of water. The extract was combined with the aqueous layer and allowed to pass through a column of Amberlite XAD-2, followed by elution with water then with 10% ethanol. Fractions containing the object compound were combined and lyophilized to give 0.128 g of the isomer A of the subject compound as powders.

IR$\nu_{max}^{KBr}$cm$^{-1}$: 3420, 1768, 1652.

NMR(90 MHz, D$_2$O)δ: 2.63–3.34(5H, m), 3.54(3H, s), 3.81(2H, s), 5.26(1H, s), 7.54(5H, s).

EXAMPLE 43

Production of sodium (9R,10S)-4,11-dioxo-10-methoxy-10-phenylacetamido-3-oxa-8-thia-1-azatricyclo[7,2,0,0$^{2,6}$]undecane-2-carboxylate In 4 ml of ethyl acetate was dissolved 0.208 g of a mixture of the isomers B and C as obtained in Example 41. To the solution were added 4 ml of a 0.1 M phosphate buffer solution of pH 7.0 and 0.1 g of 10% palladium-carbon. The mixture was stirred for 1 hour at temperature ranging from 8° C. to 14° C. while introducing hydrogen gas. To the reaction mixture was added 0.1 g of 10% palladium-carbon, and the mixture was stirred for 1 hour, to which was further added 0.05 g of 10% palladium-carbon, followed by stirring for 1 hour. The catalyst was filtered off, and the aqueous layer was separated. The remaining organic layer was subjected to extraction with 2 ml of water. The extract was combined with the aqueous layer and allowed to pass through a column of Amberlite XAD-2, followed by elution with water then with 10% ethanol. Fractions containing the object compound were combined and lyophilized to obtain 0.124 g of the isomer B of the subject compound as powders.

IR$\nu_{max}^{KBr}$cm$^{-1}$: 3450, 1795, 1757, 1642, 1630.

NMR(90 MHz,D$_2$O)δ: 2.65–3.56(5H, m), 3.59(3H, s), 3.82(2H, s), 5.41(1H, s), 7.53(5H, s).

EXAMPLE 44

Production of 4-nitrobenzyl (9R,10R)-5,5-dimethyl-4,11-dioxo-3-oxa-10-phenylacetamido-8-thia-1-azatricclo[7,2,0,0$^{2,6}$]undecane-2-carboxylate In 2 ml of trifluoroacetic acid were dissolved 43 mg of Compound (68a) as obtained in Reference Example 68 and 0.3 ml of anisole, and the solution was stirred in nitrogen streams under ice-cooling for 70 minutes. The solvent was distilled off under reduced pressure. To the residue were added an aqueous volume of hexane and dichloromethane, and the mixture was concentrated under reduced pressure. This procedure was repeated twice, and the resulting residue was washed with hexane twice to eliminate materials soluble in hexane. The residue thus obtained was allowed to pass through a column of silica gel, followed by elution with ethyl acetate-hexane (1:1). Fractions containing the object compound were combined and concentrated under reduced pressure to give 27.5 mg of the isomer A of the subject compound as an oily product.

IR$\nu_{max}^{CHCl_3}$cm$^{-1}$: 1755, 1690.

NMR(90 MHz,CDCl$_3$)δ: 1.12(3H, s), 1.27(3H, s), 2.59–2.66 (1H, m), 2.87–2.95(2H, m), 3.63(2H, q), 5.00(1H, d, J=5 Hz), 5.38(2H, q), 5.55(1H, dd, J=9 Hz), 6.19(1H, bd, J=9 Hz), 7.26–7.39(5H, m), 7.55(2H, d, J=9 Hz), 8.21(2H, d, J=9 Hz).

EXAMPLE 45

Production of 4-nitrobenzyl (9R,10R)-5,5-dimethyl-4,11-dioxa-10-phenylacetamido-8-thia-1-azatricyclo[7,2,0,0$^{2,6}$]undecane-2-carboxylate In 3 ml of dichloromethane were dissolved 43 mg of Compound (69) as obtained in Reference Example 69 and 30 mg of hydrochloride of 1-ethyl-3-(3-dimethylaminopropyl)carbodiimide. The solution was stirred in nitrogen streams for 80 minutes under ice-cooling, then for 4 hours at room temperature. The solvent was distilled off under reduced pressure, and the residue was allowed to pass through a column of silica gel, followed by elution with ethyl acetate-hexane (1:1). Fractions containing the object compound were combined and concentrated under reduced pressure to give 18 mg of the isomer B the subject compound as an oily product.

IR$\nu_{max}^{CHCl_3}$cm$^{-1}$: 1800, 1780, 1755.

NMR(90MHz,CDCl$_3$)δ: 1.19(3H, s), 1.30(3H, s), 2.55(1H, dd, J=8,14 Hz), 2.72(1H, dd, J=5,8 Hz), 2.79(1H, dd, J=5,14 Hz), 3.66(2H, d, J=2 Hz), 5.07(1H, d, J=4 Hz), 5.37(2H, q), 5.45(1H, dd, J=4,8 Hz), 6.11(1H, dd, J=9 Hz), 7.26–7.38(5H, m), 7.53 (2H, d, J=9 Hz), 8.25(2H, d, J=9 Hz).

EXAMPLE 46

Production of 4-nitrobenzyl (9R,10R)-10-[2-(2-chloroacetamidothiazol-4-yl)-(Z)-2-methoxyiminoacetamido]-5,5-dimethyl-4,11-dioxo-3-oxa-8-thia-1-azatricyclo[7,2,0,0$^{2,6}$]undecane-2-carboxylate In 50 ml of dichloromethane was added 128 mg of the isomer A as obtained in Example 44. To the solution were added 130 μl of N,N-dimethylaniline and 116 mg of phosphorus pentachloride at −70° C., and the mixture was stirred at −60° C. for 50 minutes. To the reaction mixture was added 0.3 ml of aboulte methanol, and the mixture was stirred at −20° C. for 4.5 hours. To the resulting mixture was added water, followed by stirring at 0° C. for 30 minutes. To the reaction mixture was added an aqueous solution of sodium carbonate to adjust the pH of the aqueous layer to 6. To the reaction mixture was added 30 ml of dichloromethane, which was washed with a saturated aqueous saline solution, followed by drying (MgSO$_4$). The solvent was distilled off under reduced pressure, and the residue was dissolved in 5 ml of dichloromethane. To the solution were added under ice-cooling 80 μl of triethylamine and 115 mg of hydrochloride of 2-(2-chloroacetamidothiazol-4-yl)-(Z)-2-methoxyiminoacetyl chloride. The mixture was stirred for 40 minutes, after which was then added 2N HCl to adjust to pH 1. To the reaction mixture was added 30 ml of dichloromethane, and it was washed with a saturated aqueous saline solution, followed by drying (MgSO$_4$). The solvent was distilled off under reduced pressure, and the residue was allowed to pass through a column of silica gel, followed by elution with ethyl acetate-hexane (2:1). Fractions containing the object compound were combined and concentrated under reduced pressure to give 130 mg of the isomer A of the subject compound as powders.

IR $\nu_{max}^{CHCl_3}$ cm$^{-1}$: 1785, 1760, 1690.

NMR(90 MHz, CDCl$_3$) δ: 1.16(3H, s), 1.30 (3H, s), 2.60–3.30 (3H, m), 4.03(3H, s), 4.25(2H, s), 5.28(2H, q), 5.41(1H, d, J=4 Hz), 5.77(1H, dd, J=4, 9 Hz), 7.26(1H, s), 7.56(2H, d, J=9 Hz), 7.68(1H, bd, J=9 Hz), 8.18(2H, d, J=9 Hz).

EXAMPLE 47

Production of 4-nitrobenzyl (9R,10R)-10-[2-(2-aminothiazol-4-yl)-(Z)-2-methoxyiminoacetamido]-5,5-dimethyl-4,11-dioxo-3-oxa-8-thia-1-azatricyclo[7,2,0,0$^{2,6}$]undecane-2-carboxylate To a mixture of 5 ml of N,N-dimethylformamide and 5 ml of a 0.1M phosphate buffer solution of pH 7.0 were added 130 mg of the isomer A as obtained in Example 46 and 50 mg of sodium N-methyldithiocarbamate. The mixture was stirred for 90 minutes at room temperature. To the reaction mixture was added 30 ml of ethyl acetate, and it was washed with water three times, followed by drying (MgSO$_4$). The solvent was distilled off under reduced pressure, and the residue was allowed to pass through a column of silica gel, followed by elution with ethyl acetate-hexane-methanol (4.5:1). Fractions containing the object compound were combined and concentrated under reduced pressure to give 91 mg of the isomer A of the subject compound as an oily product.

IR $\nu_{max}^{CHCl_3}$ cm$^{-1}$: 1790, 1785, 1760, 1680.

NMR(90 MHz, CDCl$_3$) δ: 1.13(3H, s), 1.29(3H, s), 2.40–3.30 (3H, m), 4.00(3H, s), 5.23(2H, q), 5.38(1H, d, J=4 Hz), 5.68 (1H, bs), 5.78(1H, dd, J=4,8 Hz), 6.70(1H, s), 7.55 (2H, d, J=9 Hz), 7.90(1H, d, J=8 Hz), 8.16(2H, d, J=9 Hz).

EXAMPLE 48

Production of sodium (9R,10R)-10-[2-(2-aminothiazol-4-yl)-(Z)-2-methoxyiminoacetamido]-5,5-dimethyl-4,11-dioxo-3-oxa-8-thia-1-azatricyclo[7,2,0,0$^{2,6}$]undecane-2-carboxylate To a mixture of 5 ml of ethyl acetate and 5 ml of a 0.1M phosphate buffer solution of pH 7.0 were added 84 mg of the isomer A as obtained in Example 47 and 0.2 g of 10% palladium-carbon. The mixture was stirred for 80 minutes under ice-cooling while introducing hydrogen gas. To the reaction mixture was further added 0.12 g of 10% palladium-carbon, which was stirred for 1 hour. The catalyst was filtered off, and the aqueous layer was separated, followed by subjecting the remaining organic layer to extraction with 2 ml of water. The extract was combined with the aqueous layer, which was allowed to pass through a column of Amberlite XAD-2, followed by elution with water. Fractions containing the object compound were combined and lyophilized to give 39 mg of the isomer A of the subject compound as white powders.

IR $\nu_{max}^{KBr}$ cm$^{-1}$: 1770, 1760.

NMR(90 MHz, D$_2$O) δ: 1.26(3H, s), 1.29(3H, s), 2.85-3.18 (3H, m), 4.00(3H, s), 5.24(1H, d, J=5 Hz), 5.59(1H, d, J=5 Hz), 7.04(1H, s).

What we claim is:

1. A compound of the formula

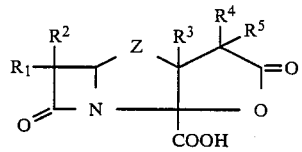

wherein $R^1$ represents an amino group; $R^2$ represents hydrogen, a methoxy group or a formylamino group; $R^3$, $R^4$ and $R^5$ independently represent hydrogen or an alkyl group; and Z represents a group represented by the formula —S—CH$_2$— or —CH$_2$—S—, its ester at the 2-carboxyl group, or its pharmacologically acceptable salt.

2. A compound as claimed in claim 1, wherein $R^2$ represents hydrogen.

3. A compound as claimed in claim 1, wherein $R^3$, $R^4$ and $R^5$ represent hydrogen.

4. A compound as claimed in claim 1, wherein Z represents a group of the formula —S—CH$_2$—.

5. A compound as claimed in claim 1, wherein $R^2$, $R^3$, $R^4$ represent hydrogen and Z represents a group of the formula —S—CH$_2$—.

* * * * *